(12) United States Patent
Gao et al.

(10) Patent No.: US 10,829,427 B2
(45) Date of Patent: Nov. 10, 2020

(54) NAPHTHOQUINONES, PRO-DRUGS, AND METHODS OF USE THEREOF

(71) Applicant: The Board of Regents of the University of Texas System, Austin, TX (US)

(72) Inventors: Jinming Gao, Plano, TX (US); Yuliang Liu, New York, NY (US); Qi Wei, Dallas, TX (US); Xinpeng Ma, Cambridge, MA (US); Gang Huang, Plano, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 16/063,347

(22) PCT Filed: Dec. 16, 2016

(86) PCT No.: PCT/US2016/067142
§ 371 (c)(1),
(2) Date: Jun. 18, 2018

(87) PCT Pub. No.: WO2017/106624
PCT Pub. Date: Jun. 22, 2017

(65) Prior Publication Data
US 2019/0071380 A1    Mar. 7, 2019

Related U.S. Application Data

(60) Provisional application No. 62/269,589, filed on Dec. 18, 2015.

(51) Int. Cl.
| | | |
|---|---|---|
| *C07C 50/32* | (2006.01) | |
| *C07C 311/08* | (2006.01) | |
| *C07C 311/21* | (2006.01) | |
| *C07C 225/30* | (2006.01) | |
| *C07C 233/91* | (2006.01) | |
| *C07C 233/18* | (2006.01) | |
| *C07C 271/30* | (2006.01) | |
| *C07C 205/46* | (2006.01) | |
| *C07C 311/09* | (2006.01) | |
| *C07C 233/31* | (2006.01) | |
| *C07D 317/70* | (2006.01) | |
| *C07C 311/51* | (2006.01) | |
| *A61K 9/00* | (2006.01) | |
| *A61K 9/51* | (2006.01) | |
| *A61P 35/00* | (2006.01) | |

(Continued)

(52) U.S. Cl.
CPC ............ *C07C 50/32* (2013.01); *A61K 9/0019* (2013.01); *A61K 9/5123* (2013.01); *A61K 9/5146* (2013.01); *A61P 35/00* (2018.01); *C07C 205/46* (2013.01); *C07C 225/30* (2013.01); *C07C 233/18* (2013.01); *C07C 233/31* (2013.01); *C07C 233/33* (2013.01); *C07C 233/42* (2013.01); *C07C 233/91* (2013.01); *C07C 271/30* (2013.01); *C07C 311/08* (2013.01); *C07C 311/09* (2013.01); *C07C 311/21* (2013.01); *C07C 311/51* (2013.01); *C07D 295/116* (2013.01); *C07D 317/70* (2013.01); *C07C 2601/14* (2017.05); *C07C 2602/10* (2017.05)

(58) Field of Classification Search
CPC .................................. C07C 50/32; A61P 35/00
See application file for complete search history.

(56) References Cited

U.S. PATENT DOCUMENTS

| | | |
|---|---|---|
| 4,195,998 A | 4/1980 | Adin et al. |
| 4,758,587 A | 7/1988 | Venuti |

(Continued)

FOREIGN PATENT DOCUMENTS

| | | |
|---|---|---|
| EP | 0413224 | 2/1991 |
| WO | WO 1996/033988 | 10/1996 |

(Continued)

OTHER PUBLICATIONS

Frydman et al (1997) : STN International HCAPLUS database, (Columbus, Ohio), Accession No. 1997: 594746.*

(Continued)

*Primary Examiner* — Golam M Shameem
(74) *Attorney, Agent, or Firm* — Parker Highlander PLLC

(57) ABSTRACT

Provided herein are naphthoquinones compounds such as those with a hydrogen bond donating group of the formula (I): wherein: $R_1$, $R_2$, $R_3$, $R_4$, $R_5$, and n are as defined herein. Also provided herein are pharmaceutical composition of the present compounds and methods of treatment using the compounds including their use in the treatment of cancer.

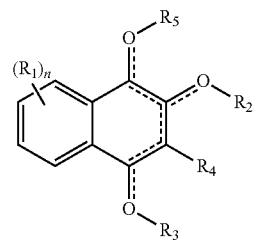

18 Claims, 12 Drawing Sheets

(51) Int. Cl.
*C07C 233/33* (2006.01)
*C07C 233/42* (2006.01)
*C07D 295/116* (2006.01)

(56) References Cited

U.S. PATENT DOCUMENTS

| | | |
|---|---|---|
| 5,883,270 A | 3/1999 | Frydman et al. |
| 5,977,187 A * | 11/1999 | Frydman ............ A61K 31/122 514/657 |
| 6,262,095 B1 | 7/2001 | Boutherin-Falson et al. |

FOREIGN PATENT DOCUMENTS

| | | |
|---|---|---|
| WO | WO 2004/045557 | 6/2004 |
| WO | WO 2006/128120 | 11/2006 |
| WO | WO 2008/066294 | 6/2008 |
| WO | WO 2009/105166 | 8/2009 |

OTHER PUBLICATIONS

Ditrich et al (1991) : STN International HCAPLUS database, (Columbus, Ohio), Accession No. 1991: 491867.*
Moehrle et al (1991) : STN International HCAPLUS database, (Columbus, Ohio), Accession No. 1991: 81731.*
Anderson et al (1980) : STN International HCAPLUS database, (Columbus, Ohio), Accession No. 1980: 85929.*
PCT International Preliminary Report on Patentability issued in International Application No. PCT/US2016/067142, dated Jun. 28, 2018.
PCT International Search Report and Written Opinion issued in International Application No. PCT/US2016/067142, dated Apr. 27, 2017.
PubChem CID 12692021, created Feb. 8, 2007.
PubChem CID 13660406, created Feb. 8, 2007.

* cited by examiner

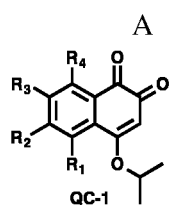
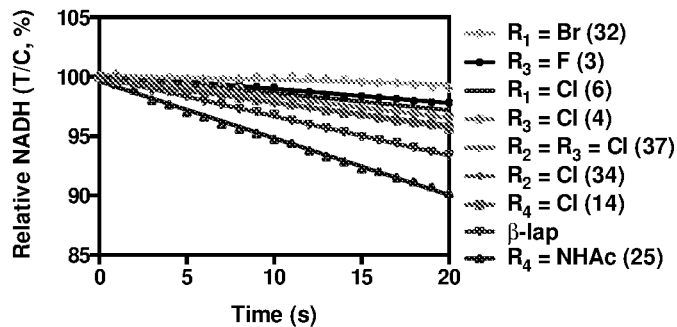
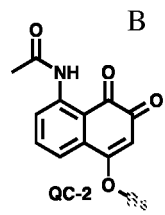
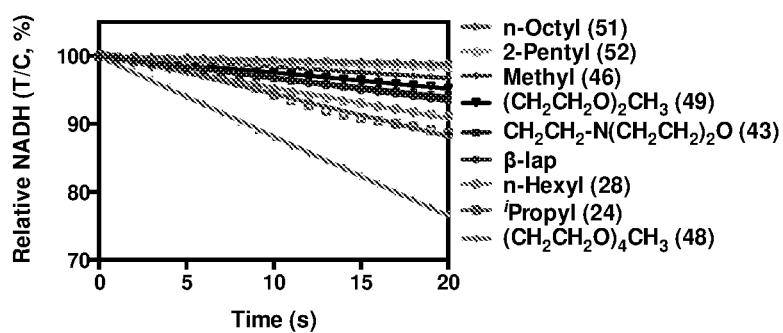
FIGS. 6A & 6B
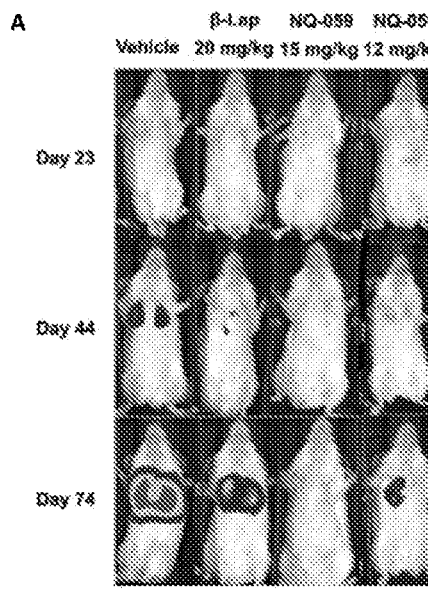
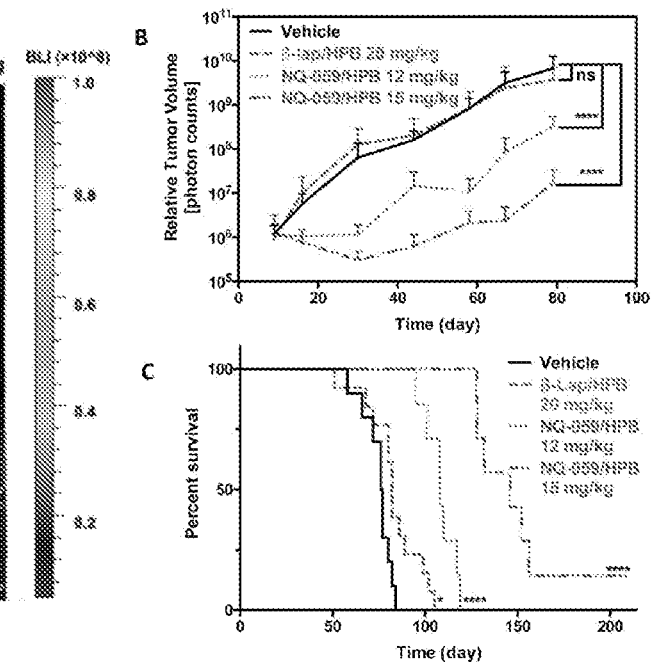
FIGS. 7A-7C

Formulation protection from hemolysis

NAPHTHOQUINONES, PRO-DRUGS, AND METHODS OF USE THEREOF

This application is a national phase application under 35 U.S.C. § 371 of International Application No. PCT/US2016/067142, filed Dec. 16, 2016, which claims the benefit of U.S. Provisional Application Ser. No. 62/269,589, filed on Dec. 18, 2015, the entirety of each of which is incorporated herein by reference.

BACKGROUND

1. Field

The present disclosure relates generally to the field of chemotherapeutic compounds. More particularly, it concerns naphthoquinones which are based on β-lapachone and may contain an intramolecular hydrogen bond.

2. Description of Related Art

Killing cancer cells specifically without affecting normal cells is the significantly difficult problem in the war to cure cancer. After balancing between the efficacy and the toxicity, the tumor specific target is the corner stone in this war. It has been proved that NAD(P)H quinone oxidoreductase (NQO1, DT diaphorase) is highly over-expressed in most solid tumors, such as breast carcinomas, lung cancer, pancreatic cancer, while in normal tissues the expression is low (Belinsky and Jaiswal, 1993; Joseph, et al., 1994; Malkinson, 1992; Marfn, et al., 1997). Through a 2-electron process, NQO1 can reduce toxic quinones to hydroquinones, which are usually stable with oxygen and can conjugate with molecules such as glucose, glutathione, or sulfate in vivo. However, some hydroquinone forms of naphthoquinones such as β-lapachone, a natural product extracted from *Tabebuia impetiginosa*, can immediately react with minimum oxygen in cells to generate semi-quinones, which can be further oxidized to quinone forms. Thus, through this futile cycle substantive oxygen in tumor can be immediately transformed into abundant reactive oxygen species (ROS), which can cause single strand DNA damage, PARP1 hyperactivation, and programmed cell necrosis in sequence. Till now, β-lapachone and derivatives thereof have been well known for its antitumor, anti-inflammatory, and anti-*Trypanosoma* effects. In the form of ARQ 501 & ARQ 761, β-lapachone has been applied into clinical trials to treat lung cancer and pancreatic cancer. Although many naphthoquinones have been prepared, most of them have not showed significant improvement on anti-tumor efficacy (WO 1996/033988; WO 2004/045557; WO 2006/128120; WO 2008/066294; WO 2009/105166; U.S. Pat. No. 6,262,095) There still remains a paramount need to develop more potent naphthoquinones in response to the NQO1 catalyzed futile cycle.

SUMMARY

In some aspects, the present disclosure provides compounds of the formula:

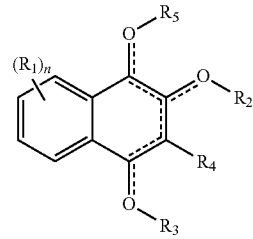

wherein:
R$_1$ is halo, hydroxy, nitro, alkyl$_{(C\leq 8)}$, substituted alkyl$_{(C\leq 8)}$, alkoxy$_{(C\leq 8)}$, substituted alkoxy$_{(C\leq 8)}$, or —NR$_a$R$_b$, wherein:
R$_a$ or R$_b$ are each independently hydrogen or —C(O)-alkoxy$_{(C\leq 12)}$, alkyl$_{(C\leq 12)}$, acyl$_{(C\leq 12)}$, alkylsulfonyl$_{(C\leq 12)}$, arylsulfonyl$_{(C\leq 12)}$, or a substituted version of any of these groups; or when n is more than 1, then both R$_1$ are taken together and are an alkoxydiyl$_{(C\leq 6)}$ or substituted alkoxydiyl$_{(C\leq 6)}$; or —O-alkanediyl$_{(C\leq 6)}$-R$_c$, wherein:
R$_c$ is amino, alkylamino$_{(C\leq 8)}$, dialkylamino$_{(C\leq 8)}$, heterocycloalkyl$_{(C\leq 8)}$, or a substituted version of any of these groups;

R$_2$ is absent or alkyl$_{(C\leq 12)}$, cycloalkyl$_{(C\leq 12)}$, acyl$_{(C\leq 12)}$, -alkanediyl$_{(C\leq 6)}$-R$_c$, or a substituted version of any of these groups; wherein:
R$_c$ is amino, alkylamino$_{(C\leq 8)}$, dialkylamino$_{(C\leq 8)}$, heterocycloalkyl$_{(C\leq 8)}$, or a substituted version of any of these groups;

provided that R$_2$ is absent when the atom to which R$_2$ is bound is a part of a double bond, and when the atom to which R$_2$ is bound is part of a double bond, then R$_2$ is absent;

R$_3$ is absent or alkyl$_{(C\leq 12)}$, cycloalkyl$_{(C\leq 12)}$, acyl$_{(C\leq 12)}$, -alkanediyl$_{(C\leq 6)}$-R$_c$, —(CH$_2$CH$_2$O)$_m$R$_d$, or a substituted version of any of these groups; wherein:
R$_c$ is amino, alkylamino$_{(C\leq 8)}$, dialkylamino$_{(C\leq 8)}$, heterocycloalkyl$_{(C\leq 8)}$, or a substituted version of any of these groups;

R$_d$ is hydrogen, alkyl$_{(C\leq 6)}$, or substituted alkyl$_{(C\leq 6)}$; and
m is 1, 2, 3, 4, or 5;

provided that R$_3$ is absent when the atom to which R$_3$ is bound is a part of a double bond, and when the atom to which R$_3$ is bound is part of a double bond, then R$_3$ is absent;

R$_4$ is hydrogen, halo, alkyl$_{(C\leq 6)}$, or substituted alkyl$_{(C\leq 6)}$;

R$_5$ is absent or alkyl$_{(C\leq 12)}$, acyl$_{(C\leq 12)}$, or a substituted version of either of these groups;

provided that R$_5$ is absent when the atom to which R$_5$ is bound is a part of a double bond, and when the atom to which R$_5$ is bound is part of a double bond, then R$_5$ is absent; and n is 0, 1, 2, 3, or 4;

provided that when R$_2$ and R$_5$ are acyl$_{(C\leq 12)}$ or substituted acyl$_{(C\leq 12)}$, then R$_3$ is alkyl$_{(C\leq 12)}$ or substituted alkyl$_{(C\leq 12)}$;

or a pharmaceutically acceptable salt thereof. In some embodiments, the compounds are further defined as:

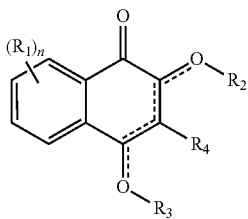

(II)

wherein:
R₁ is halo, hydroxy, nitro, alkyl$_{(C≤8)}$, substituted alkyl$_{(C≤8)}$, alkoxy$_{(C≤8)}$, substituted alkoxy$_{(C≤8)}$, or —NR$_a$R$_b$, wherein:
R$_a$ or R$_b$ are each independently hydrogen or —C(O)-alkoxy$_{(C≤12)}$, alkyl$_{(C≤12)}$, acyl$_{(C≤12)}$, alkylsulfonyl$_{(C≤12)}$, arylsulfonyl$_{(C≤12)}$, or a substituted version of any of these groups; or
when n is more than 1, then both R₁ are taken together and are an alkoxydiyl$_{(C≤6)}$ or substituted alkoxydiyl$_{(C≤6)}$; or
—O-alkanediyl$_{(C≤6)}$-R$_c$, wherein:
R$_c$ is amino, alkylamino$_{(C≤8)}$, dialkylamino$_{(C≤8)}$, heterocycloalkyl$_{(C≤8)}$, or a substituted version of any of these groups;
R₂ is absent or alkyl$_{(C≤12)}$, acyl$_{(C≤12)}$, -alkanediyl$_{(C≤6)}$-R$_c$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups;
provided that R₂ is absent when the atom to which R₂ is bound is a part of a double bond, and when the atom to which R₂ is bound is part of a double bond, then R₂ is absent;
R₃ is absent or alkyl$_{(C≤12)}$, acyl$_{(C≤12)}$, -alkanediyl$_{(C≤6)}$-R$_c$, —(CH₂CH₂O)$_m$R$_d$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups;
R$_d$ is hydrogen, alkyl$_{(C≤6)}$, or substituted alkyl$_{(C≤6)}$; and
m is 1, 2, 3, 4, or 5;
provided that R₃ is absent when the atom to which R₃ is bound is a part of a double bond, and when the atom to which R₃ is bound is part of a double bond, then R₃ is absent;
R₄ is hydrogen, halo, alkyl$_{(C≤6)}$, or substituted alkyl$_{(C≤6)}$; and
n is 0, 1, 2, 3, or 4;
or a pharmaceutically acceptable salt thereof. In some embodiments, the compounds are further defined as:

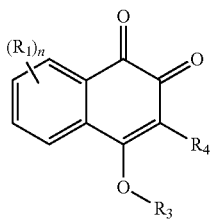

(III)

wherein:
R₁ is halo, hydroxy, nitro, alkyl$_{(C≤8)}$, substituted alkyl$_{(C≤8)}$, alkoxy$_{(C≤8)}$, substituted alkoxy$_{(C≤8)}$, or —NR$_a$R$_b$, wherein:
R$_a$ or R$_b$ are each independently hydrogen or —C(O)-alkoxy$_{(C≤12)}$, alkyl$_{(C≤12)}$, acyl$_{(C≤12)}$, alkylsulfonyl$_{(C≤12)}$, arylsulfonyl$_{(C≤12)}$, or a substituted version of any of these groups; or
when n is more than 1, then both R₁ are taken together and are an alkoxydiyl$_{(C≤6)}$ or substituted alkoxydiyl$_{(C≤6)}$; or
—O-alkanediyl$_{(C≤6)}$-R$_c$, wherein:
R$_c$ is amino, alkylamino$_{(C≤8)}$, dialkylamino$_{(C≤8)}$, heterocycloalkyl$_{(C≤8)}$, or a substituted version of any of these groups;
R₃ is alkyl$_{(C≤12)}$, acyl$_{(C≤12)}$, -alkanediyl$_{(C≤6)}$-R$_c$, —(CH₂CH₂O)$_m$R$_d$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups;
R$_d$ is hydrogen, alkyl$_{(C≤6)}$, or substituted alkyl$_{(C≤6)}$; and
m is 1, 2, 3, 4, or 5;
R₄ is hydrogen, halo, alkyl$_{(C≤6)}$, or substituted alkyl$_{(C≤6)}$; and
n is 0, 1, 2, 3, or 4;
or a pharmaceutically acceptable salt thereof. In some embodiments, the compounds are further defined as:

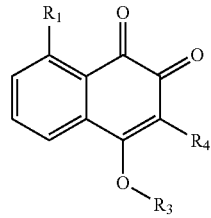

(IV)

wherein:
R₁ is halo, hydroxy, nitro, alkyl$_{(C≤8)}$, substituted alkyl$_{(C≤8)}$, alkoxy$_{(C≤8)}$, substituted alkoxy$_{(C≤8)}$, or —NR$_a$R$_b$, wherein:
R$_a$ or R$_b$ are each independently hydrogen or —C(O)-alkoxy$_{(C≤12)}$, alkyl$_{(C≤12)}$, acyl$_{(C≤12)}$, alkylsulfonyl$_{(C≤12)}$, arylsulfonyl$_{(C≤12)}$, or a substituted version of any of these groups;
R₃ is alkyl$_{(C≤12)}$, acyl$_{(C≤12)}$, -alkanediyl$_{(C≤6)}$-R$_c$, —(CH₂CH₂O)$_m$R$_d$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups;
R$_d$ is hydrogen, alkyl$_{(C≤6)}$, or substituted alkyl$_{(C≤6)}$; and
m is 1, 2, 3, 4, or 5; and
R₄ is hydrogen, halo, alkyl$_{(C≤6)}$, or substituted alkyl$_{(C≤6)}$;
or a pharmaceutically acceptable salt thereof. In some embodiments, the compounds are further defined as:

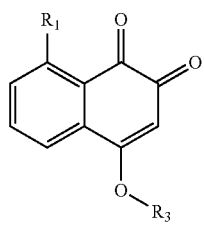

(V)

wherein:
R$_1$ is halo, hydroxy, nitro, alkyl$_{(C≤8)}$, substituted alkyl$_{(C≤8)}$, alkoxy$_{(C≤8)}$, substituted alkoxy$_{(C≤8)}$, or —NR$_a$R$_b$, wherein:
R$_a$ or R$_b$ are each independently hydrogen or —C(O)-alkoxy$_{(C≤12)}$, alkyl$_{(C≤12)}$, acyl$_{(C≤12)}$, alkylsulfonyl$_{(C≤12)}$, arylsulfonyl$_{(C≤12)}$, or a substituted version of any of these groups; and
R$_3$ is alkyl$_{(C≤12)}$, acyl$_{(C≤12)}$, -alkanediyl$_{(C≤6)}$-R$_c$, —(CH$_2$CH$_2$O)$_m$R$_d$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups;
R$_d$ is hydrogen, alkyl$_{(C≤6)}$, or substituted alkyl$_{(C≤6)}$; and
m is 1, 2, 3, 4, or 5;
or a pharmaceutically acceptable salt thereof. In some embodiments, the compounds are further defined as:

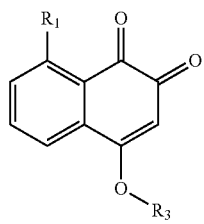

(V)

wherein:
R$_1$ is —NR$_a$R$_b$, wherein: R$_a$ or R$_b$ are each independently hydrogen or alkyl$_{(C≤12)}$, acyl$_{(C≤12)}$, alkylsulfonyl$_{(C≤12)}$, arylsulfonyl$_{(C≤12)}$, or a substituted version of any of these groups; and
R$_3$ is alkyl$_{(C≤12)}$, acyl$_{(C≤12)}$, -alkanediyl$_{(C≤6)}$-R$_c$, —(CH$_2$CH$_2$O)$_m$R$_d$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups;
R$_d$ is hydrogen, alkyl$_{(C≤6)}$, or substituted alkyl$_{(C≤6)}$; and
m is 1, 2, 3, 4, or 5;
or a pharmaceutically acceptable salt thereof. In other embodiments, the compounds are further defined as:

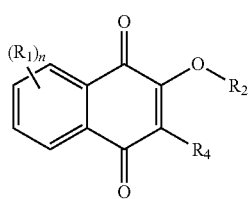

(VI)

wherein:
R$_1$ is halo, hydroxy, nitro, alkyl$_{(C≤8)}$, substituted alkyl$_{(C≤8)}$, alkoxy$_{(C≤8)}$, substituted alkoxy$_{(C≤8)}$, or —NR$_a$R$_b$, wherein:
R$_a$ or R$_b$ are each independently hydrogen or —C(O)-alkoxy$_{(C≤12)}$, alkyl$_{(C≤12)}$, acyl$_{(C≤12)}$, alkylsulfonyl$_{(C≤12)}$, arylsulfonyl$_{(C≤12)}$, or a substituted version of any of these groups; or
when n is more than 1, then both R$_1$ are taken together and are an alkoxydiyl$_{(C≤6)}$ or substituted alkoxydiyl$_{(C≤6)}$; or
—O-alkanediyl$_{(C≤6)}$-R$_c$, wherein:
R$_c$ is amino, alkylamino$_{(C≤8)}$, dialkylamino$_{(C≤8)}$, heterocycloalkyl$_{(C≤8)}$, or a substituted version of any of these groups;
R$_2$ is alkyl$_{(C≤12)}$, acyl$_{(C≤12)}$, -alkanediyl$_{(C≤6)}$-R$_c$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups;
R$_4$ is hydrogen, halo, alkyl$_{(C≤6)}$, or substituted alkyl$_{(C≤6)}$; and
n is 0, 1, 2, 3, or 4;
or a pharmaceutically acceptable salt thereof. In some embodiments, the compounds are further defined as:

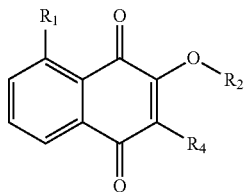

(VII)

wherein:
R$_1$ is halo, hydroxy, nitro, alkyl$_{(C≤8)}$, substituted alkyl$_{(C≤8)}$, alkoxy$_{(C≤8)}$, substituted alkoxy$_{(C≤8)}$, or —NR$_a$R$_b$, wherein:
R$_a$ or R$_b$ are each independently hydrogen or —C(O)-alkoxy$_{(C≤12)}$, alkyl$_{(C≤12)}$, acyl$_{(C≤12)}$, alkylsulfonyl$_{(C≤12)}$, arylsulfonyl$_{(C≤12)}$, or a substituted version of any of these groups;
R$_2$ is alkyl$_{(C≤12)}$, acyl$_{(C≤12)}$, -alkanediyl$_{(C≤6)}$-R$_c$, or a substituted version of any of these groups; wherein:
R$_c$ is amino, alkylamino$_{(C≤8)}$, dialkylamino$_{(C≤8)}$, heterocycloalkyl$_{(C≤8)}$, or a substituted version of any of these groups; and
R$_4$ is hydrogen, halo, alkyl$_{(C≤6)}$, or substituted alkyl$_{(C≤6)}$;
or a pharmaceutically acceptable salt thereof. In some embodiments, the compounds are further defined as:

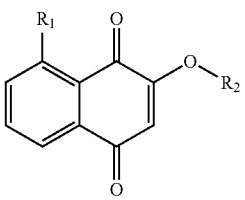

(VIII)

wherein:
R$_1$ is halo, hydroxy, nitro, alkyl$_{(C≤8)}$, substituted alkyl$_{(C≤8)}$, alkoxy$_{(C≤8)}$, substituted alkoxy$_{(C≤8)}$, or —NR$_a$R$_b$, wherein:

$R_a$ or $R_b$ are each independently hydrogen or —C(O)-alkoxy$_{(C\leq12)}$, alkyl$_{(C\leq12)}$, acyl$_{(C\leq12)}$, alkylsulfonyl$_{(C\leq12)}$, arylsulfonyl$_{(C\leq12)}$, or a substituted version of any of these groups; and $R_2$ is alkyl$_{(C\leq12)}$, acyl$_{(C\leq12)}$, -alkanediyl$_{(C\leq6)}$-$R_c$, or a substituted version of any of these groups; wherein:

$R_c$ is amino, alkylamino$_{(C\leq8)}$, dialkylamino$_{(C\leq8)}$, heterocycloalkyl$_{(C\leq8)}$, or a substituted version of any of these groups;

or a pharmaceutically acceptable salt thereof. In some embodiments, the compounds are further defined as:

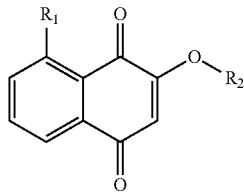

(VIII)

wherein:

$R_1$ is —$NR_aR_b$, wherein: $R_a$ or $R_b$ are each independently hydrogen or alkyl$_{(C\leq12)}$, acyl$_{(C\leq12)}$, alkylsulfonyl$_{(C\leq12)}$, arylsulfonyl$_{(C\leq12)}$, or a substituted version of any of these groups; and $R_2$ is oxo or alkyl$_{(C\leq12)}$, acyl$_{(C\leq12)}$, -alkanediyl$_{(C\leq6)}$-$R_c$, or a substituted version of any of these groups; wherein:

$R_c$ is amino, alkylamino$_{(C\leq8)}$, dialkylamino$_{(C\leq8)}$, heterocycloalkyl$_{(C\leq8)}$, or a substituted version of any of these groups;

or a pharmaceutically acceptable salt thereof. In other embodiments, the compounds are further defined as:

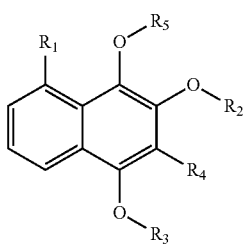

(IX)

wherein:

$R_1$ is halo, hydroxy, nitro, alkyl$_{(C\leq8)}$, substituted alkyl$_{(C\leq8)}$, alkoxy$_{(C\leq8)}$, substituted alkoxy$_{(C\leq8)}$, or —$NR_aR_b$, wherein:

$R_a$ or $R_b$ are each independently hydrogen or —C(O)-alkoxy$_{(C\leq12)}$, alkyl$_{(C\leq12)}$, acyl$_{(C\leq12)}$, alkylsulfonyl$_{(C\leq12)}$, arylsulfonyl$_{(C\leq12)}$, or a substituted version of any of these groups; or when n is more than 1, then both $R_1$ are taken together and are an alkoxydiyl$_{(C\leq6)}$ or substituted alkoxydiyl$_{(C\leq6)}$; or —O-alkanediyl$_{(C\leq6)}$-$R_c$, wherein:

$R_c$ is amino, alkylamino$_{(C\leq8)}$, dialkylamino$_{(C\leq8)}$, heterocycloalkyl$_{(C\leq8)}$, or a substituted version of any of these groups;

$R_2$ is alkyl$_{(C\leq12)}$, acyl$_{(C\leq12)}$, -alkanediyl$_{(C\leq6)}$-$R_c$, or a substituted version of any of these groups; wherein:

$R_c$ is amino, alkylamino$_{(C\leq8)}$, dialkylamino$_{(C\leq8)}$, heterocycloalkyl$_{(C\leq8)}$, or a substituted version of any of these groups;

$R_3$ is alkyl$_{(C\leq12)}$, acyl$_{(C\leq12)}$, -alkanediyl$_{(C\leq6)}$-$R_c$, —(CH$_2$CH$_2$O)$_m$$R_d$, or a substituted version of any of these groups; wherein:

$R_c$ is amino, alkylamino$_{(C\leq8)}$, dialkylamino$_{(C\leq8)}$, heterocycloalkyl$_{(C\leq8)}$, or a substituted version of any of these groups;

$R_d$ is hydrogen, alkyl$_{(C\leq6)}$, or substituted alkyl$_{(C\leq6)}$; and m is 1, 2, 3, 4, or 5;

$R_4$ is hydrogen, halo, alkyl$_{(C\leq6)}$, or substituted alkyl$_{(C\leq6)}$;

$R_5$ is alkyl$_{(C\leq12)}$, acyl$_{(C\leq12)}$, or a substituted version of either of these groups; and provided that when $R_2$ and $R_5$ are acyl$_{(C\leq12)}$ or substituted acyl$_{(C\leq12)}$, then $R_3$ is alkyl$_{(C\leq12)}$ or substituted alkyl$_{(C\leq12)}$;

or a pharmaceutically acceptable salt thereof. In some embodiments, the compounds are further defined as:

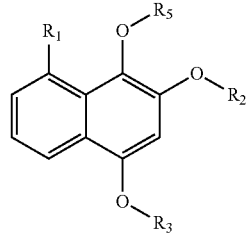

(X)

wherein:

$R_1$ is —$NR_aR_b$, wherein: $R_a$ or $R_b$ are each independently hydrogen or alkyl$_{(C\leq12)}$, acyl$_{(C\leq12)}$, alkylsulfonyl$_{(C\leq12)}$, arylsulfonyl$_{(C\leq12)}$, or a substituted version of any of these groups;

$R_2$ is alkyl$_{(C\leq12)}$, acyl$_{(C\leq12)}$, -alkanediyl$_{(C\leq6)}$-$R_c$, or a substituted version of any of these groups; wherein:

$R_c$ is amino, alkylamino$_{(C\leq8)}$, dialkylamino$_{(C\leq8)}$, heterocycloalkyl$_{(C\leq8)}$, or a substituted version of any of these groups;

$R_3$ is alkyl$_{(C\leq12)}$, acyl$_{(C\leq12)}$, -alkanediyl$_{(C\leq6)}$-$R_c$, —(CH$_2$CH$_2$O)$_m$$R_d$, or a substituted version of any of these groups; wherein:

$R_c$ is amino, alkylamino$_{(C\leq8)}$, dialkylamino$_{(C\leq8)}$, heterocycloalkyl$_{(C\leq8)}$, or a substituted version of any of these groups;

$R_d$ is hydrogen, alkyl$_{(C\leq6)}$, or substituted alkyl$_{(C\leq6)}$; and m is 1, 2, 3, 4, or 5;

$R_5$ is alkyl$_{(C\leq12)}$, acyl$_{(C\leq12)}$, or a substituted version of either of these groups; and provided that when $R_2$ and $R_5$ are acyl$_{(C\leq12)}$ or substituted acyl$_{(C\leq12)}$, then $R_3$ is alkyl$_{(C\leq12)}$ or substituted alkyl$_{(C\leq12)}$;

or a pharmaceutically acceptable salt thereof. In some embodiments, the compounds are further defined as:

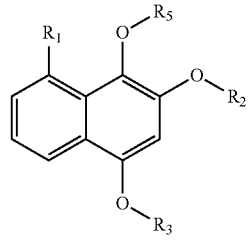

(X)

wherein:
R$_1$ is —NR$_a$R$_b$, wherein: R$_a$ or R$_b$ are each independently hydrogen or alkyl$_{(C≤12)}$, acyl$_{(C≤12)}$, alkylsulfonyl$_{(C≤12)}$, arylsulfonyl$_{(C≤12)}$, or a substituted version of any of these groups;
R$_2$ is acyl$_{(C≤12)}$ or substituted acyl$_{(C≤12)}$;
R$_3$ is alkyl$_{(C≤12)}$ or substituted alkyl$_{(C≤12)}$; wherein:
R$_5$ is acyl$_{(C≤12)}$ or substituted acyl$_{(C≤12)}$; and
or a pharmaceutically acceptable salt thereof.

In some embodiments, R$_1$ is halo such as bromo, chloro, or fluoro. In other embodiments, R$_1$ is nitro. In other embodiments, R$_1$ is hydroxy. In other embodiments, R$_1$ is alkyl$_{(C≤8)}$ or substituted alkyl$_{(C≤8)}$. In some embodiments, R$_1$ is alkyl$_{(C≤8)}$ such as methyl. In other embodiments, R$_1$ is alkoxy$_{(C≤8)}$ or substituted alkoxy$_{(C≤8)}$. In some embodiments, R$_1$ is alkoxy$_{(C≤8)}$ such as methoxy. In other embodiments, n is 2 and R$_1$ is alkoxydiyl$_{(C≤6)}$ or substituted alkoxydiyl$_{(C≤6)}$. In some embodiments, R$_1$ is alkoxydiyl$_{(C≤6)}$ such as —OCH$_2$O—. In some embodiments, R$_1$ is —NR$_a$R$_b$, wherein: R$_a$ or R$_b$ are each independently hydrogen or —C(O)-alkoxy$_{(C≤12)}$, alkyl$_{(C≤12)}$, acyl$_{(C≤12)}$, alkylsulfonyl$_{(C≤12)}$, arylsulfonyl$_{(C≤12)}$, or a substituted version of any of these groups.

In some embodiments, R$_a$ is hydrogen. In other embodiments, R$_a$ is alkyl$_{(C≤8)}$ or substituted alkyl$_{(C≤8)}$. In some embodiments, R$_a$ is alkyl$_{(C≤8)}$ such as isopropyl. In other embodiments, R$_a$ is acyl$_{(C≤8)}$ or substituted acyl$_{(C≤8)}$. In some embodiments, R$_a$ is acyl$_{(C≤8)}$ such as acetyl or propionyl. In other embodiments, R$_a$ is substituted acyl$_{(C≤8)}$ such as trifluoroacetyl. In other embodiments, R$_a$ is —C(O)-alkoxy$_{(C≤12)}$ such as —C(O)OtBu. In other embodiments, R$_a$ is alkylsulfonyl$_{(C≤8)}$ or substituted alkylsulfonyl$_{(C≤8)}$. In some embodiments, R$_a$ is alkylsulfonyl$_{(C≤8)}$ such as methylsulfonyl. In other embodiments, R$_a$ is substituted alkylsulfonyl$_{(C≤8)}$ such as trifluoromethylsulfonyl. In other embodiments, R$_a$ is arylsulfonyl$_{(C≤8)}$ or substituted arylsulfonyl$_{(C≤8)}$. In some embodiments, R$_a$ is arylsulfonyl$_{(C≤8)}$ such as 4-tolylsulfonyl. In some embodiments, R$_b$ is hydrogen. In other embodiments, R$_b$ is acyl$_{(C≤8)}$ or substituted acyl$_{(C≤8)}$. In some embodiments, R$_b$ is acyl$_{(C≤8)}$ such as acetyl or propionyl.

In some embodiments, R$_2$ is absent. In other embodiments, R$_2$ is alkyl$_{(C≤8)}$ or substituted alkyl$_{(C≤8)}$. In some embodiments, R$_2$ is alkyl$_{(C≤8)}$ such as isopropyl. In other embodiments, R$_2$ is acyl$_{(C≤8)}$ or substituted acyl$_{(C≤8)}$. In some embodiments, R$_2$ is acyl$_{(C≤8)}$ such as acetyl or propionyl. In other embodiments, R$_2$ is -alkanediyl$_{(C≤6)}$-R$_c$, wherein: R$_c$ is amino, alkylamino$_{(C≤8)}$, dialkylamino$_{(C≤8)}$, heterocycloalkyl$_{(C≤8)}$, or a substituted version of any of these groups. In some embodiments, the alkanediyl$_{(C≤6)}$ is —CH$_2$— or —CH$_2$CH$_2$—. In some embodiments, R$_c$ is amino. In other embodiments, R$_c$ is dialkylamino$_{(C≤8)}$ or substituted dialkylamino$_{(C≤8)}$. In some embodiments, R$_c$ is dialkylamino$_{(C≤8)}$ such as dimethylamino. In other embodiments, R$_c$ is heterocycloalkyl$_{(C≤8)}$ or substituted heterocycloalkyl$_{(C≤8)}$. In some embodiments, R$_c$ is heterocycloalkyl$_{(C≤8)}$ such as morpholinyl.

In some embodiments, R$_3$ is absent. In other embodiments, R$_3$ is alkyl$_{(C≤8)}$ or substituted alkyl$_{(C≤8)}$. In some embodiments, R$_3$ is alkyl$_{(C≤8)}$ such as butyl, hexyl, octyl, or 1-ethylpropyl. In other embodiments, R$_3$ is substituted alkyl$_{(C≤8)}$ such as 3-hydroxypropyl. In other embodiments, R$_3$ is acyl$_{(C≤8)}$ or substituted acyl$_{(C≤8)}$. In some embodiments, R$_3$ is acyl$_{(C≤8)}$ such as acetyl or propionyl. In other embodiments, R$_3$ is -alkanediyl$_{(C≤6)}$-R$_c$, wherein: R$_c$ is amino, alkylamino$_{(C≤8)}$, dialkylamino$_{(C≤8)}$, heterocycloalkyl$_{(C≤8)}$, or a substituted version of any of these groups.

In some embodiments, the alkanediyl$_{(C≤6)}$ is —CH$_2$— or —CH$_2$CH$_2$—. In some embodiments, R$_c$ is amino. In other embodiments, R$_c$ is dialkylamino$_{(C≤8)}$ or substituted dialkylamino$_{(C≤8)}$. In some embodiments, R$_c$ is dialkylamino$_{(C≤8)}$ such as dimethylamino. In other embodiments, R$_c$ is heterocycloalkyl$_{(C≤8)}$ or substituted heterocycloalkyl$_{(C≤8)}$. In some embodiments, R$_c$ is heterocycloalkyl$_{(C≤8)}$ such as morpholinyl. In other embodiments, R$_3$ is —(CH$_2$CH$_2$O)$_m$R$_d$, wherein: R$_d$ is hydrogen, alkyl$_{(C≤6)}$, or substituted alkyl$_{(C≤6)}$; and m is 1, 2, 3, 4, or 5. In some embodiments, m is 2, 3, or 4. In some embodiments, m is 2. In other embodiments, m is 4. In some embodiments, R$_d$ is hydrogen. In other embodiments, R$_d$ is alkyl$_{(C≤8)}$ or substituted alkyl$_{(C≤8)}$. In some embodiments, R$_d$ is alkyl$_{(C≤8)}$ such as methyl.

In some embodiments, R$_4$ is hydrogen. In other embodiments, R$_4$ is halo such as bromo or chloro. In other embodiments, R$_4$ is alkyl$_{(C≤6)}$ or substituted alkyl$_{(C≤6)}$. In some embodiments, R$_4$ is alkyl$_{(C≤6)}$ such as methyl. In some embodiments, R$_5$ is absent. In other embodiments, R$_5$ is acyl$_{(C≤8)}$ or substituted acyl$_{(C≤8)}$. In some embodiments, R$_5$ is acyl$_{(C≤8)}$ such as acetyl or propionyl. In some embodiments, n is 0, 1, 2, or 3. In some embodiments, n is 0. In other embodiments, n is 1. In other embodiments, n is 2.

In some embodiments, the compounds are further defined as:

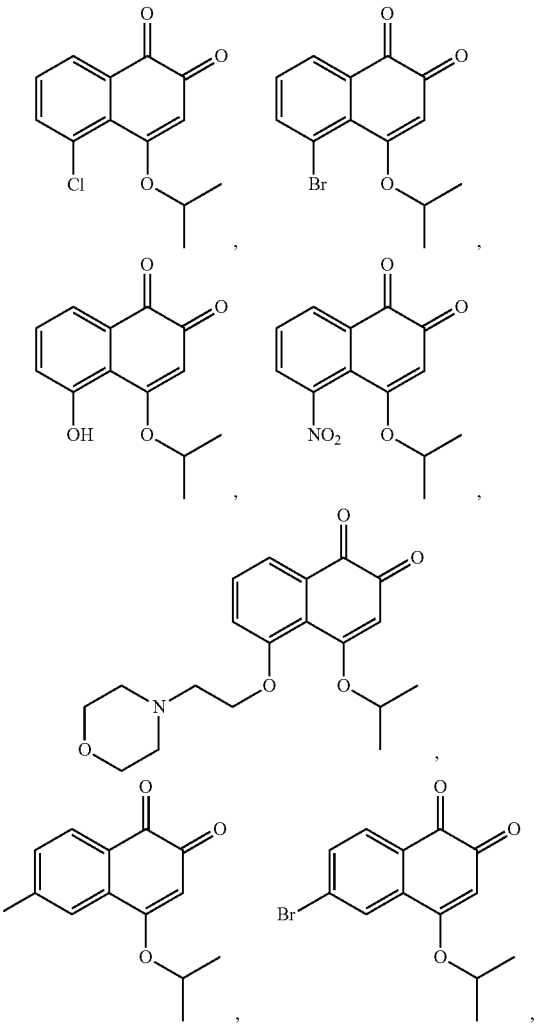

-continued
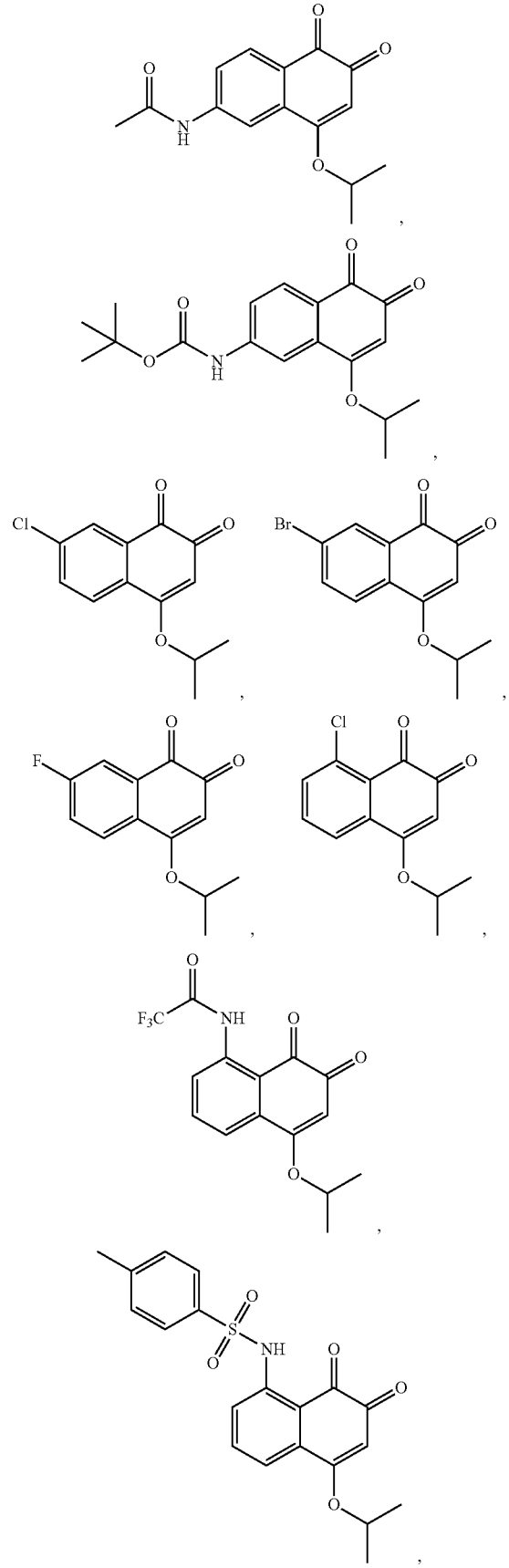
-continued
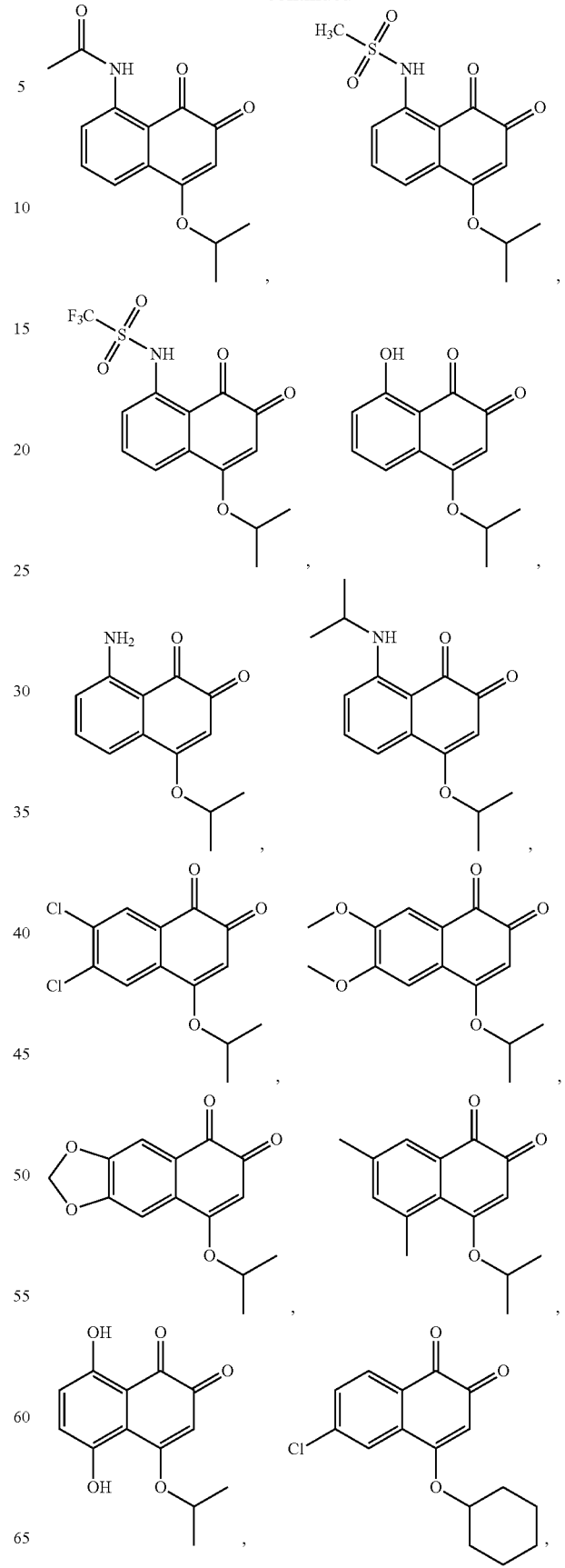

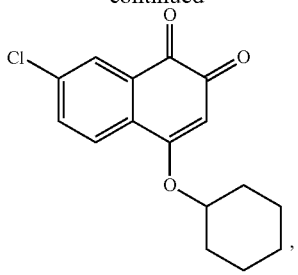
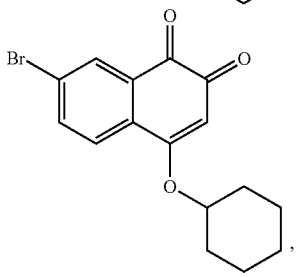
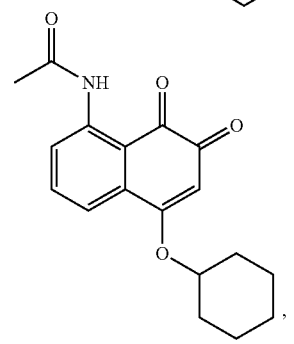
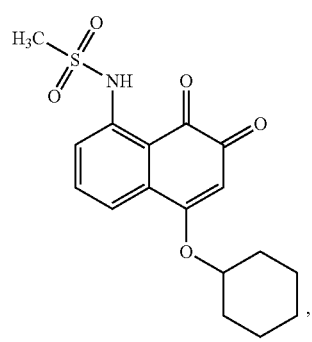
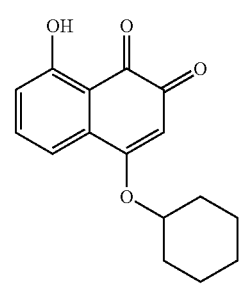
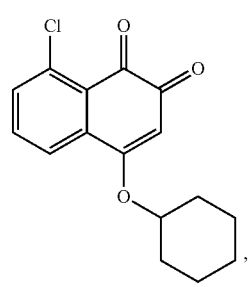
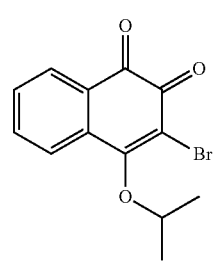
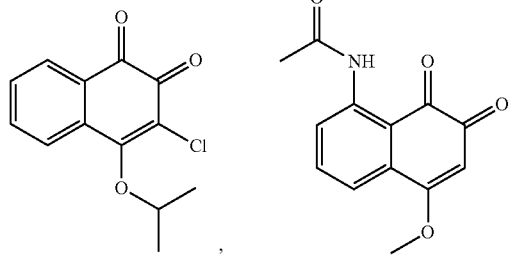
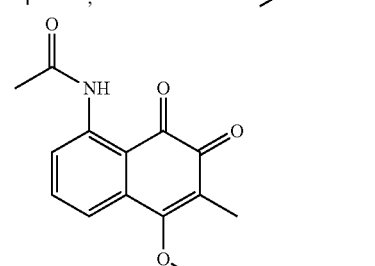
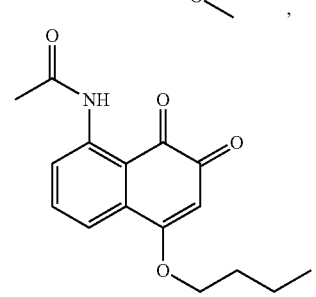
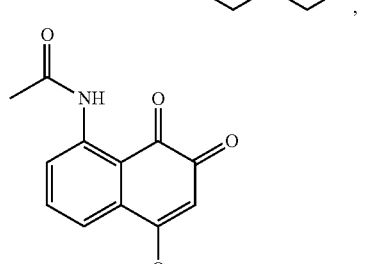
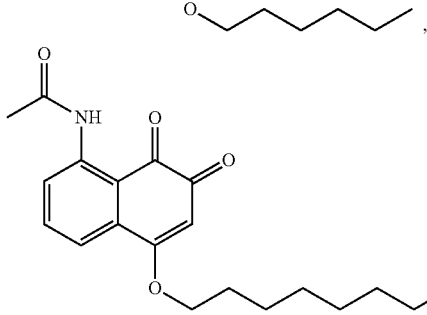
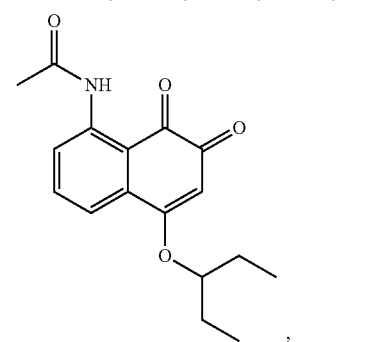

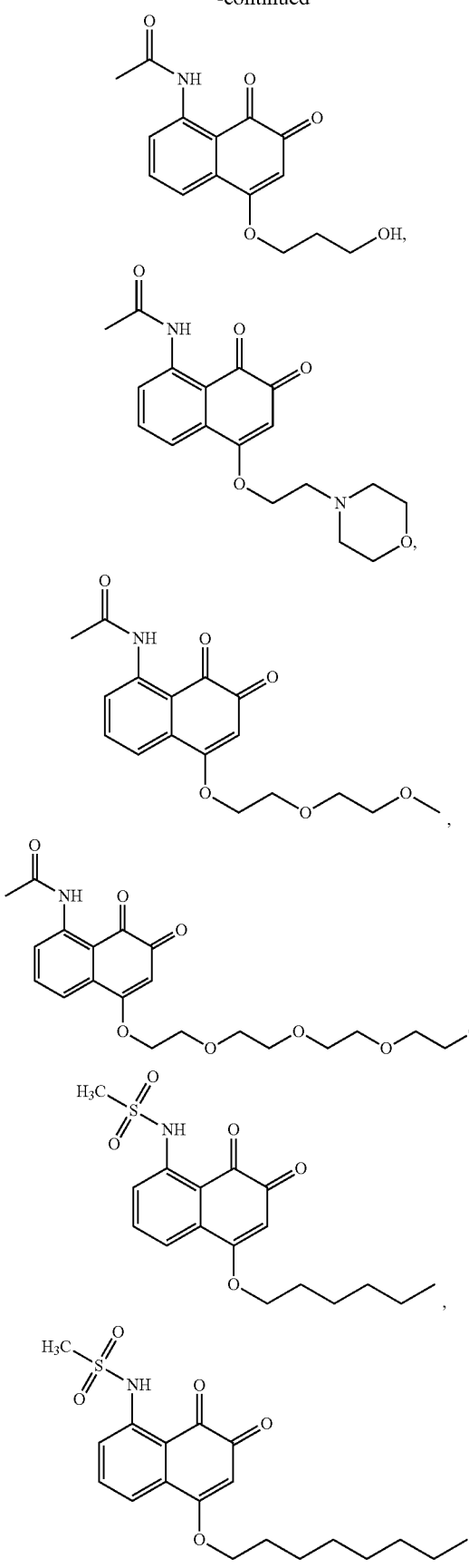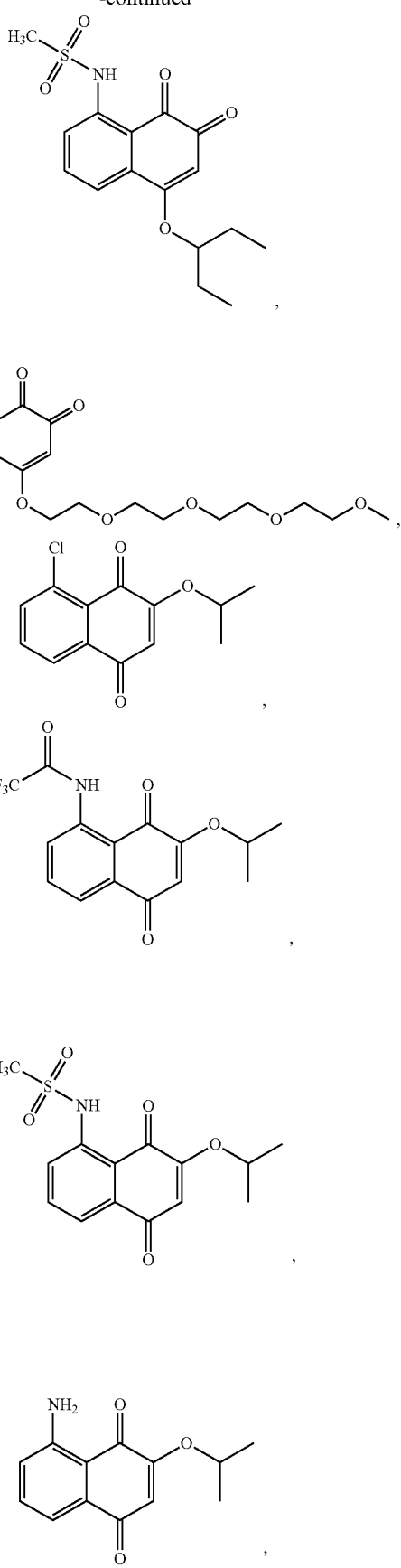

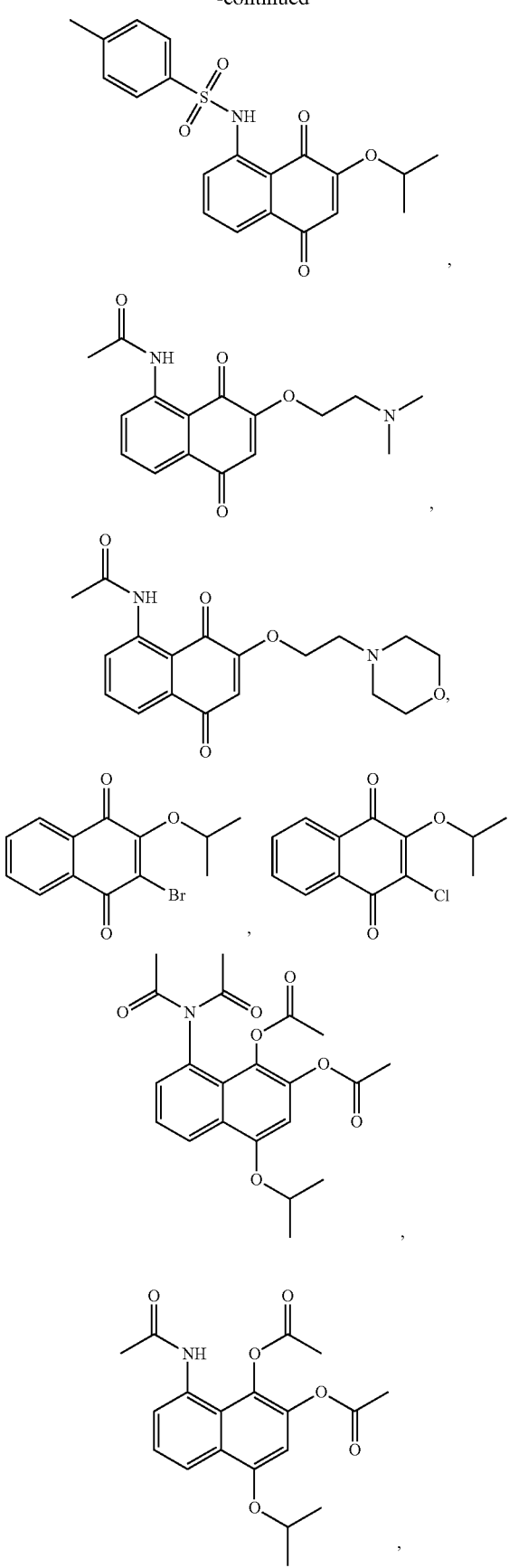
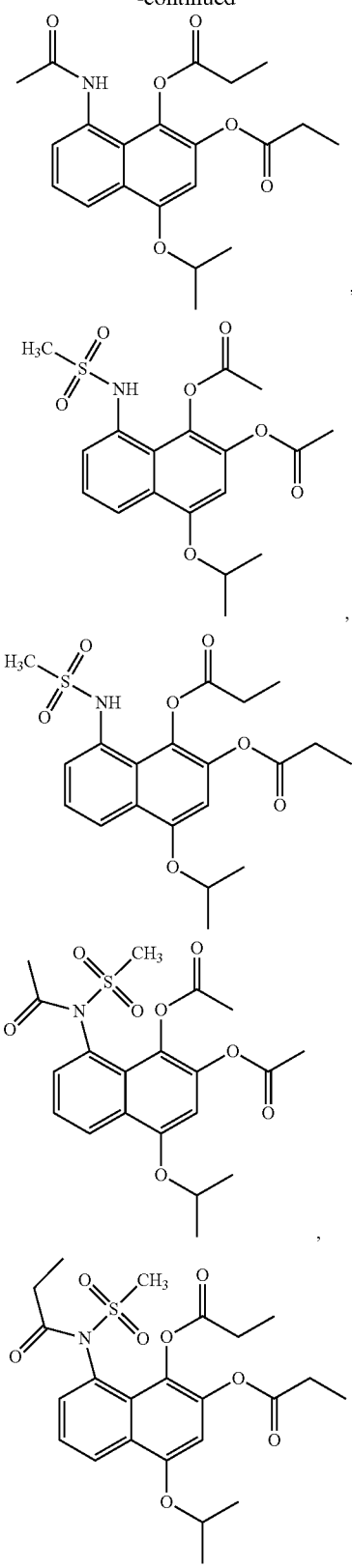
or a pharmaceutically acceptable salt.
In some embodiments, the compounds are further defined as:

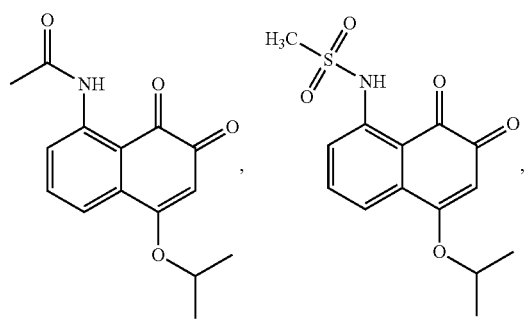

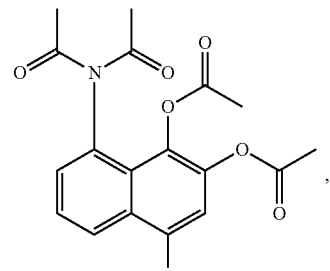

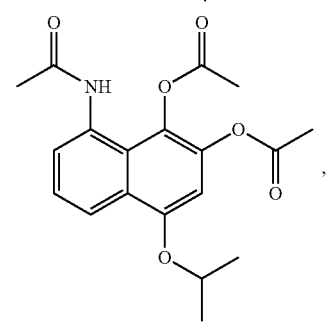

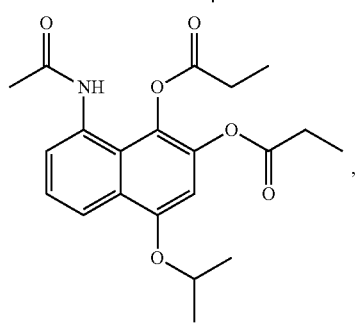

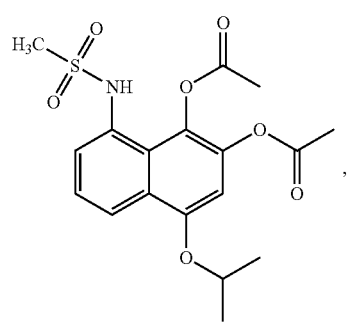

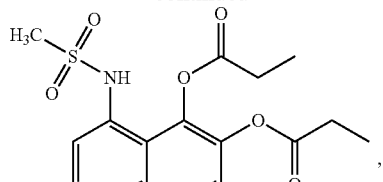

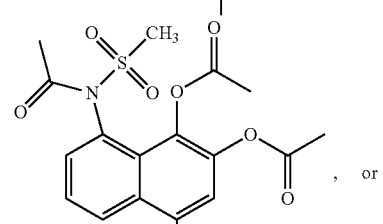

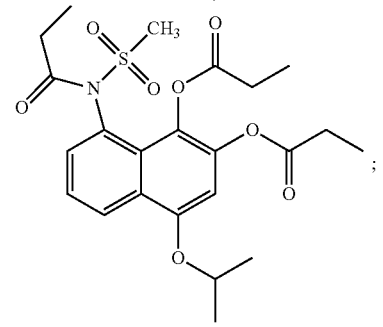 [SMILES: CCC(=O)Oc1cc(OC(C)C)c2cccc(N(C(=O)CC)S(C)(=O)=O)c2c1OC(=O)CC]

or a pharmaceutically acceptable salt.

In yet another aspect, the present disclosure provides pharmaceutical compositions comprising:
 (a) a compound according to any one of claims 1-108; and
 (b) a pharmaceutically acceptable carrier.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical composition is formulated for intravenous injection and intraperitoneal injection. In some embodiments, the compound is formulated in a cyclodextran. In some embodiments, the cyclodextran is hydroxypropyl-β-cyclodextran. In other embodiments, the compound is formulated in a nanoparticle. In some embodiments, the nanoparticle is a PEG-PLA diblock copolymer, a PEG-PCL diblock copolymer, a PEG-PLGA diblock copolymer, a PEG-PLA-PEG triblock copolymer, a PEG-PCL-PEG triblock copolymer, or a PEG-PLGA-PEG triblock copolymer. In some embodiments, the nanoparticle is a PEG-PLA diblock copolymer. In some embodiments, the nanoparticle further comprises a monoglyceride$_{(C≤18)}$. In some embodiments, the pharmaceutical composition comprising:

(a) from about 1% to about 20% of the compound;
(b) from about 80% to about 99% of the PEG-PLA diblock copolymer; and
(c) from about 0.1% to about 10% of the monoglyceride$_{(C≤18)}$;

provided that (a), (b), and (c) are at least 95% of the pharmaceutical composition. In some embodiments, the pharmaceutical composition comprises about 10% of the compound, about 1% of the monoglyceride$_{(C≤18)}$, and 89% of the PEG-PLA diblock copolymer. In some embodiments, the pharmaceutical composition is formulated as a unit dose.

In still yet another aspect, the present disclosure provides methods of treating a disease or disorder in a patient comprising administering to the patient in need thereof a therapeutically effective amount of a compound or composition described herein. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is brain cancer, breast cancer, colon cancer, head and neck cancer, lung cancer, pancreatic cancer, or prostate cancer. In some embodiments, the cancer is lung cancer such as lung adenocarcinoma. In other embodiments, the cancer is pancreatic cancer such as pancreas adenocarcinoma. In some embodiments, the methods comprise administering a second anti-cancer therapy. In some embodiments, the second anti-cancer therapy is a second chemotherapeutic compound, radiotherapy, immunotherapy, or surgery. In other embodiments, the disease is a disease associated with inflammation. In other embodiments, the disease is an infection caused by a fungus, bacterium, or a parasite. In some embodiments, the disease is an infection caused by a parasite such as parasite infection causes malaria or trypanosomiasis. In other embodiments, the disease or disorder is aging. In some embodiments, the patient is a mammal. In some embodiments, the patient is a human. In some embodiments, the method comprises administering the compound once. In other embodiments, the method comprises administering the compound two or more times.

In some aspects, the present disclosure provides naphthoquinones which contain an intramolecular hydrogen bond donor which interacts with one of the carbonyls in the diketone group.

In still yet another aspect, the present disclosure provides pharmaceutical compositions containing at least one compound of Formula (I) and a pharmaceutically acceptable carrier, such as a diluent, solvent, or excipient.

In yet another aspect, the present disclosure also provides for the use of compounds of Formula (I) for the preparation of pharmaceutical compositions, and the subsequent use of the compositions in the treatment of patients or subjects. Patients or subjects may be mammals, including humans. In some embodiments, the present disclosure provides methods of treating, killing, or inhibiting the growth tumor cells or *Trypanosoma cruzi* that have elevated NQO1 levels or a tumor having cells that have elevated NQO1 levels, wherein at least one tumor cell is exposed to a therapeutically effective amount of a compound of Formula (I), a pharmaceutically acceptable salt or solvate thereof, or a pharmaceutically acceptable composition thereof.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 6A & 6B show h-NQO1 enzyme assay to test NADH consumption rate of the naphthaquinones for compounds with groups on the aryl ring based upon core structure QC-1 (FIG. 6A) and the ether group para to the carbonyl based upon core structure QC-2 (FIG. 6B).

FIGS. 7A-7C show the in vivo anti-tumor efficacy on NOD-SCID mice bearing orthotopic A549 model. Tumor growth quantified with bioluminescence imaging. (FIG. 7A) Statistic result of tumor growth quantified with bioluminescence imaging. (FIG. 7B) Long term survival after treatment. P values are all relative to Vehicle groups; ns, no significance; *P<0.02; **** P<0.0001. (FIG. 7C)

DESCRIPTION OF ILLUSTRATIVE EMBODIMENTS

Figure 1:
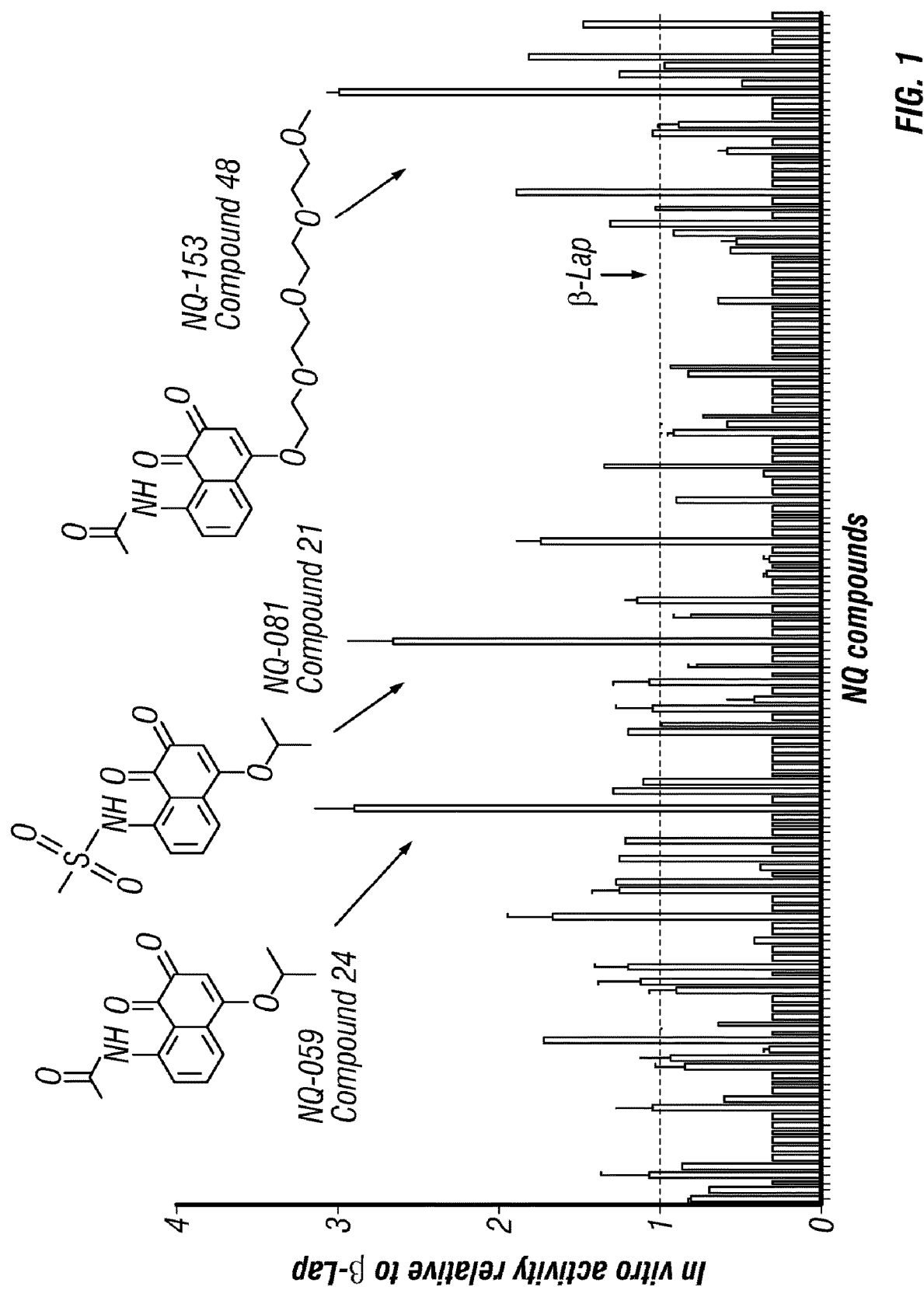
FIG. 1 shows the activity of different substituents basing on core structure of Formula (I) with the inhibition activity relative to β-lapachone.

In some aspects, the present disclosure provides naphthoquinones derivatives which may contain a hydrogen bonding group adjacent to the carbonyl thus forming an intramolecular hydrogen bond. In some embodiments, these compounds can be prepared as a pro-drug. These compounds and pro-drugs may be used in the treatment of cancer such as NQO1 dependent cancers.

I. COMPOUNDS OF THE PRESENT DISCLOSURE

The compounds provided by the present disclosure are shown, for example, above in the Summary and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. CANCER AND OTHER HYPERPROLIFERATIVE DISEASES

While hyperproliferative diseases can be associated with any disease, which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the naphthoquinones analogs described herein may be used to lead to decreased cell counts and as such can potentially be used to treat a variety of types of cancer lines. In some aspects, it is anticipated that the naphthoquinones analogs described herein may be used to treat virtually any malignancy.

In some aspects, the compounds of the present disclosure may be used in the treatment of NQO1 dependent cancers. NQO1 is known to regulate p53 activity and thus useful in the treatment of hyperproliferative diseases such as cancer. Additionally, NQO1 acts as a detoxification protein, which removes reactive oxygen species from the cell thus reducing oxidative damage and cancer. Modification of NQO1 activity and expression is therefore useful in the treatment of cancer. Some non-limiting examples of cancers, which have been associated with mis-regulation of NQO1, include but are not limited to bladder cancer, breast cancer, colorectal cancer, prostate cancer or acute lymphoblastic leukemia.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. PHARMACEUTICAL COMPOSITIONS, FORMULATIONS, AND ROUTES OF ADMINISTRATION

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active naphthoquinones analogs compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free bases or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the naphthoquinones analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The naphthoquinones analog compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this context, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IV. METHODS OF TREATMENT

In particular, the compositions that may be used in treating microbial infections and cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing bacterial cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (complete blood count—CBC), or cancer cell growth or proliferation. In some embodiments, amounts of the naphthoquinones analogs used to inhibit bacterial growth or induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the naphthoquinones analogs may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

V. COMBINATION THERAPIES

It is envisioned that the naphthoquinones analogs described herein may be used in combination therapies with one or more cancer therapies or a compound, which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the naphthoquinones analogs described herein may precede or follow the other treatment by intervals ranging from minutes to weeks. One would generally ensure that a significant period of time did not expire between the times of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| A/B/A | B/A/B | B/B/A | A/A/B | B/A/A | A/B/B |
|---|---|---|---|---|---|
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; tenipo-side; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets, which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants, e.g., *Mycobacterium bovis*, *Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

VI. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH; "sulfonamide" means —S(O)$_2$NH$_2$; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "=" represents a single bond or a double bond. Thus, for example, the formula

includes

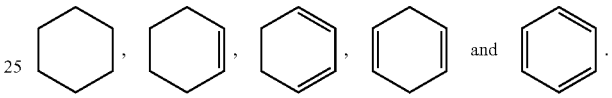

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫽" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

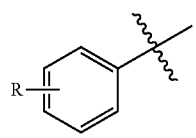

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

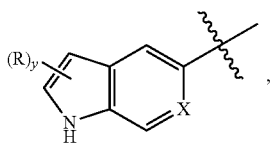

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

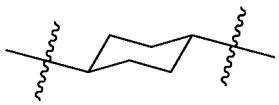 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

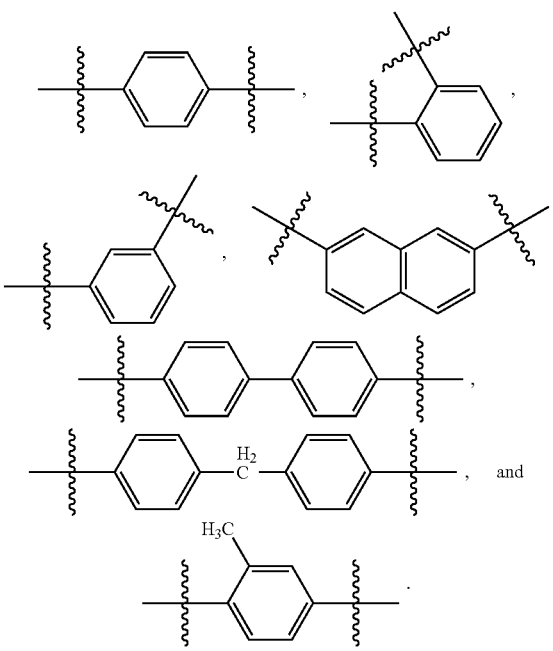

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, or aryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH (CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", and "acyloxy", when used without the "substituted" modifier, refers to groups, defined as —OR, in which R is cycloalkyl, alkenyl, alkynyl, aryl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", and "alkoxyamino" when used without the "substituted" modifier, refers to groups, defined as —NHR, in which R is cycloalkyl, alkenyl, alkynyl, aryl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose that is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Chemical Synthesis

The compounds of this disclosure with general formula I and II can be prepared based on the following schemes from commercially available starting materials or lab-prepared starting materials. These schemes show the preparation of representative compounds of this disclosure.

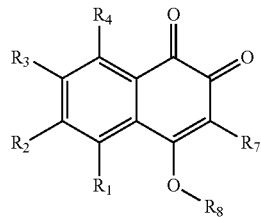

I

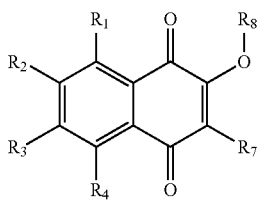

II

Compounds of general formula I and II can be synthesized from tetralone A and appropriate intermediate or commercial reagents as shown in Scheme 1.

Scheme 1

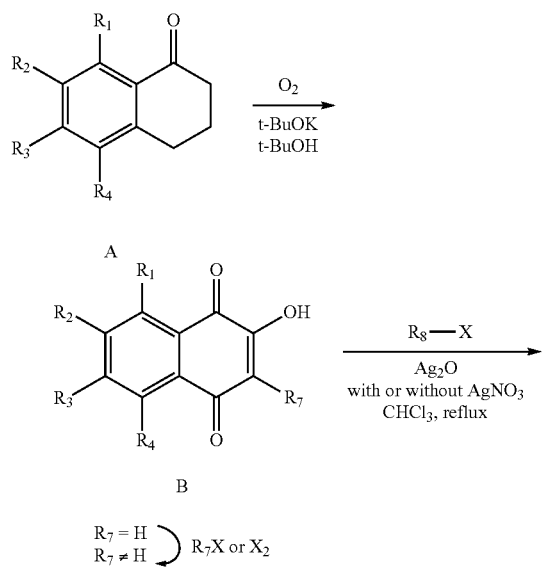

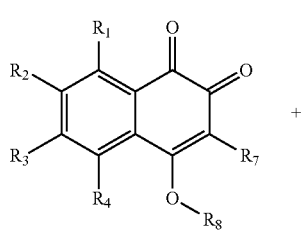

I

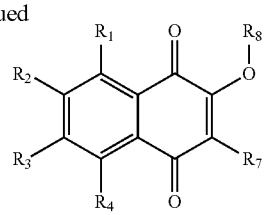

II

A. Protocol I. Synthesis of Compounds of General Formula I and II.

I.1 Synthesis of Intermediate B ($R_7$=H)

To the solution of t-BuOK (4 equivalents) in t-BuOH, ketone A (1 equivalent, commercial available or synthesized by method mentioned as following) was added in batch under oxygen atmosphere. After then the reaction mixture was stirred under oxygen atmosphere at room temperature till the TLC showed all the starting material had gone. After the mixture was poured into excess water, the mixture was washed with ethyl acetate, and then the aqueous phase was titrated with con. HCl solution until a pH 1 was obtained. Aqueous phase was extracted with ethyl acetate three times, and the organic phase was collected. After organic phase was washed with sat. $Na_2CO_3$ solution, basic aqueous phase was collected and titrated with con. HCl solution. After extraction with ethyl acetate, the organic phase was collected, dried over $MgSO_4$, and concentrated in vacuo. Desired crude product intermediate B ($R_7$=H) was afford as a dark red or orange solid.

I.2. Synthesis of Intermediate B ($R_7 \neq H$)

Under basic condition, halogenated alkane can react with intermediate B ($R_7$=H) to give a desired intermediate B ($R_7 \neq H$). Or intermediate B ($R_7$=H) can be halogenated with NXS (X=C, B, or I) or $X_2$ (X=Cl, Br, I) to give intermediate B ($R_7 \neq H$). Compound B ($R_7 \neq H$) can be purified with silica gel TCL plates or recrystallization.

I.3. Synthesis of Compounds of General Formula I and II

The mixture of intermediate B (1 equivalent), halogenated alkane (1.3-2 equivalents), and $Ag_2O$ (2 equivalents) or additional with $AgNO_3$ (1 equivalent) in chloroform refluxed till TLC showed the entire compound D is consumed. After cooled down to room temperature and going through a pad of Celite®, the mixture was concentrated, and the residue was purified with silica gel TLC plates or column chromatography to give the desired product.

Alternatively, compounds of general formula I ($R_7$=H) also can be synthesized from tetralone A and appropriate intermediate or commercial reagents as shown in Scheme 2.

Scheme 2

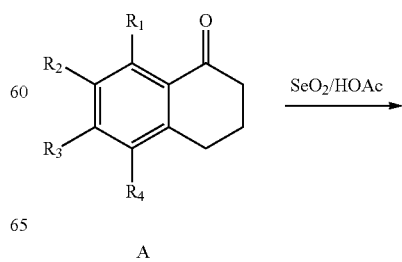

A

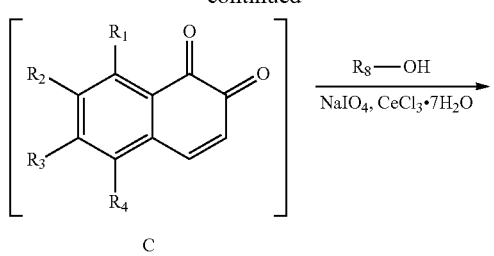

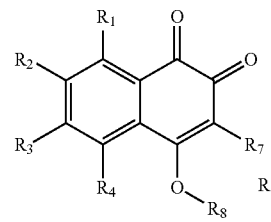

B. Protocol II. Synthesis of Compound of General Formula I (R7═H).

II.1. Synthesis of Intermediate C

The mixture of intermediate A (1 equivalent) and $SeO_2$ (2-4 equivalents) in acetic acid was stirred at 65° C. until TLC showed the entire A was consumed. After cooled down to room temperature, and filtered through a pad of Celite®, the mixture was diluted with water and extracted with ethyl acetate. The organic phase was collected and dried over $MgSO_4$. The residue afforded after concentration was purified through silica gel column chromatography or directly used in the next step.

II.2. Synthesis of Compound of General Formula I

Intermediate C (1 equivalent) from II.1 was dissolved in $R_8$—OH and Nitrile solution (2:1), and the mixture was mixed with $CeCl_3.7H_2O$ (1 equivalent) in minimum water. Subsequently, $NaIO_4$ (1 equivalent) was added in one portion. After then, the mixture was stirred at room temperature till TLC showed all the starting material disappeared. The reaction mixture was diluted with EtOAc, washed with $H_2O$ and brine in sequence, and dried over $Na_2SO_4$. After concentration, the crude product was purified through TLC plates.

Alternatively, intermediate B (R7═H) also can be synthesized from naphthaquinone D and appropriate intermediate or commercial reagents as shown in Scheme 3.

Scheme 3

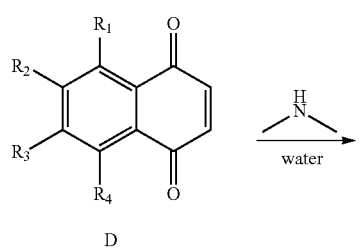

C. Protocol III. Synthesis of Intermediate B (R7═H)

III.1. Synthesis of Intermediate E

Dimethyl amine solution (40%, 2 equivalents) was added to the mixture of naphthaquinone D (1 equivalent) in water. After stirring at room temperature for 2 hours, the mixture was filtered and washed with EtOAc. The organic phase was collected and dried over $MgSO_4$. After filtration and concentration the residue afforded was purified thought silica gel chromatography to give the desired product intermediate E.

III.2. Synthesis of Intermediate B

The solution of Intermediate E in con. HCl refluxed until TLC showed the entire starting material was consumed. After cooled down to room temperature, the mixture was diluted with excess water, and extracted with DCM. After dried over $MgSO_4$, the organic phase was concentrated to afford the desire product intermediate B.

The compounds of this disclosure with general formula III and IV can be synthesized based on the following schemes from commercially available starting materials or lab-prepared starting materials. These schemes show the preparation of representative compounds of this disclosure.

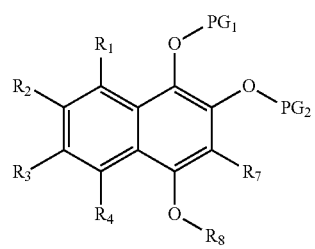

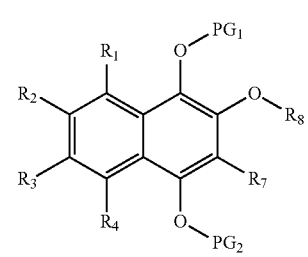

Compounds of general formula III and IV can be synthesized from compounds of general formula I and II and appropriate intermediate or commercial reagents as shown in Scheme 4.

Scheme 4

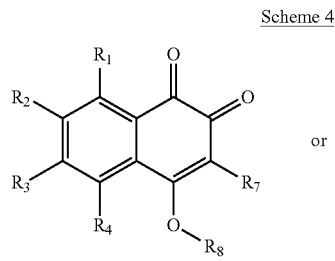

I or

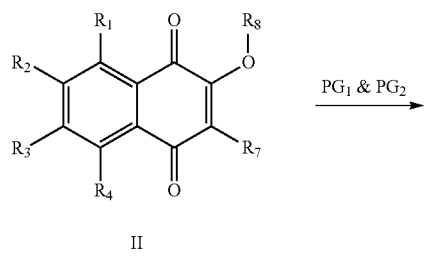

II

PG₁ & PG₂ →

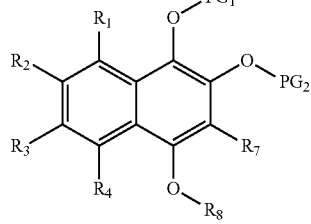

III or

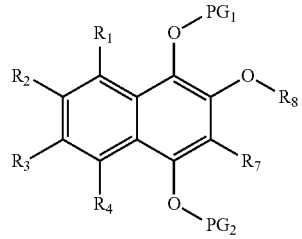

IV

There is no particular limit to the method for preparing a pro-drug, which is an active ingredient of the pro-drug composition, so it can be appropriately prepared by a conventional method known in the art. For example, compounds of formula I or II is reduced into relative hydroquinone form using zinc (Zn) powder, followed by induction of first acetylation and then second acetylation to thereby the pro-drug compound of formula III or IV as shown in Scheme 5.

Scheme 5

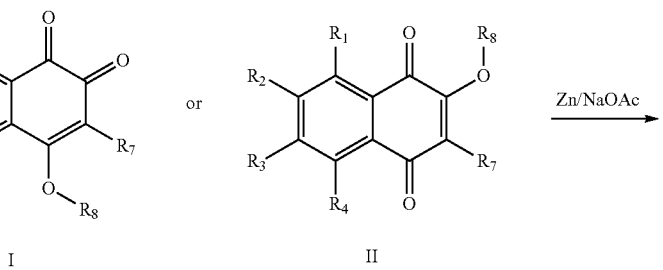

Zn/NaOAc →

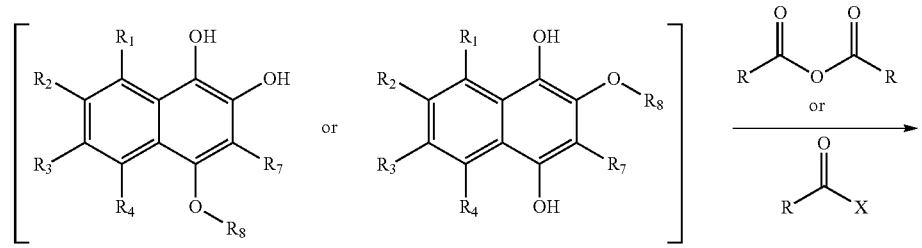

-continued

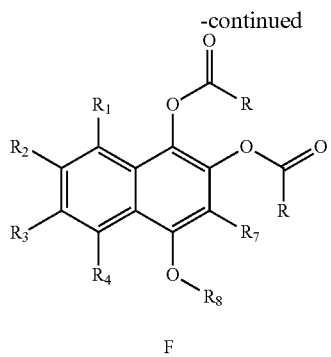

F

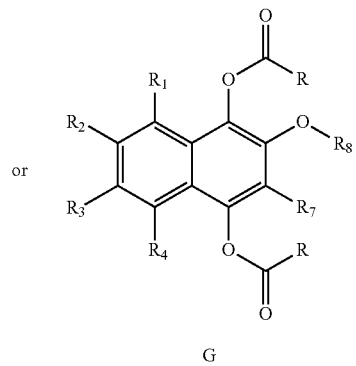

G

COMPOUNDS

Compound 1:
7-bromo-4-isopropoxynaphthalene-1,2-dione

1.1. Synthesis of 7-bromo-2-hydroxynaphthalene-1,4-dione

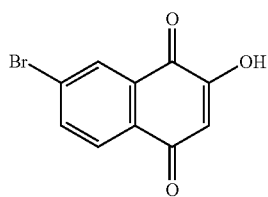 [SMILES: O=C1C=C(O)C(=O)c2cc(Br)ccc21]

The procedure is the similar as described in I.1 of Protocol I. $^1$H NMR (400 MHz, DMSO-d$_6$) δ 8.04 (d, J=2.1 Hz, 2H), 8.03 (d, J=8.1 Hz, 2.1 Hz, 1H), 7.84 (d, J=8.1 Hz, 1H), 6.16 (s, 1H).

1.2. Synthesis of 7-bromo-4-isopropoxynaphthalene-1,2-dione

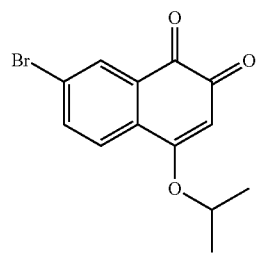

The procedure is the similar as described in 1.2 of Protocol I. $^1$H NMR (400 MHz, chloroform-d): δ 8.20 (d, J=2.1 Hz, 1H), 7.79 (dd, J=8.4, 2.1 Hz, 1H), 7.72 (d, J=8.4 Hz, 1H), 5.96 (d, J=0.7 Hz, 1H), 4.81-4.63 (m, 1H), 1.48 (d, J=6.1 Hz, 6H). $^{13}$C NMR (101 MHz, chloroform-d): δ 178.7, 178.7, 166.2, 137.7, 131.8, 131.7, 131.6, 131.2, 126.5, 126.5, 104.1, 73.4, 21.5.

Compound 2.
7-bromo-4-(cyclohexyloxy)naphthalene-1,2-dione

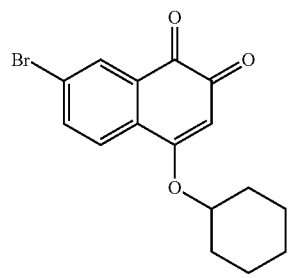

The procedure is the similar as described in 1.2 of Protocol I. $^1$H NMR (400 MHz, chloroform-d) δ 8.22 (t, J=1.8 Hz, 1H), 7.81 (dt, J=8.5, 1.7 Hz, 1H), 7.75 (dd, J=8.4, 1.4 Hz, 1H), 5.99 (d, J=1.4 Hz, 1H), 4.49 (dt, J=8.6, 4.4 Hz, 1H), 2.04 (td, J=8.7, 8.0, 4.3 Hz, 2H), 1.83 (dq, J=8.0, 4.0 Hz, 2H), 1.71 (dtd, J=12.9, 8.9, 3.9 Hz, 2H), 1.61 (dt, J=12.8, 4.8 Hz, 2H), 1.46 (dq, J=18.1, 8.0, 6.8 Hz, 4H). $^{13}$C NMR (101 MHz, CDCl$_3$) δ 178.7229, 178.7091, 166.1259, 137.6774, 131.7874, 131.7591, 131.6656, 131.3114, 126.5035, 126.4064, 104.1315, 78.2056, 30.9918, 25.1785, 23.3503.

Compound 3. 6-fluoro-3-hydroxy-2-(3-methylbut-2-en-1-yl)naphthalene-1,4-dione

3.1. Synthesis of 7-fluoro-2-hydroxynaphthalene-1,4-dione

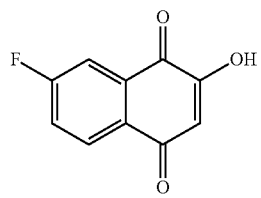 [SMILES: O=C1C=C(O)C(=O)c2cc(F)ccc21]

The procedure is the similar as described in I.1 of protocol I. $^1$H NMR (400 MHz, DMSO-d$_6$) δ 11.86 (s, 1H), 8.05-8.02 (m, 1H), 8.01 (d, J=2.1 Hz, 1H), 7.83 (d, J=8.0 Hz, 1H), 6.16 (s, 1H).

3.2. Synthesis of 7-fluoro-4-isopropoxynaphthalene-1,2-dione

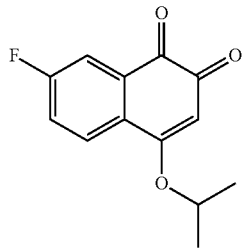

The procedure is the similar as described in 1.2 of Protocol I. $^1$H NMR (400 MHz, chloroform-d): δ 7.88 (dd, J=8.7, 5.1 Hz, 1H), 7.75 (dd, J=8.2, 2.7 Hz, 1H), 7.35 (ddd, J=8.7, 7.8, 2.8 Hz, 1H), 5.91 (d, J=0.7 Hz, 1H), 4.73 (heptd, J=6.1, 0.7 Hz, 1H), 1.48 (d, J=6.1 Hz, 6H). $^{13}$C NMR (101 MHz, Chloroform-d): δ 179.2, 178.6, 166.3, 165.8, 163.3, 132.8, 132.8, 128.8, 128.8, 127.5, 127.4, 121.8, 121.6, 121.6, 115.9, 115.7, 103.2, 73.3, 21.5.

Compound 4. 6-chloro-3-hydroxy-2-(3-methylbut-2-en-1-yl)naphthalene-1,4-dione

4.1. Synthesis of 7-chloro-2-hydroxynaphthalene-1,4-dione

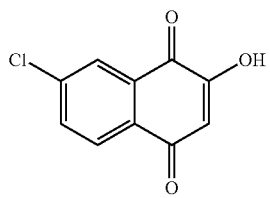 [SMILES: O=C1C=C(O)C(=O)c2cc(Cl)ccc21]

The procedure is the similar as described in 1.1 of Protocol I. $^1$H NMR (400 MHz, DMSO-d$_6$) δ 11.88 (s, 1H), 7.98-7.85 (m, 3H), 6.16 (s, 1H).

4.2. Synthesis of 7-chloro-4-isopropoxynaphthalene-1,2-dione

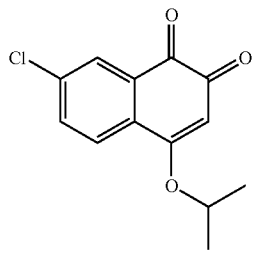

The procedure is the similar as described in 1.2 of Protocol I. $^1$H NMR (400 MHz, chloroform-d): δ 8.13-7.98 (m, 1H), 7.81 (d, J=8.4 Hz, 1H), 7.63 (dd, J=8.4, 2.3 Hz, 1H), 5.95 (d, J=0.7 Hz, 1H), 4.73 (pd, J=6.1, 0.7 Hz, 1H), 1.48 (d, J=6.1 Hz, 6H). $^{13}$C NMR (101 MHz, chloroform-d): δ 178.8, 178.7, 166.1, 138.3, 134.7, 131.6, 130.8, 128.8, 126.4, 103.9, 73.3, 21.5.

Compound 5. 7-chloro-4-(cyclohexyloxy)naphthalene-1,2-dione

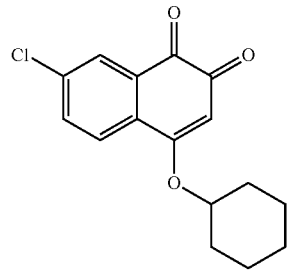 [SMILES: O=C1C=C(OC2CCCCC2)c2ccc(Cl)cc2C1=O]

The procedure is the similar as described in 1.2 of Protocol I. $^1$H NMR (400 MHz, chloroform-d) δ 8.07 (d, J=2.3 Hz, 1H), 7.83 (d, J=8.4 Hz, 1H), 7.64 (dd, J=8.4, 2.3 Hz, 1H), 5.98 (s, 1H), 4.49 (dq, J=8.1, 4.1, 3.5 Hz, 1H), 2.11-1.99 (m, 2H), 1.83 (s, 2H), 1.78-1.66 (m, 2H), 1.66-1.58 (m, 2H), 1.53-1.37 (m, 4H).

Compound 6. 5-chloro-4-isopropoxynaphthalene-1,2-dione

6.1. Synthesis of 5-nitro-3,4-dihydronaphthalen-1(2H)-one

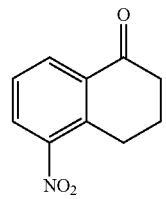

To the solution of 3,4-dihydronaphthalen-1(2H)-one (20 g, 137 mmol) in con. H$_2$SO$_4$ (300 mL), the solution of HNO$_3$ (8.6 mL, 144 mmol, 63%) in con. H$_2$SO$_4$ (50 mL) was dropped in while the reaction maintaining below 5° C., and the solution was stirred at 0° C. for 1 hour. And then the solution was poured into ice-water (2 L), and the mixture was stirred at room temperature for 30 mins. After filtration, the solid afforded was washed with water, and dried in vacuo. After purification with silica gel chromatography (Hex-EtOAc as a gradient eluent), white solid (4.1 g, 15.7%) was afforded as an off-white solid.

6.2. Synthesis of 5-amino-3,4-dihydronaphthalen-1(2H)-one

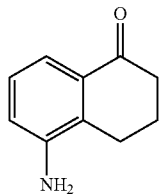

The mixture of 5-nitro-3,4-dihydronaphthalen-1(2H)-one (3.5 g, 18.3 mmol) and SnCl$_2$ (10.4 g, 54.9 mmol) in EtOH (50 mL) reflux for 0.5 hour. After cooled down to room temperature, the mixture was poured into excess water. As soon as the mixture was treated with sat. NaHCO$_3$ solution, an orange precipitate appeared. After pH was adjusted to 8, the mixture was filtered through a pad of Celite®, and washed with water and EtOAc in sequence. The filtrate was extracted with EtOAc, and the organic phase was collected and evaporated. After flash silica gel chromatography, desired product as a pale yellow solid was afforded (2.26 g, 77%).

6.3. Synthesis of 5-chloro-3,4-dihydronaphthalen-1(2H)-one

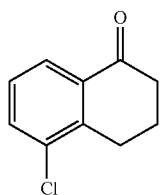 [SMILES: O=C1CCCc2c(Cl)cccc21]

5-amino-3,4-dihydronaphthalen-1(2H)-one (1 g, 6.2 mmol) in HCl (36%, 2 mL) and EtOH (8 mL) at 0° C. was treated with an aqueous solution of NaNO$_2$ (0.582 g, 8.4 mmol in 1 mL water for 15 min. This mixture was added to a solution of CuCl (0.3 g, 3.1 mmol) in HCl (36%, 10 mL) at 95° C. and kept at this temperature for 15 min. The solution was cooled down to room temperature, diluted with water, and extracted with EtOAc. The organic phase was collected, washed with sat. NaHCO$_3$, dried over MgSO$_4$, and purified by column chromatography with 40-50% EtOAc:Hex on silica gel. Desired compound was afforded. (0.7 g, 62%). $^1$H NMR (400 MHz, chloroform-d) δ 7.53 (dd, J=7.8, 1.2 Hz, 1H), 7.14 (tt, J=7.8, 0.7 Hz, 1H), 6.88 (dd, J=7.8, 1.2 Hz, 1H), 3.70 (s, 2H), 2.69 (t, J=6.2 Hz, 2H), 2.66-2.60 (m, 2H), 2.30-2.07 (m, 2H).

6.4. Synthesis of 5-chloro-2-hydroxynaphthalene-1,4-dione

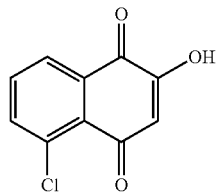

The procedure is the similar as described in I.1 of Protocol I. $^1$H NMR (400 MHz, DMSO-d$_6$) δ 11.64 (s, 1H), 8.02 (dd, J=7.6, 1.3 Hz, 1H), 7.86 (dd, J=8.1, 1.3 Hz, 1H), 7.76-7.71 (m, 1H), 6.13 (s, 1H).

6.5. Synthesis of 5-chloro-4-isopropoxynaphthalene-1,2-dione

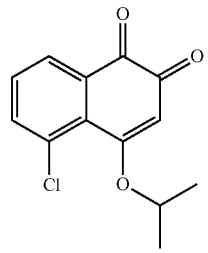 [SMILES: CC(C)OC1=CC(=O)C(=O)c2cccc(Cl)c21]

The procedure is the similar as described in 1.2 of Protocol I. $^1$H NMR (400 MHz, chloroform-d): δ 7.88 (dd, J=6.6, 2.5 Hz, 1H), 7.59-7.53 (m, 2H), 5.97 (d, J=0.7 Hz, 1H), 4.73 (pd, J=6.1, 0.7 Hz, 1H), 1.48 (d, J=6.1 Hz, 6H). $^{13}$C NMR (101 MHz, chloroform-d): δ 178.8, 178.6, 165.5, 137.0, 135.0, 134.9, 134.3, 127.2, 124.0, 103.9, 73.3, 21.5.

Compound 7. 4-isopropoxy-5-nitronaphthalene-1,2-dione

7.1. Synthesis of 5-nitronaphthalene-1,2-dione

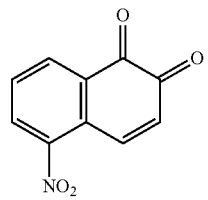 [SMILES: O=C1C=Cc2c(cccc2[N+](=O)[O-])C1=O]

The procedure is the similar as described in II.1 of Protocol II. $^1$H NMR (400 MHz, chloroform-d) δ 8.38 (ddd, J=7.7, 1.4, 0.7 Hz, 1H), 8.18 (dd, J=8.2, 1.4 Hz, 1H), 8.09 (dd, J=10.8, 0.7 Hz, 1H), 7.70 (t, J=8.0 Hz, 1H), 6.64 (d, J=10.7 Hz, 1H).

7.2. Synthesis of 4-isopropoxy-5-nitronaphthalene-1,2-dione

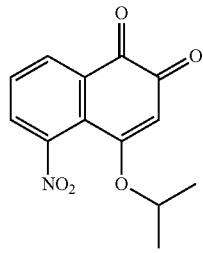 [SMILES: CC(C)OC1=CC(=O)C(=O)c2cccc([N+](=O)[O-])c21]

The procedure is the similar as described in 11.2 of Protocol II. $^1$H NMR (400 MHz, chloroform-d) δ 8.28 (ddd, J=7.6, 1.5, 0.7 Hz, 1H), 7.74-7.68 (m, 1H), 7.64 (ddd, J=8.0, 1.6, 0.8 Hz, 1H), 6.01 (d, J=0.8 Hz, 1H), 4.69 (hept, J=6.2 Hz, 1H), 1.41 (dd, J=6.1, 0.8 Hz, 6H). $^{13}$C NMR (101 MHz, chloroform-d) δ 177.96, 177.74, 163.77, 132.32, 131.71, 130.88, 129.03, 123.39, 105.43, 75.16, 20.74. LC-MS (M+H$^+$)=262.1

Compound 8. 4-isopropoxy-6,7-dimethoxynaphthalene-1,2-dione

8.1. Synthesis of 2-hydroxy-6,7-dimethoxynaphthalene-1,4-dione

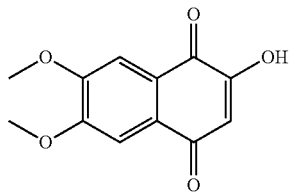 [SMILES: COc1cc2c(cc1OC)C(=O)C(O)=CC2=O]

The procedure is the similar as described in I.1 of Protocol I. $^1$H NMR (400 MHz, DMSO-d$_6$) δ 11.51 (s, 1H), 7.41 (s, 1H), 7.37 (s, 1H), 6.04 (s, 1H), 3.91 (s, 3H), 3.90 (s, 3H).

8.2. Synthesis of 4-isopropoxy-6,7-dimethoxynaphthalene-1,2-dione

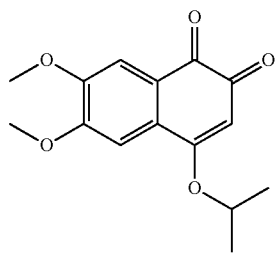 [SMILES: COc1cc2c(cc1OC)C(OC(C)C)=CC(=O)C2=O]

The procedure is the similar as described in 1.2 of Protocol I. $^1$H NMR (400 MHz, chloroform-d): δ 7.57 (s, 1H), 7.26 (s, 1H), 5.81 (d, J=0.7 Hz, 1H), 4.71 (pd, J=6.0, 0.8 Hz, 1H), 4.02 (s, 3H), 3.98 (s, 3H), 1.48 (d, J=6.1 Hz, 6H). $^{13}$C NMR (101 MHz, chloroform-d): δ 180.0, 178.5, 166.7, 154.3, 151.2, 127.4, 124.7, 110.9, 106.8, 102.4, 73.0, 56.4, 56.3, 21.6.

Compound 9. 8-isopropoxynaphtho[2,3-d][1,3]dioxole-5,6-dione

9.1. Synthesis of 7,8-dihydronaphtho[2,3-d][1,3]dioxol-5(6H)-one

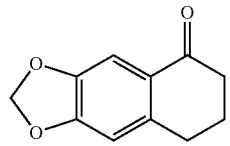 [SMILES: O=C1CCCc2cc3c(cc21)OCO3]

The mixture of 6,7-dihydroxy-3,4-dihydronaphthalen-1(2H)-one (1 equivalent), dibromomethane (1.2 equivalent), and KF (8 equivalents) in DMF was heated under 140° C. for 6 hours. After cooled down to room temperature, the mixture was washed with water and extracted with ethyl acetate. The organic phase was collected, washed with Na$_2$CO$_3$ solution and brine in sequence, and dried over MgSO$_4$. After concentration in vacuo, the residue was purified with silica gel column chromatography to afford off-white solid. $^1$H NMR (400 MHz, Chloroform-d) δ 7.47 (s, 1H), 6.66 (s, 1H), 5.99 (s, 2H), 2.87 (t, J=6.1 Hz, 2H), 2.59 (dd, J=7.2, 5.8 Hz, 2H), 2.09 (tt, J=6.8, 5.6 Hz, 2H).

9.2. Synthesis of 6-hydroxynaphtho[2,3-d][1,3]dioxole-5,8-dione

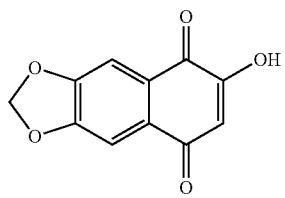 [SMILES: O=C1C=C(O)C(=O)c2cc3c(cc21)OCO3]

The procedure is the similar as described in I.1 of Protocol I. 1H NMR (400 MHz, DMSO-d$_6$) δ 7.38 (s, 1H), 7.32 (s, 1H), 6.22 (s, 2H), 6.04 (s, 1H).

9.3. Synthesis of 8-isopropoxynaphtho[2,3-d][1,3]dioxole-5,6-dione

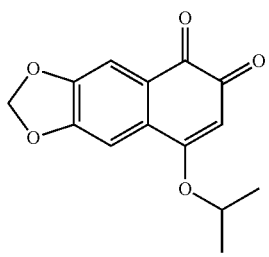 [SMILES: CC(C)OC1=CC(=O)C(=O)c2cc3c(cc21)OCO3]

The procedure is the similar as described in 1.2 of Protocol I. $^1$H NMR (400 MHz, chloroform-d): δ 7.53 (s, 1H), 7.28 (s, 1H), 6.12 (s, 2H), 5.82 (d, J=0.7 Hz, 1H), 4.69 (hept, J=6.0 Hz, 1H), 1.46 (d, J=6.1 Hz, 6H). $^{13}$C NMR (101 MHz, chloroform-d): δ 179.7, 177.9, 166.4, 153.2, 150.2, 129.7, 126.8, 108.7, 105.1, 102.6, 102.2, 73.0, 21.6.

Compound 10.
4-isopropoxy-5,7-dimethylnaphthalene-1,2-dione 10.1 Synthesis of
2-hydroxy-5,7-dimethylnaphthalene-1,4-dione

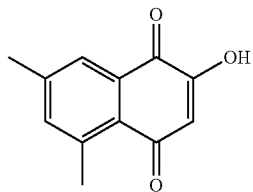

Same as described in 1.1 of Protocol I. $^1$H NMR (400 MHz, DMSO-d$_6$) δ 11.34 (s, 1H), 7.72 (d, J=1.9 Hz, 1H), 7.48-7.43 (m, 1H), 6.05 (s, 1H), 2.60 (s, 3H), 2.38 (s, 3H).

10.2.
4-isopropoxy-5,7-dimethylnaphthalene-1,2-dione

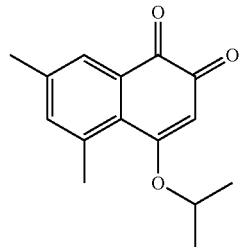 [SMILES: Cc1cc(C)c2c(c1)C(=O)C(=O)C=C2OC(C)C]

The procedure is the similar as described in 1.2 of Protocol I. $^1$H NMR (400 MHz, chloroform-d): δ 7.86 (dd, J=1.4, 0.7 Hz, 1H), 7.26 (dd, J=1.4, 0.7 Hz, 1H), 5.90 (s, 1H), 4.74 (pd, J=6.1, 0.8 Hz, 1H), 2.61 (s, 3H), 2.37 (s, 3H), 1.50 (d, J=6.1 Hz, 6H). $^{13}$C NMR (101 MHz, chloroform-d): δ 180.9, 179.4, 171.2, 141.4, 140.5, 138.5, 132.0, 129.0, 127.3, 103.3, 73.3, 24.6, 21.7, 21.0.

Compound 11.
3-bromo-4-isopropoxynaphthalene-1,2-dione 11.1. Synthesis of
2-bromo-3-hydroxynaphthalene-1,4-dione

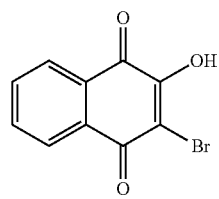 [SMILES: O=C1C(O)=C(Br)C(=O)c2ccccc21]

To the mixture of 2-hydroxynaphthalene-1,4-dione (1 equivalent) in AcOH, Br$_2$ in AcOH was dropped in under ice-bath. And then the mixture was stirred at room temperature for 3 hours. After dilution with water, the mixture was extracted with EtOAc, and washed with sat. NaHCO$_3$ solution. Aqueous phase was collected and treated with HCl to adjust pH value to 1. A yellow precipitate was filtered and washed with water. After concentration in vacuo, a yellow solid was afforded. $^1$H NMR (400 MHz, chloroform-d) δ 8.24-8.19 (m, 1H), 8.17-8.11 (m, 1H), 7.78 (dtd, J=22.1, 7.5, 1.4 Hz, 2H). $^{13}$C NMR (101 MHz, CDCl$_3$) δ 178.7766, 178.0695, 155.2610, 135.4327, 133.6694, 132.1760, 128.7571, 127.8597, 127.0525, 111.4378.

11.2. Synthesis of
3-bromo-4-isopropoxynaphthalene-1,2-dione

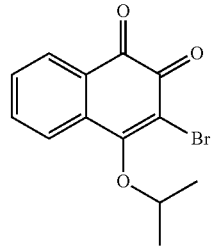 [SMILES: CC(C)OC1=C(Br)C(=O)C(=O)c2ccccc21]

The procedure is the similar as described in 1.2 of Protocol I. $^1$H NMR (400 MHz, chloroform-d) δ 8.06 (ddd, J=7.6, 1.5, 0.5 Hz, 1H), 7.83 (ddd, J=7.9, 1.2, 0.5 Hz, 1H), 7.70 (td, J=7.7, 1.4 Hz, 1H), 7.57 (td, J=7.6, 1.2 Hz, 1H), 5.37 (hept, J=6.1 Hz, 1H), 1.47 (d, J=6.2 Hz, 6H). $^{13}$C NMR (101 MHz, CDCl$_3$) δ 177.0793, 175.1474, 166.1346, 135.6252, 134.4578, 131.5613, 129.7172, 128.9767, 125.9120, 110.6242, 79.0284, 22.8761.

Compound 12.
2-bromo-3-isopropoxynaphthalene-1,4-dione

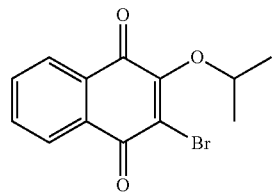 [SMILES: CC(C)OC1=C(Br)C(=O)c2ccccc2C1=O]

The procedure is the similar as described in 1.2 of Protocol I. $^1$H NMR (400 MHz, chloroform-d) δ 8.15 (ddd, J=5.7, 3.3, 0.5 Hz, 1H), 8.08 (ddd, J=5.8, 3.3, 0.5 Hz, 1H), 7.74 (dd, J=5.7, 3.3 Hz, 2H), 5.29 (hept, J=6.1 Hz, 1H), 1.43 (d, J=6.2 Hz, 6H). $^{13}$C NMR (101 MHz, CDCl$_3$) δ 179.3856, 178.7890, 158.7658, 134.2007, 133.8032, 131.0850, 130.8872, 127.2758, 126.9634, 124.8343, 78.5233, 23.2147.

Compound 13.
3-chloro-4-isopropoxynaphthalene-1,2-dione

13.1. Synthesis of 2-chloro-3-hydroxynaphthalene-1,4-dione

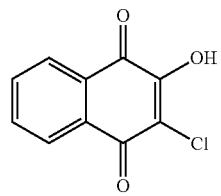 [SMILES: O=C1C(O)=C(Cl)C(=O)c2ccccc21]

To the concentrated solution of 2-hydroxynaphthalene-1,4-dione (1 equivalent) in CHCl$_3$, the solution of NCS (1.5 equivalents) in CHCl$_3$ was dropped in, and the mixture was stirred at room temperature for one day. After washed with saturated NaHCO$_3$ solution, the aqueous phase was treated with HCl solution to adjust pH=3. After extraction with EtOAc, the organic phase was collected and dried over Na$_2$SO$_4$. The residue afforded is purified through silica gel chromatographic plates to afford bolarious solid. $^1$H NMR (400 MHz, DMSO-d$_6$) δ 7.93 (dd, J=7.6, 1.3 Hz, 1H), 7.87 (dd, J=7.5, 1.4 Hz, 1H), 7.73 (td, J=7.5, 1.3 Hz, 1H), 7.63 (td, J=7.5, 1.4 Hz, 1H).

13.2. Synthesis of 2-bromo-3-isopropoxynaphthalene-1,4-dione

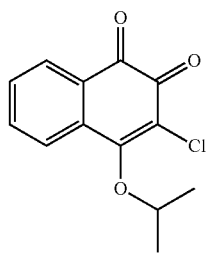 [SMILES: CC(C)OC1=C(Cl)C(=O)C(=O)c2ccccc21]

The procedure is the similar as described in 1.2 of Protocol I. $^1$H NMR (400 MHz, chloroform-d) δ 8.09 (ddt, J=7.7, 1.3, 0.6 Hz, 1H), 7.86 (ddt, J=7.9, 1.2, 0.5 Hz, 1H), 7.77-7.66 (m, 1H), 7.56 (tdd, J=7.5, 1.2, 0.6 Hz, 1H), 5.45 (pd, J=6.1, 0.6 Hz, 1H), 1.49 (dd, J=6.1, 0.6 Hz, 6H). $^{13}$C NMR (101 MHz, CDCl$_3$) δ 177.4813, 175.0013, 163.4005, 135.6130, 134.0299, 131.4245, 129.6027, 128.9571, 125.8817, 117.8313, 78.6064, 22.9389, 22.9189.

Compound 14.
8-chloro-4-isopropoxynaphthalene-1,2-dione

14.1. Synthesis of N-(8-oxo-5,6,7,8-tetrahydronaphthalen-1-yl)acetamide

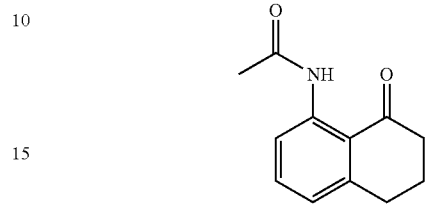

To the solution of Ac$_2$O (2 equivalents) in EtOH under ice-bath, the solution of 5,6,7,8-tetrahydronaphthalen-1-amine (1 equivalent) in EtOH was dropped in, and the mixture was stirred at room temperature for over 18 hours. After concentration, a white solid was afforded, which is dissolved in acetone-MgSO$_4$ 1.5M aqueous solution (7:1). KMnO$_4$ was added in portion-wise to the mixture, and the mixture was stirred at room temperature for over 18 hours. After filtration through a pad of Celite®, the filtrate was concentrated and dissolved in CHCl$_3$. After washed with excess water and brine, the organic phase was collected, dried over Na$_2$SO$_4$ and concentrated in vacuum. The residue was purified through flash silica gel column chromatography to give an off-white solid. $^1$H NMR (400 MHz, Chloroform-d) δ 12.15 (s, 1H), 8.59 (ddt, J=8.4, 1.2, 0.6 Hz, 1H), 7.49-7.39 (m, 1H), 6.92 (dq, J=7.5, 1.0 Hz, 1H), 2.97 (td, J=6.1, 1.0 Hz, 2H), 2.69 (ddd, J=7.3, 5.7, 0.7 Hz, 2H), 2.23 (s, 3H), 2.14-2.03 (m, 2H).

14.2. Synthesis of 8-amino-3,4-dihydronaphthalen-1(2H)-one

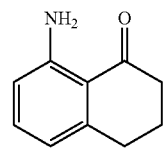 [SMILES: Nc1cccc2c1C(=O)CCC2]

The mixture of N-(8-oxo-5,6,7,8-tetrahydronaphthalen-1-yl)acetamide was heated in 6M HCl solution at 90° C. for 3 hours. After cooled down to room temperature, the solution was titrated with Na$_2$CO$_3$ in portions followed by addition of 2M NaOH until the mixture was at pH=8. The aqueous phase was extracted with EtOAc and the organic fractions were combined, washed with brine, dried, filtered, and concentrated to afford as a brown solid. $^1$H NMR (400 MHz, chloroform-d) δ 7.14 (t, J=7.8 Hz, 1H), 6.46 (t, J=8.2 Hz, 3H), 2.87 (t, J=6.1 Hz, 2H), 2.62 (t, J=6.5 Hz, 2H), 2.03 (p, J=6.4 Hz, 2H).

14.3. Synthesis of 8-chloro-3,4-dihydronaphthalen-1(2H)-one

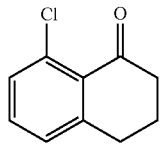

The procedure is the similar as described in 6.3 of Example 6. $^1$H NMR (400 MHz, chloroform-d) δ 7.34-7.30 (m, 1H), 7.19-7.13 (m, OH), 2.97 (t, J=6.1 Hz, 1H), 2.78-2.65 (m, 1H), 2.10 (p, J=6.5 Hz, 1H).

14.4. Synthesis of 8-chloro-2-hydroxynaphthalene-1,4-dione 8-chloro-2-hydroxynaphthalene-1,4-dione

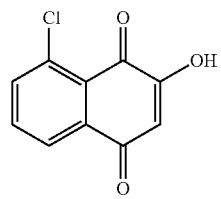 [SMILES: O=C1C=C(O)C(=O)c2c(Cl)cccc21]

The procedure is the similar as described in I.1 of Protocol I. $^1$H NMR (400 MHz, DMSO-d$_6$) δ 7.96 (dd, J=7.4, 1.5 Hz, 1H), 7.82 (dd, J=8.1, 1.5 Hz, 1H), 7.80-7.74 (m, 1H), 6.13 (s, 1H).

14.5. Synthesis of 8-chloro-4-isopropoxynaphthalene-1,2-dione

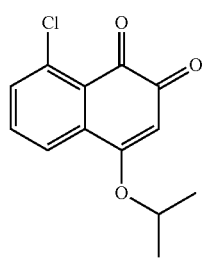 [SMILES: CC(C)OC1=CC(=O)C(=O)c2c(Cl)cccc21]

The procedure is the similar as described in 1.2 of Protocol I. $^1$H NMR (400 MHz, chloroform-d): δ 7.88 (dd, J=6.6, 2.5 Hz, 1H), 7.59-7.53 (m, 2H), 5.97 (d, J=0.7 Hz, 1H), 4.73 (pd, J=6.1, 0.7 Hz, 1H), 1.48 (d, J=6.1 Hz, 6H). $^{13}$C NMR (101 MHz, chloroform-d): δ 178.8, 178.6, 165.5, 137.0, 135.0, 134.9, 134.3, 127.2, 124.0, 103.9, 73.3, 21.5.

Compound 15. 8-chloro-2-isopropoxynaphthalene-1,4-dione

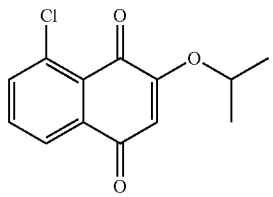 [SMILES: CC(C)OC1=CC(=O)c2cccc(Cl)c2C1=O]

The procedure is the similar as described in 1.2 of Protocol I. $^1$H NMR (400 MHz, chloroform-d) δ 8.08 (dd, J=7.6, 1.4 Hz, 1H), 7.70 (dd, J=8.0, 1.4 Hz, 1H), 7.61 (t, J=7.8 Hz, 1H), 6.12 (d, J=0.7 Hz, 1H), 4.67-4.44 (m, 1H), 1.45 (d, J=6.1 Hz, 6H). $^{13}$C NMR (101 MHz, CDCl$_3$) δ 183.6480, 178.5546, 159.0970, 136.7525, 134.8381, 134.5259, 133.8281, 127.3533, 125.5317, 108.9481, 72.7769, 21.1460.

Example 16. 8-chloro-4-(cyclohexyloxy)naphthalene-1,2-dione

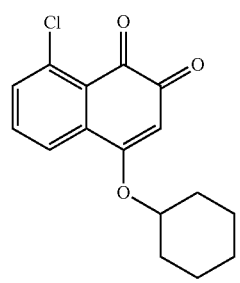 [SMILES: O=C1C=C(OC2CCCCC2)c2cccc(Cl)c2C1=O]

The procedure is the similar as described in 1.2 of Protocol I. $^1$H NMR (400 MHz, chloroform-d) δ 7.94-7.84 (m, 1H), 7.68-7.48 (m, 2H), 5.99 (s, 1H), 4.49 (ddt, J=12.1, 8.1, 3.6 Hz, 1H), 2.04 (dq, J=12.1, 3.9 Hz, 2H), 1.90-1.78 (m, 2H), 1.72 (dtd, J=12.5, 8.9, 3.6 Hz, 2H), 1.66-1.58 (m, 1H), 1.46 (m, 3H). $^{13}$C NMR (101 MHz, CDCl$_3$) δ 178.8513, 178.6930, 165.4963, 137.0038, 135.1567, 134.9147, 134.2821, 123.9793, 103.9215, 77.1882, 30.9528, 25.1990, 23.3316.

Compound 17. N-(5-isopropoxy-7,8-dioxo-7,8-dihydronaphthalen-1-yl)-4-methylbenzenesulfonamide

17.1. Synthesis of 4-methyl-N-(8-oxo-5,6,7,8-tetrahydronaphthalen-1-yl)benzenesulfonamide

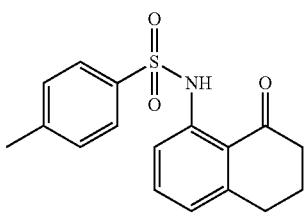 [SMILES: Cc1ccc(S(=O)(=O)Nc2cccc3c2C(=O)CCC3)cc1]

The solid 8-amino-3,4-dihydronaphthalen-1(2H)-one (1 equivalent) was dissolved in pyridine followed by TsCl (1.45 equivalents) dropped in. The mixture was stirred at room temperature for 1 hour, and then treated with excess water. A pale pink precipitate appeared. After filtration and washed with water, nearly quantitative 4-methyl-N-(8-oxo-5,6,7,8-tetrahydronaphthalen-1-yl)benzenesulfonamide was afforded. $^1$H NMR (400 MHz, chloroform-d) δ 12.01 (s, 1H), 7.81-7.73 (m, 2H), 7.51-7.46 (m, 1H), 7.32 (dd, J=8.4, 7.5 Hz, 1H), 7.25-7.21 (m, 2H), 6.84 (dd, J=7.6, 1.0 Hz, 1H), 2.89 (t, J=6.0 Hz, 2H), 2.68-2.58 (m, 2H), 2.37 (s, 2H), 2.02 (tt, J=6.9, 5.6 Hz, 2H).

17.2. Synthesis of N-(7-hydroxy-5,8-dioxo-5,8-dihydronaphthalen-1-yl)-4-methylbenzenesulfonamide

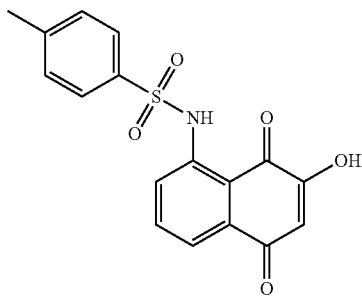 [SMILES: Cc1ccc(S(=O)(=O)Nc2cccc3c2C(=O)C(O)=CC3=O)cc1]

The procedure is the similar as described in I.1 of protocol I. $^1$H NMR (400 MHz, DMSO-$d_6$) δ 11.82 (s, 1H), 11.45 (s, 1H), 7.85-7.79 (m, 2H), 7.74-7.70 (m, 2H), 7.59 (dd, J=5.7, 3.0 Hz, 1H), 7.39 (d, J=8.2 Hz, 2H), 6.10 (s, 1H), 2.33 (s, 3H).

17.3. Synthesis of N-(5-isopropoxy-7,8-dioxo-7,8-dihydronaphthalen-1-yl)-4-methylbenzenesulfonamide

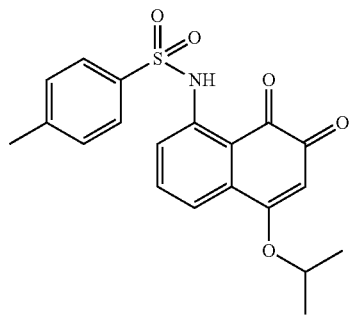 [SMILES: Cc1ccc(S(=O)(=O)Nc2cccc3c2C(=O)C(=O)C=C3OC(C)C)cc1]

The procedure is the similar as described in 1.2 of Protocol I. $^1$H NMR (400 MHz, chloroform-d) δ 11.70 (s, 1H), 7.90-7.84 (m, 1H), 7.81-7.76 (m, 2H), 7.58-7.52 (m, 2H), 7.29-7.20 (m, 2H), 5.90 (s, 1H), 4.67 (pd, J=6.1, 0.7 Hz, 1H), 2.37 (s, 3H), 1.44 (d, J=6.1 Hz, 6H). $^{13}$C NMR (101 MHz, CDCl$_3$) δ 181.7772, 178.1510, 166.0865, 144.5499, 143.1954, 136.6537, 136.2059, 133.5053, 129.9101, 127.3028, 120.8462, 120.0144, 114.9951, 103.5304, 73.2671, 21.5717, 21.4662.

Compound 18. N-(7-isopropoxy-5,8-dioxo-5,8-dihydronaphthalen-1-yl)-4-methylbenzenesulfonamide

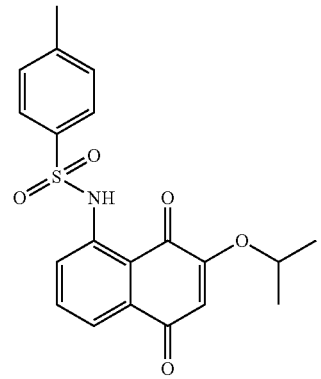 [SMILES: Cc1ccc(S(=O)(=O)Nc2cccc3c2C(=O)C(OC(C)C)=CC3=O)cc1]

The procedure is the similar as described in 1.2 of Protocol I. $^1$H NMR (400 MHz, chloroform-d) δ 11.58 (s, 1H), 7.96 (dd, J=8.5, 1.2 Hz, 1H), 7.83-7.78 (m, 2H), 7.74 (dd, J=7.6, 1.2 Hz, 1H), 7.60 (dd, J=8.5, 7.6 Hz, 1H), 7.31-7.18 (m, 4H), 6.08 (s, 1H), 4.54 (p, J=6.1 Hz, 1H), 2.37 (s, 4H), 1.44 (d, J=6.1 Hz, 6H). $^{13}$C NMR (101 MHz, CDCl$_3$) δ 183.8863, 183.6724, 158.3478, 144.4550, 140.7951, 136.2472, 135.8801, 132.7770, 129.8731, 127.3590, 122.2825, 121.2252, 115.4772, 109.9510, 72.8706, 21.5721, 21.1200.

Compound 19. 2,2,2-trifluoro-N-(5-isopropoxy-7,8-dioxo-7,8-dihydronaphthalen-1-yl)acetamide 19.1. Synthesis of 2,2,2-trifluoro-N-(8-oxo-5,6,7,8-tetrahydronaphthalen-1-yl)acetamide

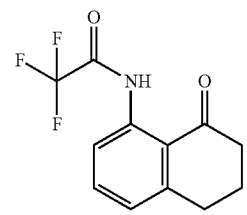

To the solution of 8-amino-3,4-dihydronaphthalen-1(2H)-one (1 equivalent) and Et$_3$N (3 equivalents) in THF, (CF$_3$CO)$_2$O was added in drop-wisely. The mixture was stirred at room temperature for 2 hours. After concentration, the residue is dissolved in DCM and washed with sat. NaHCO$_3$ and brine in sequence. The organic layer was collected and dried. After concentration, the residue afforded was purified with silica gel column chromatography to give a pure product. $^1$H NMR (400 MHz, chloroform-d) δ 13.37 (s, 1H), 8.65-8.33 (m, 1H), 7.53 (t, J=8.0 Hz, 1H), 7.10 (dq, J=7.7, 1.0 Hz, 1H), 3.02 (dd, J=6.7, 5.6 Hz, 2H), 2.83-2.62 (m, 2H), 2.13 (p, J=6.5 Hz, 2H).

19.2. Synthesis of 2,2,2-trifluoro-N-(7-hydroxy-5,8-dioxo-5,8-dihydronaphthalen-1-yl)acetamide

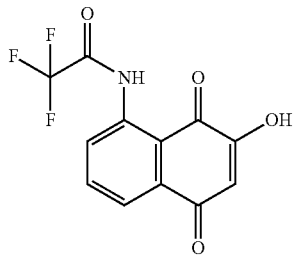 [SMILES: O=C1C=C(O)C(=O)c2c(NC(=O)C(F)(F)F)cccc21]

The procedure is the similar as described in I.1 of Protocol I. ¹H NMR (400 MHz, acetone-$d_6$) δ 9.38 (s, 1H), 7.49 (dd, J=8.5, 7.2 Hz, 1H), 7.29 (dd, J=7.2, 1.1 Hz, 1H), 7.15 (dd, J=8.5, 1.1 Hz, 1H), 6.09 (d, J=0.8 Hz, 1H).

19.3. Synthesis of 2,2,2-trifluoro-N-(5-isopropoxy-7,8-dioxo-7,8-dihydro-naphthalen-1-yl)acetamide

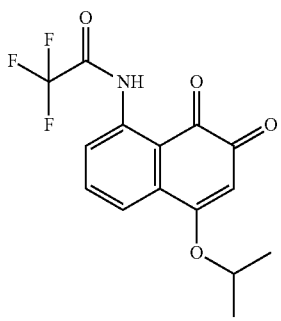 [SMILES: CC(C)OC1=CC(=O)C(=O)c2c(NC(=O)C(F)(F)F)cccc21]

The procedure is the similar as described in 1.2 of Protocol I. ¹H NMR (400 MHz, chloroform-d) δ 7.34 (dd, J=8.5, 7.4 Hz, 1H), 7.21 (dd, J=7.4, 1.1 Hz, 1H), 6.81 (dd, J=8.5, 1.1 Hz, 1H), 5.90 (d, J=0.7 Hz, 1H), 4.66 (pd, J=6.1, 0.7 Hz, 1H), 1.44 (d, J=6.1 Hz, 6H). ¹³C NMR (101 MHz, CDCl₃) δ 182.5, 177.5, 166.1, 156.2 (q, J=38.4 Hz), 141.1, 137.3, 133.6, 116.3, 115.4 (q, J=289.8 Hz), 103.6, 73.6, 21.5.

Compound 20. 2,2,2-trifluoro-N-(7-isopropoxy-5,8-dioxo-5,8-dihydronaphthalen-1-yl)acetamide

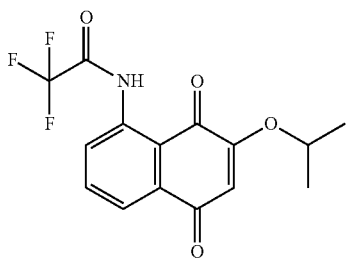 [SMILES: CC(C)OC1=CC(=O)c2cccc(NC(=O)C(F)(F)F)c2C1=O]

The procedure is the similar as described in 1.2 of Protocol I. ¹H NMR (400 MHz, chloroform-d) δ 7.47-7.35 (m, 2H), 6.89 (dd, J=7.1, 2.5 Hz, 1H), 6.05 (d, J=0.7 Hz, 1H), 4.54 (pd, J=6.1, 0.7 Hz, 1H), 1.45 (d, J=6.1 Hz, 6H). ¹³C NMR (101 MHz, CDCl₃) δ 184.4, 183.6, 158.2, 156.1 (q, J=38.4 Hz), 138.6, 136.4, 132.5, 125.3, 123.4, 116.8, 115.4 (q, J=289.9 Hz), 110.2, 73.1, 21.1.

Compound 21. N-(5-isopropoxy-7,8-dioxo-7,8-dihydronaphthalen-1-yl)methanesulfonamide

21.1. Synthesis of N-(8-oxo-5,6,7,8-tetrahydronaphthalen-1-yl)methanesulfonamide

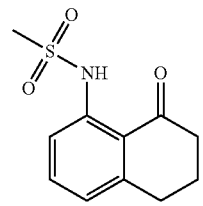 [SMILES: CS(=O)(=O)Nc1cccc2c1C(=O)CCC2]

To the solution of 8-amino-3,4-dihydronaphthalen-1(2H)-one (1 equivalent) in pyridine, MsCl (1.5 equivalents) was dropped in, and the mixture was stirred at room temperature for overnight. After concentration, the residue was dissolved in DCM and washed with 1M HCl and brine in sequence. After drying and concentration, the residue was purified through silica gel column chromatography to give a yellow solid. ¹H NMR (400 MHz, chloroform-d) δ 11.82 (s, 1H), 7.61-7.53 (m, 1H), 7.44 (dd, J=8.4, 7.5 Hz, 1H), 6.95 (dq, J=7.6, 1.0 Hz, 1H), 3.07 (s, 3H), 2.98 (ddd, J=7.1, 5.4, 1.0 Hz, 2H), 2.71 (ddd, J=7.2, 5.7, 0.6 Hz, 2H), 2.17-2.04 (m, 2H).

21.2. Synthesis of N-(7-hydroxy-5,8-dioxo-5,8-dihydronaphthalen-1-yl)methanesulfonamide

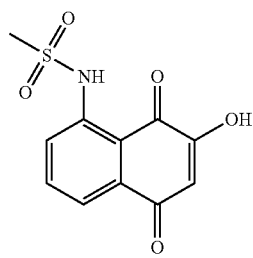 [SMILES: CS(=O)(=O)Nc1cccc2c1C(=O)C(O)=CC2=O]

The procedure is the similar as described in I.1 of Protocol I. ¹H NMR (400 MHz, acetone-$d_6$) δ 11.07 (s, 1H), 8.05-7.99 (m, 1H), 7.89 (dd, J=8.4, 7.6 Hz, 1H), 7.79 (dd, J=7.5, 1.2 Hz, 1H), 6.25 (s, 1H), 3.31 (s, 3H).

21.3. Synthesis of N-(5-isopropoxy-7,8-dioxo-7,8-dihydronaphthalen-1-yl)methanesulfonamide

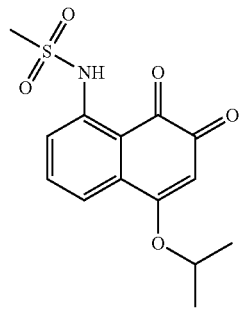 [SMILES: CC(C)OC1=CC(=O)C(=O)c2c(NS(C)(=O)=O)cccc21]

The procedure is the similar as described in 1.2 of Protocol I. $^1$H NMR (400 MHz, chloroform-d) δ 11.49 (s, 1H), 7.92 (dd, J=7.4, 2.3 Hz, 1H), 7.77-7.59 (m, 2H), 6.02-5.91 (m, 1H), 4.73 (pd, J=6.1, 0.7 Hz, 1H), 3.14 (s, 3H), 1.48 (d, J=6.1 Hz, 6H). $^{13}$C NMR (101 MHz, CDCl3) δ 181.8729, 178.0781, 166.0218, 143.3545, 137.0371, 133.8688, 120.2832, 120.0807, 114.9354, 103.7022, 73.3731, 41.0293, 21.4969.

Compound 22. N-(7-isopropoxy-5,8-dioxo-5,8-dihydronaphthalen-1-yl)methanesulfonamide

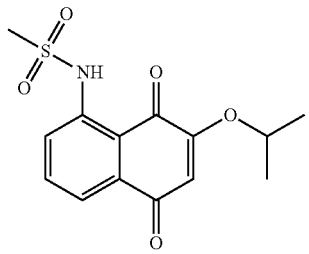 [SMILES: CC(C)OC1=CC(=O)c2cccc(NS(C)(=O)=O)c2C1=O]

The procedure is the similar as described in 1.2 of Protocol I. $^1$H NMR (400 MHz, chloroform-d) δ 11.35 (s, 1H), 8.02 (dd, J=8.5, 1.2 Hz, 1H), 7.86 (dd, J=7.6, 1.2 Hz, 1H), 7.74 (dd, J=8.5, 7.6 Hz, 1H), 6.14 (d, J=0.7 Hz, 1H), 4.65-4.49 (m, 1H), 3.13 (s, 3H), 1.46 (d, J=6.1 Hz, 6H). $^{13}$C NMR (101 MHz, CDCl$_3$) δ 183.8230, 174.5278, 158.4072, 140.9151, 136.2744, 133.0524, 126.5187, 122.0135, 121.4703, 110.0207, 72.9290, 40.8207, 21.1270.

Compound 23. 1,1,1-trifluoro-N-(5-isopropoxy-7,8-dioxo-7,8-dihydronaphthalen-1-yl)methanesulfonamide

23.1. Synthesis of 1,1,1-trifluoro-N-(7-hydroxy-5,8-dioxo-5,8-dihydronaphthalen-1-yl)methanesulfonamide

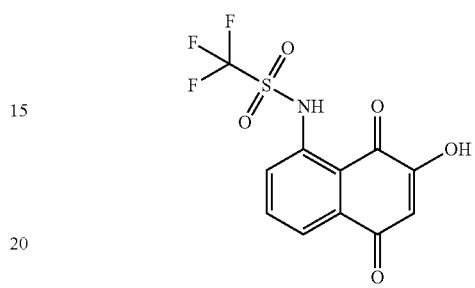

To the solution of 8-amino-3,4-dihydronaphthalen-1(2H)-one (1 equivalent) in DCM, Tf$_2$O (1.05 equivalents) is dropped in, and the mixture was stirred at room temperature for overnight. After concentration, the residue was dissolved in DCM and washed with brine. The organic layer was collected and dried over MgSO$_4$. After concentration, dark yellow oil was afforded. Then the oil was directly used as described in 1.1 of Protocol I. $^1$H NMR (400 MHz, DMSO-d$_6$) δ 11.74 (s, 1H), 7.92-7.77 (m, 2H), 7.73-7.64 (m, 1H), 6.34-5.91 (m, 1H).

23.2. Synthesis of 1,1,1-trifluoro-N-(5-isopropoxy-7,8-dioxo-7,8-dihydronaphthalen-1-yl)methanesulfonamide

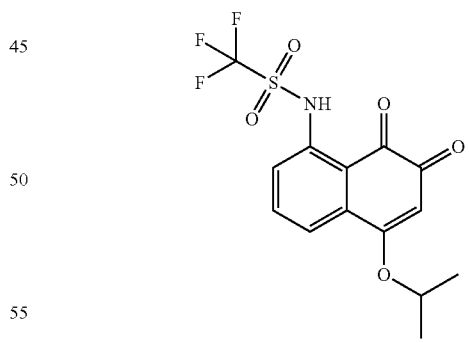

The procedure is the similar as described in 1.2 of Protocol I. $^1$H NMR (400 MHz, chloroform-d) δ 12.09 (s, 1H), 7.99-7.90 (m, 1H), 7.82-7.65 (m, 2H), 5.99 (s, 1H), 4.74 (hept, J=6.2 Hz, 1H), 1.49 (d, J=6.1 Hz, 6H). $^{13}$C NMR (101 MHz, CDCl$_3$) δ 185.0, 164.9, 151.6, 147.8, 134.1, 133.4, 129.5, 126.6, 125.8, 122.4, 120.0, 104.3, 73.7, 21.5.

Compound 24. N-(5-isopropoxy-7,8-dioxo-7,8-dihydronaphthalen-1-yl)acetamide

24.1. Synthesis of N-(7-hydroxy-5,8-dioxo-5,8-dihydronaphthalen-1-yl)acetamide

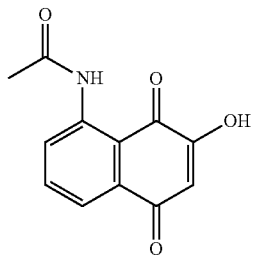 [SMILES: CC(=O)Nc1cccc2c1C(=O)C(O)=CC2=O]

The procedure is the similar as described in I.1 of Protocol I. $^1$H NMR (400 MHz, DMSO-d$_6$) δ 11.73 (s, 1H), 11.46 (s, 1H), 8.76 (dd, J=8.5, 1.2 Hz, 1H), 7.79 (dd, J=8.5, 7.5 Hz, 1H), 7.67 (dd, J=7.6, 1.2 Hz, 1H), 6.13 (s, 1H), 2.21 (s, 3H).

24.2. Synthesis of N-(5-isopropoxy-7,8-dioxo-7,8-dihydronaphthalen-1-yl)acetamide

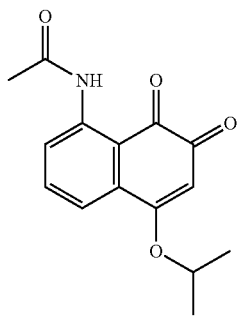 [SMILES: CC(=O)Nc1cccc2c1C(=O)C(=O)C=C2OC(C)C]

The procedure is the similar as described in 1.2 of Protocol I. $^1$H NMR (400 MHz, chloroform-d) δ 11.95 (s, 1H), 8.92 (dd, J=7.7, 2.2 Hz, 1H), 7.75-7.57 (m, 2H), 5.94 (d, J=0.7 Hz, 1H), 4.84-4.55 (m, 1H), 2.29 (s, 3H), 1.48 (d, J=6.1 Hz, 6H). $^{13}$C NMR (101 MHz, CDCl$_3$) δ 182.3137, 178.3425, 170.0191, 166.5929, 144.0849, 136.9272, 132.9653, 123.5257, 120.1079, 114.8268, 103.2219, 73.1866, 25.6598, 21.5036.

Compound 25. N-(5-(cyclohexyloxy)-7,8-dioxo-7,8-dihydronaphthalen-1-yl)acetamide The procedure is the similar as described in 1.2 of Protocol I. $^1$H NMR (400 MHz, chloroform-d) δ 11.95 (s, 1H), 8.91 (dd, J=6.5, 3.3 Hz, 1H), 7.81-7.53 (m, 2H), 5.95 (d, J=0.7 Hz, 1H), 4.48 (tt, J=8.0, 3.6 Hz, 1H), 2.29 (s, 3H), 2.10-1.97 (m, 2H), 1.83 (ddq, J=13.0, 6.8, 3.6 Hz, 2H), 1.72 (dtd, J=12.8, 8.8, 3.7 Hz, 2H), 1.66-1.55 (m, 1H), 1.54-1.37 (m, 3H). $^{13}$C NMR (101 MHz, CDCl$_3$) δ 182.4059, 178.3763, 170.0678, 166.5722, 144.0836, 136.9674, 133.0857, 123.5459, 120.0745, 114.8785, 103.2807, 77.9785, 30.9482, 25.6908, 25.2076, 23.2983.

Compound 26. N-(5-(cyclohexyloxy)-7,8-dioxo-7,8-dihydronaphthalen-1-yl)methanesulfonamide

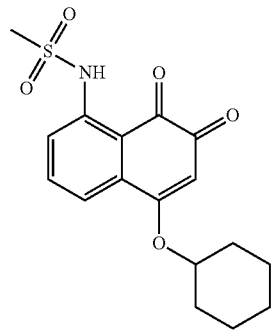 [SMILES: CS(=O)(=O)Nc1cccc2c1C(=O)C(=O)C=C2OC1CCCCC1]

The procedure is the similar as described in 1.2 of Protocol I. $^1$H NMR (400 MHz, chloroform-d) δ 11.49 (s, 1H), 8.01-7.81 (m, 1H), 7.79-7.60 (m, 2H), 5.98 (d, J=0.7 Hz, 1H), 4.49 (tt, J=8.1, 3.6 Hz, 1H), 3.14 (s, 3H), 2.02 (d, J=12.1 Hz, 2H), 1.93-1.79 (m, 2H), 1.77-1.66 (m, 2H), 1.66-1.58 (m, 1H), 1.47 (m, 3H).

Compound 27. N-(5-(3-hydroxypropoxy)-7,8-dioxo-7,8-dihydronaphthalen-1-yl)acetamide

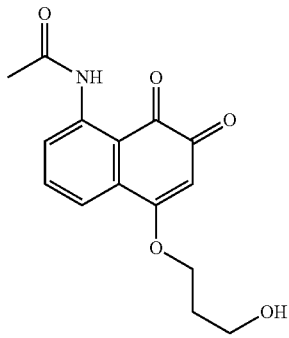 [SMILES: CC(=O)Nc1cccc2c1C(=O)C(=O)C=C2OCCCO]

The procedure is the similar as described in 1.2 of Protocol I. $^1$H NMR (400 MHz, chloroform-d) δ 11.90 (s, 1H), 8.90 (dd, J=8.5, 1.3 Hz, 1H), 7.81-7.50 (m, 2H), 5.97 (s, 1H), 4.28 (t, J=6.1 Hz, 2H), 3.92 (t, J=6.0 Hz, 2H), 2.29 (s, 3H), 2.17 (p, J=6.0 Hz, 2H). $^{13}$C NMR (101 MHz, CDCl$_3$) δ 182.0443, 178.3040, 170.0665, 167.6724, 144.2454, 137.0371, 132.4691, 123.6320, 119.8501, 114.5499, 103.0378, 66.8157, 58.8642, 31.2597, 25.6845.

Compound 28. N-(5-(hexyloxy)-7,8-dioxo-7,8-dihydronaphthalen-1-yl)acetamide

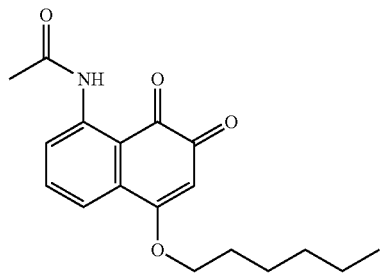 [SMILES: CCCCCCOC1=CC(=O)C(=O)c2c(NC(C)=O)cccc21]

The procedure is the similar as described in 1.2 of Protocol I. $^1$H NMR (400 MHz, chloroform-d) δ 11.92 (s, 1H), 8.90 (dt, J=8.5, 1.5 Hz, 1H), 7.75-7.49 (m, 2H), 5.93 (d, J=1.1 Hz, 1H), 4.12 (t, J=6.4 Hz, 2H), 2.28 (d, J=1.1 Hz, 3H), 2.00-1.83 (m, 2H), 1.50 (td, J=10.8, 9.0, 4.5 Hz, 2H), 1.36 (dq, J=6.5, 3.3 Hz, 4H), 0.98-0.85 (m, 3H). $^{13}$C NMR (101 MHz, CDCl$_3$) δ 182.2190, 178.3155, 170.0402, 167.8026, 144.1792, 137.0252, 132.6424, 123.5392, 119.9033, 114.6374, 102.8482, 70.1471, 31.3632, 28.3866, 25.6722, 22.5044, 13.9790.

Compound 29. 8-amino-4-isopropoxynaphthalene-1,2-dione

29.1. Synthesis of 8-amino-2-hydroxynaphthalene-1,4-dione

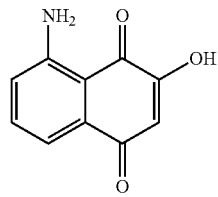 [SMILES: Nc1cccc2c1C(=O)C(O)=CC2=O]

The procedure is the similar as described in I.1 of Protocol I. $^1$H NMR (400 MHz, DMSO-d$_6$) δ 11.18 (s, 1H), 7.85 (s, 2H), 7.42 (dd, J=8.5, 7.2 Hz, 1H), 7.18-7.04 (m, 2H), 6.00 (s, 1H).

29.2 Synthesis of 8-amino-4-isopropoxynaphthalene-1,2-dione

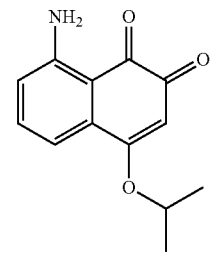 [SMILES: CC(C)OC1=CC(=O)C(=O)c2c(N)cccc21]

The procedure is the similar as described in 1.2 of Protocol I. $^1$H NMR (400 MHz, chloroform-d) δ 7.31 (ddt, J=8.6, 7.5, 1.0 Hz, 1H), 7.18 (dq, J=7.4, 1.1 Hz, 1H), 6.83 (dt, J=8.5, 1.2 Hz, 1H), 5.88 (s, 1H), 4.74-4.54 (m, 1H), 1.45-1.38 (m, 6H).

Compound 30. 8-amino-2-isopropoxynaphthalene-1,4-dione

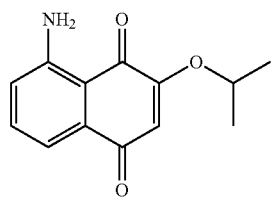 [SMILES: CC(C)OC1=CC(=O)c2cccc(N)c2C1=O]

The procedure is the similar as described in 1.2 of Protocol I. $^1$H NMR (400 MHz, chloroform-d) δ 7.47-7.37 (m, 2H), 6.89 (dd, J=7.0, 2.5 Hz, 1H), 6.83-6.58 (m, OH), 6.14-5.95 (m, 1H), 4.54 (hept, J=6.1 Hz, 1H), 1.44 (dd, J=6.1, 0.6 Hz, 6H). $^{13}$C NMR (101 MHz, CDCl$_3$) δ 185.3346, 181.8586, 159.3019, 150.5733, 134.9791, 132.9417, 122.5211, 122.4967, 116.4649, 111.6104, 109.4049, 72.1941, 21.1909.

Compound 31. 2-isopropoxy-8-(isopropylamino)naphthalene-1,4-dione

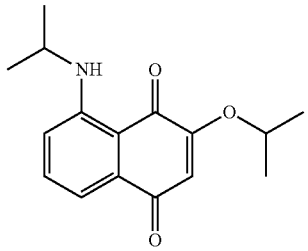 [SMILES: CC(C)Nc1cccc2c1C(=O)C(OC(C)C)=CC2=O]

The procedure is the similar as described in 1.2 of Protocol I. $^1$H NMR (400 MHz, chloroform-d) δ 9.96 (d, J=7.5 Hz, 1H), 7.39 (ddd, J=8.9, 7.4, 0.7 Hz, 1H), 7.16 (dd, J=7.3, 0.9 Hz, 1H), 6.94 (dd, J=8.9, 1.0 Hz, 1H), 5.87 (d, J=0.7 Hz, 1H), 4.64 (pd, J=6.1, 0.7 Hz, 1H), 3.96-3.75 (m, 1H), 1.43 (d, J=6.1 Hz, 6H), 1.33 (d, J=6.4 Hz, 6H). $^{13}$C NMR (101 MHz, CDCl$_3$) δ 180.8506, 179.4074, 166.0351, 152.5178, 135.9001, 133.2041, 116.8025, 113.7167, 110.1272, 103.4060, 72.1372, 43.8944, 22.8264, 21.5136.

Compound 32. 5-bromo-4-isopropoxynaphthalene-1,2-dione 32.1. Synthesis of 5-bromo-2-hydroxynaphthalene-1,4-dione

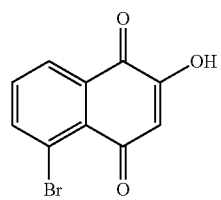 [SMILES: O=C1C(O)=CC(=O)c2c(Br)cccc21]

The procedure is the similar as described in I.1 of Protocol I. $^1$H NMR (400 MHz, DMSO-d$_6$) δ 8.07-7.99 (m, 2H), 7.61 (t, J=7.8 Hz, 1H), 6.14 (s, 1H).

32.2. Synthesis of 5-bromo-4-isopropoxynaphthalene-1,2-dione

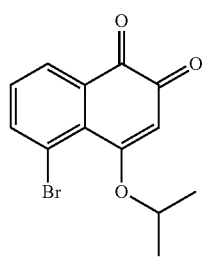 [SMILES: CC(C)OC1=CC(=O)C(=O)c2cccc(Br)c21]

The procedure is the similar as described in 1.2 of Protocol I. $^1$H NMR (400 MHz, chloroform-d) δ 8.14 (dd, J=7.6, 1.4 Hz, 1H), 7.95 (dd, J=8.1, 1.4 Hz, 1H), 7.36 (dd, J=8.1, 7.5 Hz, 1H), 6.03 (d, J=0.7 Hz, 1H), 4.79 (pd, J=6.1, 0.8 Hz, 1H), 1.54 (d, J=6.1 Hz, 6H). $^{13}$C NMR (101 MHz, CDCl$_3$) δ 179.2294, 178.5815, 167.1493, 142.9512, 133.6056, 131.4794, 130.1403, 129.1675, 120.3242, 104.6647, 74.3598, 21.6037.

Compound 33. tert-butyl (8-isopropoxy-5,6-dioxo-5,6-dihydronaphthalen-2-yl)carbamate 33.1. Synthesis of tert-butyl (6-hydroxy-5,8-dioxo-5,8-dihydronaphthalen-2-yl)carbamate

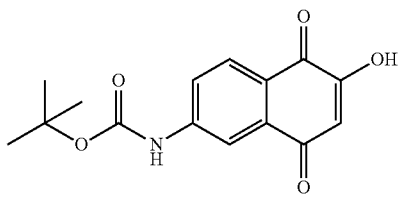 [SMILES: CC(C)(C)OC(=O)Nc1ccc2c(c1)C(=O)C=C(O)C2=O]

The procedure is the similar as described in 1.1 of Protocol I. $^1$H NMR (400 MHz, DMSO-d$_6$) δ 11.57 (s, 1H), 10.09 (s, 1H), 8.09 (d, J=2.2 Hz, 1H), 7.90 (d, J=8.5 Hz, 1H), 7.75 (dd, J=8.6, 2.3 Hz, 1H), 6.09 (s, 1H), 1.48 (s, 9H).

33.2. Synthesis of tert-butyl (8-isopropoxy-5,6-dioxo-5,6-dihydronaphthalen-2-yl)carbamate

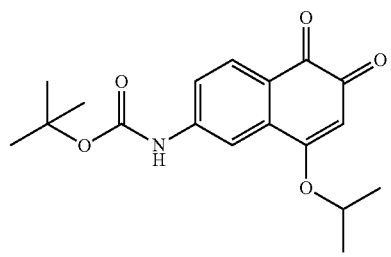 [SMILES: CC(C)OC1=CC(=O)C(=O)c2ccc(NC(=O)OC(C)(C)C)cc21]

The procedure is the similar as described in 1.2 of Protocol I. $^1$H NMR (400 MHz, chloroform-d) δ 8.07 (d, J=8.4 Hz, 1H), 7.72 (d, J=2.2 Hz, 1H), 7.69 (dd, J=8.4, 2.3 Hz, 1H), 6.86 (s, 1H), 5.92 (d, J=0.7 Hz, 1H), 4.71 (pd, J=6.1, 0.8 Hz, 1H), 1.54 (s, 9H), 1.48 (d, J=6.1 Hz, 6H). $^{13}$C NMR (101 MHz, CDCl$_3$) δ 180.0861, 178.2095, 166.1075, 151.8005, 144.8823, 144.8722, 133.9999, 130.9850, 125.1944, 119.4133, 113.7669, 104.1746, 81.9123, 72.9894, 28.2085, 21.5147.

Compound 34. 6-chloro-4-isopropoxynaphthalene-1,2-dione 34.1. Synthesis of 6-chloro-3,4-dihydronaphthalen-1(2H)-one

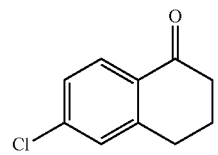 [SMILES: O=C1CCCc2cc(Cl)ccc21]

The procedure is the similar as described in 6.3 of Example 6. $^1$H NMR (400 MHz, chloroform-d) δ 7.97 (d, J=8.2 Hz, 1H), 7.30-7.26 (m, 2H), 2.94 (t, J=6.1 Hz, 2H), 2.65 (t, J=6.1 Hz, 2H), 2.23-2.06 (m, 2H).

34.2. Synthesis of 6-chloro-2-hydroxynaphthalene-1,4-dione

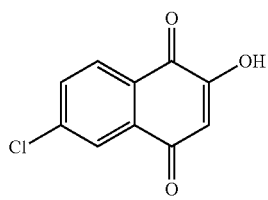 [SMILES: O=C1C=C(O)C(=O)c2ccc(Cl)cc21]

The procedure is the similar as described in I.1 of Protocol I. $^1$H NMR (400 MHz, acetone-d$_6$) δ 9.98 (s, 1H), 8.09 (d, J=8.3 Hz, 1H), 7.96 (d, J=2.1 Hz, 1H), 7.85 (dd, J=8.3, 2.2 Hz, 1H), 6.28 (s, 1H).

34.3. Synthesis of 6-chloro-4-isopropoxynaphthalene-1,2-dione

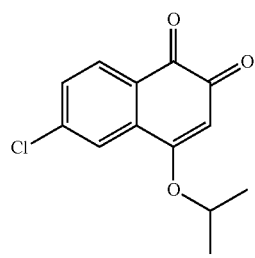

The procedure is the similar as described in 1.2 of Protocol I. $^1$H NMR (400 MHz, chloroform-d) δ 8.04 (d, J=8.2 Hz, 1H), 7.82 (d, J=2.0 Hz, 1H), 7.53 (dd, J=8.3, 2.1 Hz, 1H), 5.97 (d, J=0.7 Hz, 1H), 4.73 (pd, J=6.1, 0.8 Hz, 1H), 1.49 (d, J=6.1 Hz, 6H). $^{13}$C NMR (101 MHz, CDCl$_3$) δ 179.0240, 178.5214, 165.3172, 141.8832, 134.0392, 131.3662, 130.3088, 128.8000, 125.1479, 104.6326, 73.4627, 21.5058.

Compound 35. 6-chloro-4-(cyclohexyloxy)naphthalene-1,2-dione

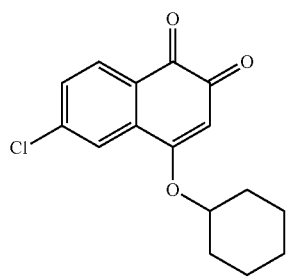

The procedure is the similar as described in 1.2 of Protocol I. $^1$H NMR (400 MHz, chloroform-d) δ 8.06 (dd, J=8.2, 0.4 Hz, 1H), 7.84 (d, J=2.1 Hz, 1H), 7.55 (dd, J=8.2, 2.1 Hz, 1H), 6.00 (d, J=0.7 Hz, 1H), 4.55-4.40 (m, 1H), 2.12-1.99 (m, 2H), 1.85 (td, J=8.5, 7.1, 4.1 Hz, 2H), 1.80-1.67 (m, 2H), 1.63 (ddd, J=11.9, 6.1, 3.0 Hz, 1H), 1.55-1.36 (m, 3H). $^{13}$C NMR (101 MHz, CDCl$_3$) δ 179.0630, 178.5982, 165.2949, 141.8788, 134.1441, 131.3767, 130.3289, 128.8452, 125.1026, 104.6834, 78.3785, 31.0132, 25.1714, 23.4339.

Compound 36. 6-bromo-4-isopropoxynaphthalene-1,2-dione

36.1. Synthesis of 6-bromo-2-hydroxynaphthalene-1,4-dione

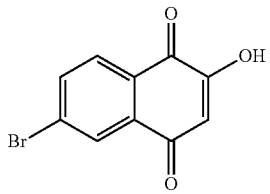

The procedure is the similar as described in I.1 of Protocol I. $^1$H NMR (400 MHz, chloroform-d) δ 8.25 (dd, J=2.0, 0.4 Hz, 1H), 7.97 (dd, J=8.2, 0.5 Hz, 1H), 7.86 (dd, J=8.2, 2.0 Hz, 1H), 6.37 (s, 1H).

36.2. Synthesis of 6-bromo-4-isopropoxynaphthalene-1,2-dione

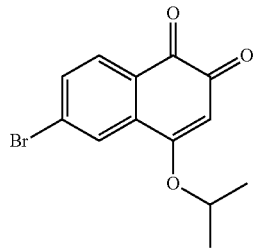 [SMILES: CC(C)OC1=CC(=O)C(=O)c2ccc(Cl)cc21]

The procedure is the similar as described in 1.2 of Protocol I. $^1$H NMR (400 MHz, chloroform-d) δ 8.05-7.91 (m, 2H), 7.72 (dd, J=8.2, 1.9 Hz, 1H), 5.97 (d, J=0.7 Hz, 1H), 4.73 (dtd, J=12.3, 6.2, 0.7 Hz, 1H), 1.50 (d, J=6.1 Hz, 6H). $^{13}$C NMR (101 MHz, CDCl$_3$) δ 178.9866, 178.7845, 165.3252, 134.4367, 133.8986, 130.6450, 130.2791, 129.1725, 128.0486, 104.6405, 73.4852, 21.5092.

Compound 37.
6,7-dichloro-4-isopropoxynaphthalene-1,2-dione

37.1. Synthesis of 4-(3,4-dichlorophenyl)-4-oxobutanoic acid

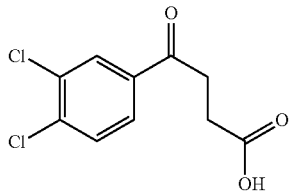 [SMILES: O=C(O)CCC(=O)c1ccc(Cl)c(Cl)c1]

The mixture of 1,2-dichlorobenzene (6 equivalents), dihydrofuran-2,5-dione (1 equivalent), and $AlCl_3$ (3 equivalents) was heated for 3 hours at 60° C., and then it was cooled down to room temperature. After quenched with ice water, the mixture was stirred for 30 minutes. Subsequently, hexane was added and the mixture was stirred for further 2 hours to afford a beige solid. After filtration and washed with minimum ether, crude product was afforded and used directly in next step. $^1$H NMR (400 MHz, chloroform-d) δ 8.05 (d, J=2.0 Hz, 1H), 7.80 (dd, J=8.4, 2.1 Hz, 1H), 7.56 (d, J=8.3 Hz, 1H), 3.26 (t, J=6.4 Hz, 2H), 2.82 (t, J=6.4 Hz, 2H).

37.2. Synthesis of 4-(3,4-dichlorophenyl)butanoic acid

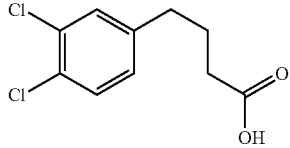 [SMILES: O=C(O)CCCc1ccc(Cl)c(Cl)c1]

To the mixture of 4-(3,4-dichlorophenyl)-4-oxobutanoic acid (0.5 g, 2.02 mmol) in diethylene glycol (10 mL), KOH (0.294 g, 5.25 mmol), hydrazine hydrate (64%, 0.196 mL, 4.04 mmol) and 2 drops of methanol were added in sequence. And then the mixture was refluxed at 120-130° C. for 90 minutes. After removal of the distilled funnel, the temperature was raised to 170° C. Once the reaction reached this temperature, the distilled funnel was added and the mixture was refluxed for 3 hours. After the mixture was cooled down to room temperature, water was added, and the mixture was treated with 2N HCl. After extraction with EtOAc, the organic layer was collected, dried over $MgSO_4$, and concentrated in vacuo. The residue was directly used in next step. $^1$H NMR (400 MHz, chloroform-d) δ 7.35 (d, J=8.2 Hz, 1H), 7.28 (d, J=2.1 Hz, 1H), 7.02 (dd, J=8.2, 2.1 Hz, 1H), 2.67-2.61 (m, 2H), 2.40-2.35 (m, 2H), 1.99-1.90 (m, 2H).

37.3. Synthesis of 6,7-dichloro-3,4-dihydronaphthalen-1(2H)-one

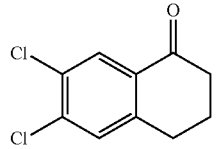 [SMILES: O=C1CCCc2cc(Cl)c(Cl)cc21]

The crude product from 37.2 was mixed with PPA, and heated at 80° C. for 1 hour. After then the temperature was raised to 120° C. and the mixture was stirred for overnight. After cooled down to room temperature, ice water was added carefully. An off-white precipitate appeared. After filtration, the precipitate was dissolved in EtOAc, and the organic phase was washed with 2N NaOH for triple times followed with brine one time. The organic phase was collected, dried over $MgSO_4$, and concentrated in vacuum. After silica gel column flash chromatography, beige solid was afforded. $^1$H NMR (400 MHz, chloroform-d) δ 8.09 (d, J=0.5 Hz, 1H), 7.38 (q, J=0.8 Hz, 1H), 2.96-2.88 (m, 2H), 2.69-2.61 (m, 2H), 2.21-2.07 (m, 2H).

37.4. Synthesis of 6,7-dichloro-2-hydroxynaphthalene-1,4-dione

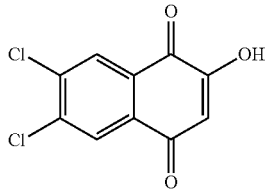 [SMILES: O=C1C=C(O)C(=O)c2cc(Cl)c(Cl)cc21]

The procedure is the similar as described in 1.1 of Protocol I. $^1$H NMR (400 MHz, DMSO-$d_6$) δ 12.03 (s, 1H), 8.10 (s, 1H), 8.02 (s, 1H), 6.18 (s, 1H).

37.5 Synthesis of 6,7-dichloro-4-isopropoxynaphthalene-1,2-dione

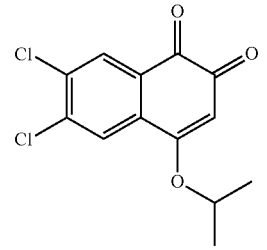 [SMILES: CC(C)OC1=CC(=O)C(=O)c2cc(Cl)c(Cl)cc21]

The procedure is the similar as described in Protocol III. $^1$H NMR (400 MHz, chloroform-d) δ 8.15 (d, J=2.9 Hz, 1H), 7.92 (d, J=1.6 Hz, 1H), 5.97 (dd, J=1.4, 0.7 Hz, 1H), 4.74 (dtd, J=6.8, 6.1, 5.3 Hz, 1H), 1.49 (dd, J=6.1, 0.8 Hz, 6H).

Compound 38.
8-hydroxy-4-isopropoxynaphthalene-1,2-dione

38.1. Synthesis of 2-(dimethylamino)-8-hydroxynaphthalene-1,4-dione

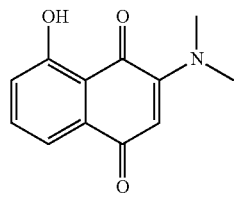 [SMILES: CN(C)C1=CC(=O)c2cccc(O)c2C1=O]

The procedure is the similar as described in III.1 of Protocol III. $^1$H NMR (400 MHz, DMSO-d$_6$) δ 11.44 (s, 1H), 7.65 (dd, J=8.4, 7.4 Hz, 1H), 7.40 (dd, J=7.4, 1.1 Hz, 1H), 7.17 (dd, J=8.4, 1.1 Hz, 1H), 5.72 (s, 1H), 3.15 (s, 6H).

38.2. Synthesis of 2,8-dihydroxynaphthalene-1,4-dione

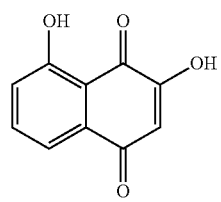

The procedure is the similar as described in 111.2 of Protocol III. $^1$H NMR (400 MHz, DMSO-d$_6$) δ 11.97 (s, 1H), 8.18 (dd, J=8.4, 7.4 Hz, 1H), 7.92 (dd, J=7.5, 1.1 Hz, 1H), 7.74 (dd, J=8.5, 1.1 Hz, 1H), 6.59 (s, 1H).

38.3. 8-hydroxy-4-isopropoxynaphthalene-1,2-dione

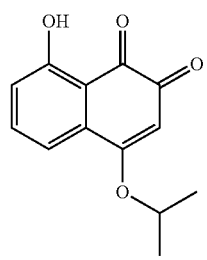 [SMILES: CC(C)OC1=CC(=O)C(=O)c2c(O)cccc21]

The procedure is the similar as described in 1.2 of Protocol I. $^1$H NMR (400 MHz, chloroform-d) δ 12.05 (s, 1H), 7.57 (dd, J=8.6, 7.6 Hz, 1H), 7.41 (dd, J=7.6, 1.0 Hz, 1H), 7.11 (dd, J=8.6, 1.0 Hz, 1H), 5.91 (d, J=0.7 Hz, 1H), 4.70 (pd, J=6.1, 0.7 Hz, 1H), 1.46 (d, J=6.1 Hz, 6H). $^{13}$C NMR (101 MHz, CDCl$_3$) δ 183.1246, 179.0784, 166.2935, 164.6731, 137.9894, 132.3614, 122.2688, 117.6077, 114.0522, 103.7876, 73.0444, 21.4965.

Compound 39.
4-(cyclohexyloxy)-8-hydroxynaphthalene-1,2-dione

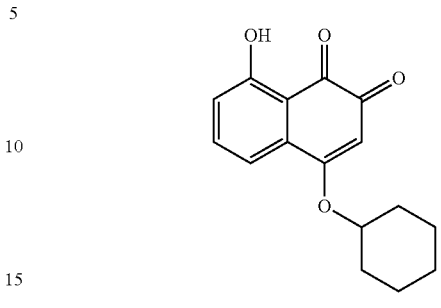

The procedure is the similar as described in 1.2 of Protocol I. $^1$H NMR (400 MHz, chloroform-d) δ 12.06 (s, 1H), 7.58 (dd, J=8.6, 7.5 Hz, 1H), 7.43 (dd, J=7.5, 1.0 Hz, 1H), 7.13 (dd, J=8.6, 1.0 Hz, 1H), 5.94 (d, J=0.7 Hz, 1H), 4.47 (tt, J=7.9, 3.5 Hz, 1H), 2.02 (ddt, J=12.1, 7.4, 3.8 Hz, 2H), 1.83 (ddt, J=13.2, 6.5, 3.3 Hz, 2H), 1.78-1.65 (m, 2H), 1.65-1.60 (m, 1H), 1.53-1.34 (m, 3H). $^{13}$C NMR (101 MHz, CDCl$_3$) δ 183.2138, 179.1012, 166.2450, 164.6696, 137.9829, 132.4856, 122.2709, 117.5353, 114.1101, 103.8613, 77.8314, 30.9477, 25.2153, 23.3017.

Compound 40.
5-hydroxy-4-isopropoxynaphthalene-1,2-dione

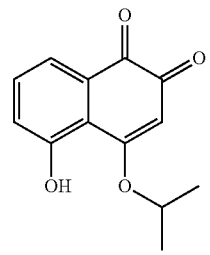 [SMILES: CC(C)OC1=CC(=O)C(=O)c2cccc(O)c21]

The procedure is the similar as described in 1.2 of Protocol I. $^1$H NMR (400 MHz, chloroform-d) δ 8.99 (s, 1H), 7.73 (dt, J=7.5, 1.2 Hz, 1H), 7.46-7.38 (m, 1H), 7.18 (dt, J=8.4, 1.0 Hz, 1H), 5.93 (d, J=0.7 Hz, 1H), 4.86 (heptd, J=6.2, 0.7 Hz, 1H), 1.56 (d, J=6.1 Hz, 6H). $^{13}$C NMR (101 MHz, CDCl3) δ 179.2154, 179.1590, 169.1390, 156.4681, 132.9201, 131.4566, 126.2739, 123.3429, 114.2511, 103.7173, 75.2516, 21.7160.

Compound 41.
5-hydroxy-2-isopropoxynaphthalene-1,4-dione

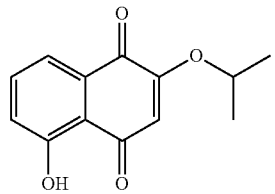 [SMILES: CC(C)OC1=CC(=O)c2c(O)cccc2C1=O]

The procedure is the similar as described in 1.2 of Protocol I. $^1$H NMR (400 MHz, chloroform-d) δ 12.27 (s, 1H), 7.68-7.63 (m, 1H), 7.59-7.51 (m, 1H), 7.27-7.23 (m, 1H), 6.06 (d, J=0.8 Hz, 1H), 4.58 (hept, J=6.1 Hz, 1H), 1.45 (d, J=6.1 Hz, 6H). $^{13}$C NMR (101 MHz, CDCl$_3$) δ 191.0817, 179.7657, 160.8936, 159.3698, 135.2874, 131.2021, 124.9593, 119.4690, 114.0613, 109.9407, 72.9169, 21.1406.

Compound 42. 4-isopropoxy-5-(2-morpholinoethoxy)naphthalene-1,2-dione 42.1. Synthesis of 2-(dimethylamino)-5-(2-morpholinoethoxy)naphthalene-1,4-dione

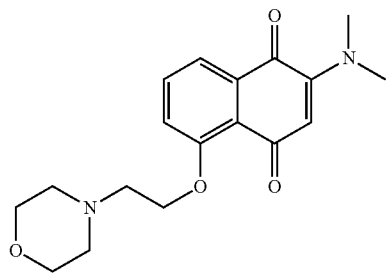 [SMILES: CN(C)C1=CC(=O)c2c(OCCN3CCOCC3)cccc2C1=O]

The mixture of 2-(dimethylamino)-8-hydroxynaphthalene-1,4-dione (1 equivalent), 4-(2-Chloroethyl)morpholine Hydrochloride (1.5 equivalents), KI (2 equivalents), and Cs$_2$CO$_3$ (4 equivalents) in DMF was stirred at room temperature for 24 hours. After dilution with water, the solution was extracted with EtOAc. The organic layer was combined, dried, and concentrated in vacuo. The red residue was directly used in the next step. $^1$H NMR (400 MHz, chloroform-d) δ 7.50 (ddt, J=7.6, 2.9, 1.6 Hz, 1H), 7.40 (tdd, J=7.6, 3.2, 1.7 Hz, 1H), 7.14 (dt, J=8.4, 1.5 Hz, 1H), 5.60-5.55 (m, 1H), 4.63 (s, 2H), 4.11 (ddq, J=5.6, 4.1, 1.9 Hz, 2H), 3.60 (dq, J=5.9, 2.9, 2.4 Hz, 4H), 3.01 (dd, J=3.3, 1.7 Hz, 6H), 2.72-2.61 (m, 4H).

42.2. Synthesis of 2-hydroxy-5-(2-morpholinoethoxy)naphthalene-1,4-dione

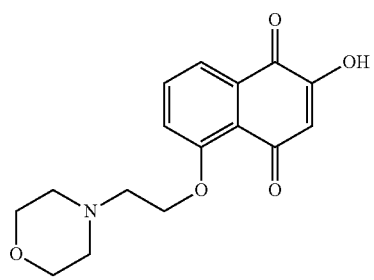 [SMILES: O=C1C(O)=CC(=O)c2c(OCCN3CCOCC3)cccc21]

The procedure is the similar as described in 111.2 of protocol III. $^1$H NMR (400 MHz, DMSO-d$_6$) δ 8.52 (s, 3H), 7.77 (dd, J=8.3, 7.6 Hz, 1H), 7.69 (dd, J=7.6, 1.1 Hz, 1H), 7.58 (dd, J=8.4, 1.2 Hz, 1H), 6.07 (s, 1H), 4.64-4.44 (m, 2H), 3.83 (s, 4H), 3.63-3.56 (m, 2H), 3.52-3.41 (m, 4H).

42.3. Synthesis of 4-isopropoxy-5-(2-morpholinoethoxy)naphthalene-1,2-dione

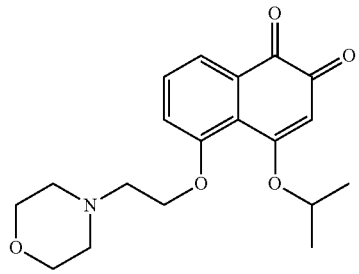 [SMILES: CC(C)OC1=CC(=O)C(=O)c2cccc(OCCN3CCOCC3)c21]

The procedure is the similar as described in 1.2 of Protocol I. $^1$H NMR (400 MHz, chloroform-d) δ 7.80 (dd, J=7.5, 1.2 Hz, 1H), 7.49 (dd, J=8.5, 7.5 Hz, 1H), 7.28 (d, J=1.2 Hz, 1H), 5.91 (d, J=0.8 Hz, 1H), 4.83-4.62 (m, 1H), 4.18 (t, J=6.1 Hz, 2H), 3.80-3.69 (m, 4H), 2.86 (t, J=6.1 Hz, 2H), 2.64-2.49 (m, 4H), 1.48 (d, J=6.0 Hz, 6H).

Compound 43. N-(5-(2-morpholinoethoxy)-7,8-dioxo-7,8-dihydronaphthalen-1-yl)acetamide

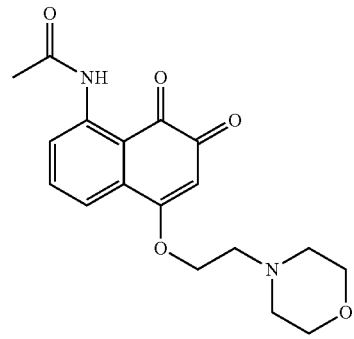 [SMILES: CC(=O)Nc1cccc2c1C(=O)C(=O)C=C2OCCN1CCOCC1]

The procedure is the similar as described in 1.2 of Protocol I. $^1$H NMR (400 MHz, acetone-d$_6$) δ 11.83 (s, 1H), 8.89 (dd, J=8.7, 1.2 Hz, 1H), 7.77 (dd, J=8.6, 7.7 Hz, 1H), 7.69 (dd, J=7.7, 1.2 Hz, 1H), 6.03 (s, 1H), 4.39 (t, J=5.4 Hz, 2H), 3.72-3.55 (m, 4H), 2.94 (t, J=5.5 Hz, 2H), 2.59 (m, 4H), 2.27 (s, 4H). $^{13}$C NMR (101 MHz, acetone) δ 182.0166, 177.6957, 169.3293, 166.7482, 143.9618, 136.6088, 132.9504, 122.6517, 122.5873, 119.4365, 103.1554, 67.9483, 66.5648, 56.5726, 53.8411, 24.6194.

Compound 44. N-(7-(2-morpholinoethoxy)-5,8-dioxo-5,8-dihydronaphthalen-1-yl)acetamide

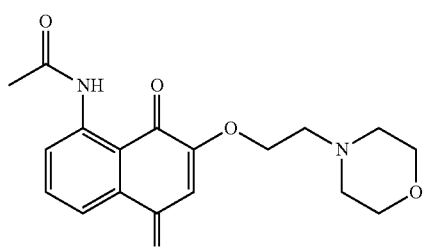

The procedure is the similar as described in 1.2 of Protocol I. ¹H NMR (400 MHz, chloroform-d) δ 11.75 (s, 1H), 9.00 (dd, J=8.6, 1.3 Hz, 1H), 7.80 (dd, J=7.6, 1.3 Hz, 1H), 7.69 (dd, J=8.6, 7.5 Hz, 1H), 6.12 (s, 1H), 4.12 (t, J=5.7 Hz, 2H), 3.75-3.68 (m, 4H), 2.89 (t, J=5.6 Hz, 2H), 2.65-2.53 (m, 4H), 2.27 (s, 3H).

Compound 45. N-(7-(2-(dimethylamino)ethoxy)-5,8-dioxo-5,8-dihydronaphthalen-1-yl)acetamide

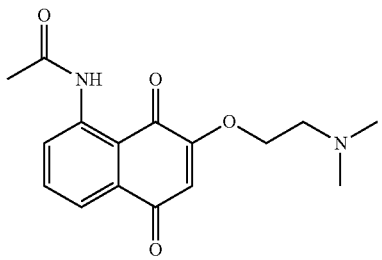 [SMILES: CC(=O)Nc1cccc2c1C(=O)C(OCCN(C)C)=CC2=O]

The procedure is the similar as described in 1.2 of Protocol I. ¹H NMR (400 MHz, acetone-d₆) δ 11.69 (s, 1H), 8.97 (dd, J=8.3, 1.5 Hz, 1H), 7.76 (dd, J=8.3, 7.6 Hz, 1H), 7.71 (dd, J=7.5, 1.5 Hz, 1H), 6.25 (s, 1H), 4.19 (t, J=5.6 Hz, 2H), 2.79 (t, J=5.6 Hz, 2H), 2.31 (s, 6H), 2.27 (s, 3H). ¹³C NMR (101 MHz, acetone) δ 183.5428, 183.1517, 169.2941, 159.8024, 141.5961, 135.5712, 132.5916, 124.3307, 120.4710, 115.3678, 109.3554, 68.1530, 57.1296, 45.2007, 24.6262.

Compound 46. N-(5-methoxy-7,8-dioxo-7,8-dihydronaphthalen-1-yl)acetamide

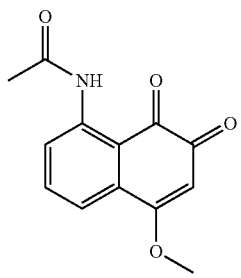 [SMILES: COC1=CC(=O)C(=O)c2c(NC(C)=O)cccc21]

The procedure is the similar as described in 1.2 of Protocol I. ¹H NMR (400 MHz, chloroform-d) δ 11.92 (s, 1H), 8.91 (dd, J=8.5, 1.4 Hz, 1H), 7.85-7.47 (m, 2H), 5.96 (s, 1H), 4.00 (s, 3H), 2.29 (s, 3H). ¹³C NMR (101 MHz, CDCl3) δ 182.1041, 178.2721, 170.0363, 168.4696, 144.2676, 137.0773, 132.3875, 123.6360, 119.9871, 114.5510, 102.4413, 56.9286, 25.6785.

Compound 47. N-(5-methoxy-6-methyl-7,8-dioxo-7,8-dihydronaphthalen-1-yl)acetamide

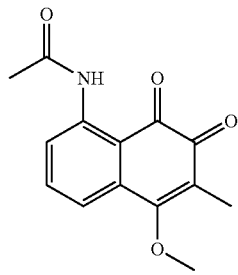 [SMILES: COC1=C(C)C(=O)C(=O)c2c(NC(C)=O)cccc21]

The procedure is the similar as described in 1.2 of Protocol I. ¹H NMR (400 MHz, chloroform-d) δ 11.82 (s, 1H), 9.01 (dd, J=8.6, 1.2 Hz, 1H), 7.83 (dd, J=7.6, 1.2 Hz, 1H), 7.67 (dd, J=8.6, 7.6 Hz, 1H), 4.05 (s, 3H), 2.31 (s, 3H), 2.10 (s, 3H). ¹³C NMR (101 MHz, CDCl₃) δ 185.3045, 184.8583, 169.8293, 158.0858, 141.2284, 135.5041, 132.4520, 132.4232, 125.4810, 121.7681, 115.4664, 61.2983, 25.6834, 9.3750.

Compound 48. N-(5-(2,5,8,11-tetraoxatridecan-13-yloxy)-7,8-dioxo-7,8-dihydronaphthalen-1-yl)acetamide

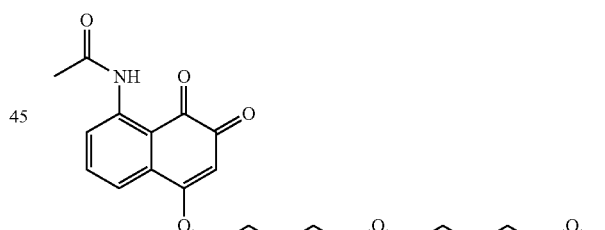

The procedure is the similar as described in 1.2 of Protocol I. ¹H NMR (400 MHz, chloroform-d) δ 11.89 (s, 1H), 8.88 (dd, J=6.4, 3.5 Hz, 1H), 7.66-7.60 (m, 2H), 5.92 (s, 1H), 4.34-4.21 (m, 2H), 3.99-3.90 (m, 2H), 3.75-3.70 (m, 2H), 3.69-3.58 (m, 10H), 3.54-3.49 (m, 2H), 3.34 (s, 3H), 2.26 (s, 3H). ¹³C NMR (101 MHz, CDCl₃) δ 182.0062, 178.2636, 170.0020, 167.6071, 144.2156, 137.0616, 132.3546, 123.5844, 120.1634, 114.5169, 102.9839, 71.8839, 70.9276, 70.6299, 70.6158, 70.5797, 70.4996, 69.2575, 68.6307, 59.0089, 25.6589.

Compound 49. N-(5-(2-(2-methoxyethoxy)ethoxy)-7,8-dioxo-7,8-dihydronaphthalen-1-yl)acetamide

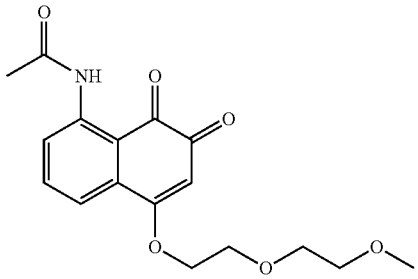 [SMILES: COCCOCCOC1=CC(=O)C(=O)c2c(NC(C)=O)cccc21]

The procedure is the similar as described in 1.2 of Protocol I. $^1$H NMR (400 MHz, chloroform-d) δ 11.89 (s, 1H), 8.89 (dd, J=5.4, 4.4 Hz, 1H), 7.74-7.54 (m, 2H), 5.92 (s, 1H), 4.36-4.17 (m, 2H), 4.08-3.88 (m, 2H), 3.79-3.66 (m, 2H), 3.64-3.50 (m, 2H), 3.38 (s, 3H), 2.27 (s, 3H). $^{13}$C NMR (101 MHz, CDCl$_3$) δ 181.9948, 178.2639, 170.0092, 167.5904, 144.2209, 137.0495, 132.3451, 123.5949, 120.1686, 114.5162, 102.9889, 71.9005, 70.8825, 69.1763, 68.6609, 59.1254, 25.6624.

Compound 50. N-(5-butoxy-7,8-dioxo-7,8-dihydronaphthalen-1-yl)acetamide

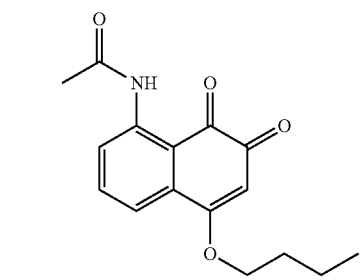 [SMILES: CCCCOC1=CC(=O)C(=O)c2c(NC(C)=O)cccc21]

The procedure is the similar as described in 1.2 of Protocol I. $^1$H NMR (400 MHz, chloroform-d) δ 11.93 (s, 1H), 8.91 (dd, J=8.3, 1.5 Hz, 1H), 7.83-7.50 (m, 2H), 5.94 (s, 1H), 4.13 (t, J=6.4 Hz, 2H), 2.29 (s, 3H), 1.99-1.81 (m, 2H), 1.61-1.50 (m, 2H), 1.02 (t, J=7.4 Hz, 3H). $^{13}$C NMR (101 MHz, CDCl$_3$) δ 182.2277, 178.3326, 170.0388, 167.8021, 144.1966, 137.0237, 132.6501, 123.5576, 119.9068, 114.6513, 102.8517, 69.8295, 30.4294, 25.6787, 19.2643, 13.7086.

Compound 51. N-(5-(octyloxy)-7,8-dioxo-7,8-dihydronaphthalen-1-yl)acetamide

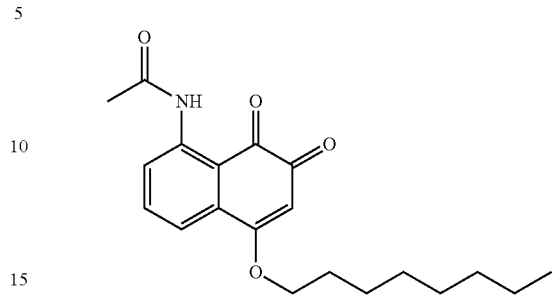

The procedure is the similar as described in 1.2 of Protocol I. $^1$H NMR (400 MHz, chloroform-d) δ 11.90 (s, 1H), 8.89 (dq, J=8.5, 1.4 Hz, 1H), 7.81-7.47 (m, 2H), 5.91 (d, J=1.4 Hz, 1H), 4.10 (t, J=6.4 Hz, 2H), 2.27 (t, J=1.2 Hz, 3H), 2.01-1.78 (m, 2H), 1.48 (q, J=7.5 Hz, 2H), 1.45-1.17 (m, 8H), 0.87 (t, J=6.6 Hz, 3H). $^{13}$C NMR (101 MHz, CDCl$_3$) δ 182.1952, 178.2857, 170.0123, 167.7746, 144.1648, 137.0009, 132.6296, 123.5155, 119.8923, 114.6194, 102.8426, 70.1481, 31.7263, 29.1614, 29.1197, 28.4119, 25.9910, 25.6609, 22.6073, 14.0753.

Compound 52. N-(7,8-dioxo-5-(pentan-3-yloxy)-7,8-dihydronaphthalen-1-yl)acetamide

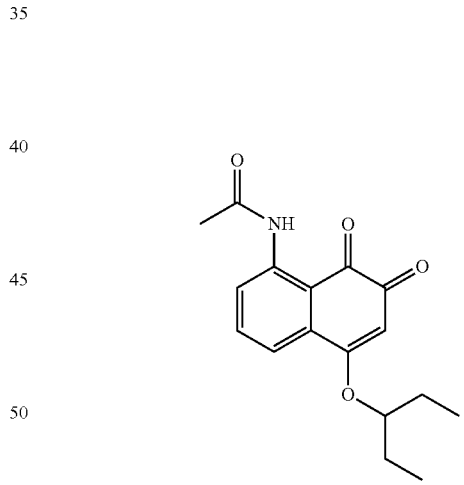

The procedure is the similar as described in 1.2 of Protocol I. $^1$H NMR (400 MHz, chloroform-d) δ 11.92 (s, 1H), 8.89 (dd, J=6.8, 3.0 Hz, 1H), 7.67-7.60 (m, 2H), 5.90 (d, J=0.7 Hz, 1H), 4.31 (p, J=5.8 Hz, 1H), 1.79 (qdd, J=7.3, 5.9, 1.1 Hz, 4H), 0.97 (t, J=7.5 Hz, 6H). $^{13}$C NMR (101 MHz, CDCl$_3$) δ 182.3528, 169.9921, 167.1886, 144.0950, 136.9670, 132.9767, 123.5130, 119.9072, 114.8017, 103.2026, 82.9332, 25.6628, 25.6446, 9.4519.

Compound 53. N-(7,8-dioxo-5-(pentan-3-yloxy)-7,8-dihydronaphthalen-1-yl)methanesulfonamide

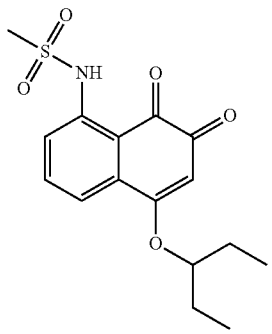 [SMILES: CCC(CC)OC1=CC(=O)C(=O)c2c(NS(C)(=O)=O)cccc21]

The procedure is the similar as described in 1.2 of Protocol I. $^1$H NMR (400 MHz, chloroform-d) δ 11.49 (s, 1H), 7.92 (dd, J=6.8, 2.9 Hz, 1H), 7.70-7.66 (m, 2H), 5.95 (d, J=0.7 Hz, 1H), 4.33 (p, J=5.8 Hz, 1H), 3.14 (s, 3H), 1.97-1.74 (m, 4H), 0.99 (t, J=7.5 Hz, 6H). $^{13}$C NMR (101 MHz, CDCl$_3$) δ 181.9371, 178.1000, 166.6461, 143.3780, 137.1017, 133.8990, 120.2937, 119.8970, 114.9450, 103.6855, 83.1530, 40.9901, 25.6630, 9.4649.

Compound 54. N-(5-(hexyloxy)-7,8-dioxo-7,8-dihydronaphthalen-1-yl)methanesulfonamide

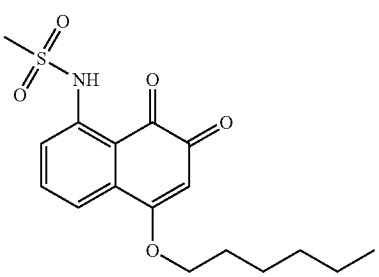 [SMILES: CCCCCCOC1=CC(=O)C(=O)c2c(NS(C)(=O)=O)cccc21]

The procedure is the similar as described in 1.2 of Protocol I. $^1$H NMR (400 MHz, CDCl$_3$) δ 11.49 (s, 1H), 7.93 (dd, J=8.3, 1.3 Hz, 1H), 7.79-7.60 (m, 2H), 5.97 (s, 1H), 4.14 (t, J=6.4 Hz, 2H), 3.15 (s, 3H), 1.92 (dt, J=14.6, 6.6 Hz, 2H), 1.50 (q, J=7.1 Hz, 2H), 1.38 (m, 4H), 1.02-0.82 (m, 3H). $^{13}$C NMR (101 MHz, DMSO-d$_6$) δ 177.0225, 173.2754, 162.4683, 138.6884, 132.3872, 128.7840, 115.4609, 115.1004, 109.9593, 98.5735, 65.5379, 36.2744, 26.6056, 23.6124, 20.9061, 17.7573, 9.2335.

Compound 55. N-(5-(octyloxy)-7,8-dioxo-7,8-dihydronaphthalen-1-yl)methanesulfonamide

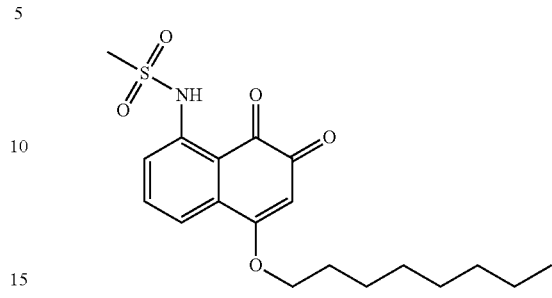

The procedure is the similar as described in 1.2 of Protocol I. $^1$H NMR (400 MHz, chloroform-d) δ 11.47 (s, 1H), 7.91 (dd, J=8.3, 1.3 Hz, 1H), 7.78-7.56 (m, 2H), 5.96 (s, 1H), 4.13 (t, J=6.4 Hz, 2H), 3.15 (s, 3H), 1.98-1.86 (m, 2H), 1.56-1.45 (m, 2H), 1.44-1.22 (m, 8H), 0.93-0.84 (m, 3H). $^{13}$C NMR (101 MHz, CDCl$_3$) δ 181.7744, 178.0271, 167.2173, 143.4410, 137.1266, 133.5402, 120.2214, 119.8531, 114.7165, 103.3252, 70.2918, 41.0282, 31.7357, 29.1609, 29.1299, 28.3942, 25.9849, 22.6172, 14.0880.

Compound 56. N-(5-(2,5,8,11-tetraoxatridecan-13-yloxy)-7,8-dioxo-7,8-dihydronaphthalen-1-yl)methanesulfonamide

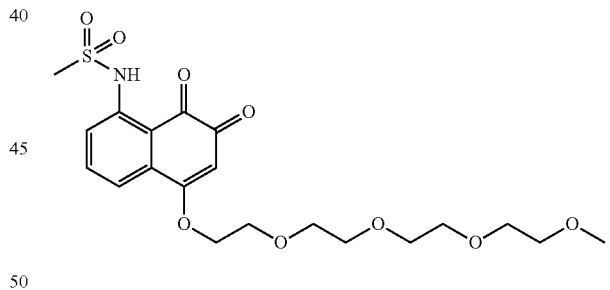

The procedure is the similar as described in 1.2 of Protocol I. $^1$H NMR (400 MHz, chloroform-d) δ 11.48 (s, 1H), 7.95-7.88 (m, 1H), 7.71-7.67 (m, 2H), 5.97 (s, 1H), 4.32-4.23 (m, 2H), 4.00-3.94 (m, 2H), 3.78-3.72 (m, 2H), 3.72-3.57 (m, 11H), 3.57-3.45 (m, 2H), 3.37 (s, 3H), 3.15 (s, 3H). $^{13}$C NMR (101 MHz, CDCl$_3$) δ 181.5953, 178.0174, 167.0722, 143.5023, 137.1757, 133.2725, 120.3051, 120.1397, 114.6306, 103.4732, 71.8981, 70.9379, 70.6388, 70.6251, 70.5886, 70.5118, 69.3579, 68.6253, 59.0318, 41.0669.

Compound 57.
5,8-dihydroxy-4-isopropoxynaphthalene-1,2-dione

57.1. Synthesis of 2-(dimethylamino)-5,8-dihydroxynaphthalene-1,4-dione

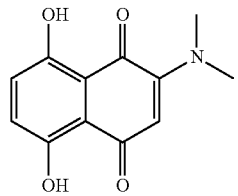 [SMILES: CN(C)C1=CC(=O)c2c(O)ccc(O)c2C1=O]

The procedure is the similar as described in III.1 of Protocol III. $^1$H NMR (400 MHz, acetone-$d_6$) δ 13.52 (s, 1H), 12.05 (d, J=2.9 Hz, 1H), 7.26 (d, J=9.3 Hz, 1H), 7.16 (d, J=9.3 Hz, 1H), 5.79 (s, 1H), 3.33 (s, 6H).

57.2. Synthesis of 2,5,8-trihydroxynaphthalene-1,4-dione

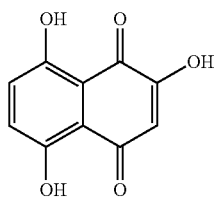 [SMILES: O=C1C=C(O)C(=O)c2c(O)ccc(O)c21]

The procedure is the similar as described in 111.2 of Protocol III. $^1$H NMR (400 MHz, acetone-$d_6$) δ 12.80 (d, J=1.7 Hz, 1H), 11.75 (d, J=1.6 Hz, 1H), 10.30 (s, 1H), 7.38 (d, J=9.4 Hz, 1H), 7.30 (d, J=9.4 Hz, 1H), 6.30 (s, 1H).

57.3. Synthesis of 5,8-dihydroxy-4-isopropoxynaphthalene-1,2-dione

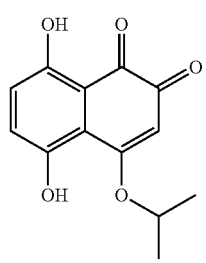 [SMILES: CC(C)OC1=CC(=O)C(=O)c2c(O)ccc(O)c21]

The procedure is the similar as described in 1.2 of Protocol I. $^1$H NMR (400 MHz, chloroform-d) δ 12.90 (s, 1H), 8.95 (s, 1H), 7.20 (d, J=9.4 Hz, 1H), 7.10 (d, J=9.4 Hz, 1H), 5.97 (s, 1H), 4.85 (p, J=6.1 Hz, 1H), 1.56 (d, J=6.1 Hz, 6H). $^{13}$C NMR (101 MHz, CDCl$_3$) δ 182.3884, 178.8085, 168.0537, 162.5333, 151.0231, 132.1499, 125.6905, 112.3409, 110.1269, 103.8639, 75.1156, 121.7424.

Compound 58. 8-(N-acetylacetamido)-4-isopropoxynaphthalene-1,2-diyl diacetate

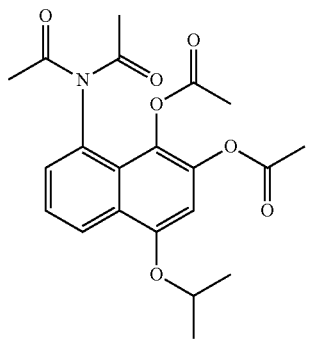 [SMILES: CC(=O)Oc1cc(OC(C)C)c2cccc(N(C(C)=O)C(C)=O)c2c1OC(C)=O]

The mixture of N-(5-isopropoxy-7,8-dioxo-7,8-dihydronaphthalen-1-yl)acetamide (30 mg, 1 equivalent), zinc powder (36 mg, 5 equivalents), and NaOAc (4.5 mg, 0.5 equivalent) in Ac$_2$O (0.5 mL) was stirred at 110° C. for 1 hour. After cooled down to room temperature, the mixture was filtered through a pad of Celite®, and washed with EtOAc. After removal of solvents in vacuo, the residue was dissolved in DCM and washed with brine. After drying over MgSO$_4$ and concentration in sequence, the residue was purified through recrystallization from $^i$PrOH. A white needle solid is afforded. $^1$H NMR (400 MHz, DMSO-$d_6$) δ 8.29 (dd, J=7.6, 2.2 Hz, 1H), 7.68-7.49 (m, 2H), 7.07 (s, 1H), 4.79 (p, J=6.0 Hz, 1H), 2.27 (d, J=0.9 Hz, 6H), 2.14 (s, 6H), 1.39 (d, J=5.9 Hz, 6H). $^{13}$C NMR (101 MHz, CDCl$_3$) δ 173.0548, 168.7322, 167.9453, 152.2335, 141.1343, 133.4654, 130.3043, 128.7775, 126.7335, 125.0539, 124.8899, 124.6943, 103.0551, 71.2407, 27.0006, 21.8850, 20.8742, 20.5808.

Compound 59.
8-acetamido-4-isopropoxynaphthalene-1,2-diyl diacetate

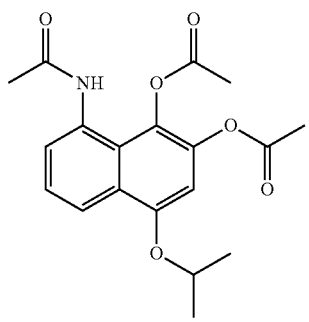 [SMILES: CC(=O)Nc1cccc2c(OC(C)C)cc(OC(C)=O)c(OC(C)=O)c12]

The mixture of N-(5-isopropoxy-7,8-dioxo-7,8-dihydronaphthalen-1-yl)acetamide (0.5 g, 1 equivalent), zinc powder (0.598 g, 5 equivalents), NaOAc (75 mg, 0.5 equivalent), and Ac$_2$O (1.72 mL, 10 equivalents) in DMF (1 mL) was stirred at room temperature for 1 hour. After cooled down to room temperature, the mixture was filtered through a pad of Celite®, and washed with EtOAc. After removal of solvents in vacuo, the residue was dissolved in DCM and washed with brine. After dried over MgSO$_4$ and concentrated in sequence, the residue was purified through silica gel column chromatography, and the solid was recrystallized from ⁱPrOH. A white needle solid was afforded. ¹H NMR (400 MHz, DMSO-d₆) δ 9.78 (s, 1H), 8.09 (d, J=8.1 Hz, 1H), 7.45 (dt, J=13.1, 7.4 Hz, 2H), 6.97 (s, 1H), 4.77 (p, J=6.0 Hz, 1H), 2.32 (s, 3H), 2.29 (s, 3H), 2.06 (s, 3H), 1.37 (d, J=6.0 Hz, 6H). ¹³C NMR (101 MHz, DMSO) δ 169.0052, 168.8106, 151.5242, 140.7894, 132.3983, 129.9567, 127.8955, 126.1240, 125.4083, 124.3424, 120.8935, 103.6967, 71.1217, 23.5963, 22.0826, 20.9664, 20.7807.

Compound 60.
8-acetamido-4-isopropoxynaphthalene-1,2-diyl dipropionate

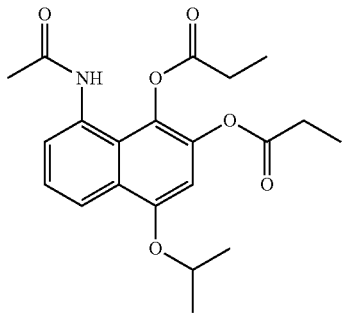 [SMILES: CCC(=O)Oc1cc(OC(C)C)c2cccc(NC(C)=O)c2c1OC(=O)CC]

The procedure is similar as described in Example 59. ¹H NMR (400 MHz, acetone-d₆) δ 9.15 (s, 1H), 8.12 (d, J=8.4 Hz, 1H), 7.96 (d, J=7.8 Hz, 1H), 7.45 (t, J=8.5 Hz, 1H), 6.92 (s, 1H), 4.81 (hept, J=6.1 Hz, 1H), 2.77 (q, J=9.2, 7.6 Hz, 2H), 2.64 (q, J=7.5 Hz, 2H), 2.21 (s, 2H), 1.22 (dt, J=11.0, 7.3 Hz, 5H). ¹³C NMR (101 MHz, acetone) δ 171.3562, 167.5906, 151.6193, 140.6662, 132.7607, 130.0531, 126.2848, 124.7471, 124.2166, 122.3050, 119.5244, 103.0617, 70.8921, 26.8655, 23.4156, 21.1746, 8.3932.

Compound 61. 4-isopropoxy-8-(methylsulfonamido) naphthalene-1,2-diyl dipropionate

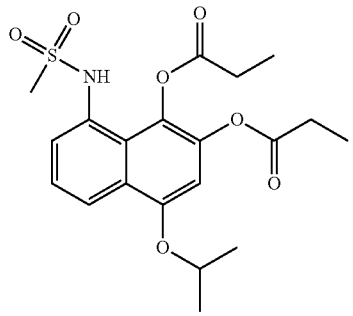 [SMILES: CCC(=O)Oc1cc(OC(C)C)c2cccc(NS(C)(=O)=O)c2c1OC(=O)CC]

To a dry flask were added starting material N-(5-isopropoxy-7,8-dioxo-7,8-dihydronaphthalen-1-yl)methanesulfonamide (200 mg, 0.646 mmol, 1.0 eq.), NaOAc (53 mg, 0.646 mmol, 1.0 eq.), zinc powder (422 mg, 6.46 mmol, 10 eq.), ethyl acetate (10 mL) and propionic anhydride (181 uL, 1.42 mmol, 2.2 eq.). The resulting reaction mixture was heated to reflux for 3 hrs. No starting material left, which was monitored by TLC. The reaction mixture was filtered through a pad of Celite®, washed with ethyl acetate (3×5 mL). The combined filtrate was concentrated. The crude was purified by silica gel flash chromatography (10%-20% ethyl acetate/hexanes) to afford 102 mg of desired product with 37% yield. The structure of desired product was confirmed by ¹H NMR, ¹³C NMR and LC-MS. ¹H NMR (400 MHz, chloroform-d) δ 8.16 (dd, J=8.5, 1.1 Hz, 1H), 8.00 (s, 1H), 7.73 (dd, J=7.7, 1.1 Hz, 1H), 7.41 (dd, J=8.5, 7.6 Hz, 1H), 6.71 (s, 1H), 4.69 (hept, J=6.1 Hz, 1H), 2.90 (s, 3H), 2.80 (q, J=7.5 Hz, 2H), 2.60 (q, J=7.5 Hz, 2H), 1.46 (d, J=6.0 Hz, 6H), 1.34 (t, J=7.5 Hz, 3H), 1.29 (t, J=7.6 Hz, 3H). ¹³C NMR (101 MHz, chloroform-d) δ 171.82, 171.78, 152.45, 140.68, 131.77, 129.16, 126.93, 125.46, 120.48, 120.31, 120.03, 103.04, 71.44, 38.90, 27.74, 27.69, 22.02, 9.17, 9.13. LC-MS (M+Na⁺)=446.6

Compound 62. 4-isopropoxy-8-(N-(methylsulfonyl) propionamido)naphthalene-1,2-diyl dipropionate

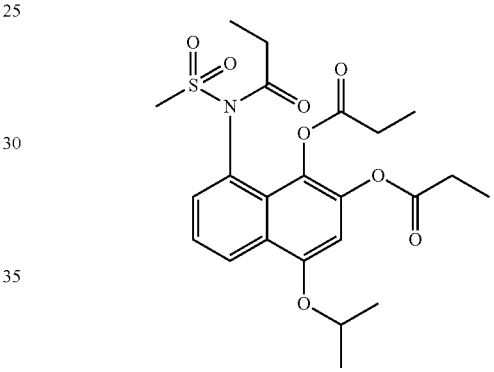

To a dry flask were added starting material N-(5-isopropoxy-7,8-dioxo-7,8-dihydronaphthalen-1-yl)methanesulfonamide (309 mg, 1.0 mmol, 1.0 eq.), NaOAc (16.4 mg, 0.20 mmol, 0.2 eq.), zinc powder (327 mg, 5.0 mmol, 10 eq.) and propionic anhydride (3 mL). The resulting reaction mixture was stirred at room temperature for 18 hrs and warmed to 50° C. for 1 hour. No starting material left, which was monitored by TLC. The reaction mixture was filtered through a pad of Celite®, washed with ethyl acetate (3×5 mL). The combined filtrate was concentrated under high vacuum pump. The crude was purified by silica gel flash chromatography (10%-20% ethyl acetate/hexanes) to afford 380 mg of desired product with 79% yield. The structure of desired product was confirmed by ¹H NMR, ¹³C NMR and LC-MS. ¹H NMR (400 MHz, chloroform-d) δ 8.48 (dd, J=8.5, 1.3 Hz, 1H), 7.46 (dd, J=8.5, 7.3 Hz, 1H), 7.37 (dd, J=7.3, 1.3 Hz, 1H), 6.81 (s, 1H), 4.71 (hept, J=6.1 Hz, 1H), 3.49 (s, 3H), 2.84-2.62 (m, 2H), 2.62-2.50 (m, 2H), 2.12-2.05 (m, 2H), 1.46 (dd, J=7.5, 6.0 Hz, 6H), 1.26 (t, J=6.6 Hz, 3H), 1.22 (t, J=6.5 Hz, 3H), 0.97 (t, J=7.2 Hz, 3H). ¹³C NMR (101 MHz, chloroform-d) δ 175.41, 171.50, 152.06, 141.76, 131.56, 129.44, 129.02, 126.91, 126.23, 126.12, 124.55, 103.73, 71.42, 41.75, 30.57, 27.75, 27.38, 22.01, 21.96, 9.06, 9.00, 8.39. LC-MS (M+Na⁺)=502.5

Compound 63. 4-isopropoxy-8-(N-(methylsulfonyl)acetamido)naphthalene-1,2-diyl diacetate

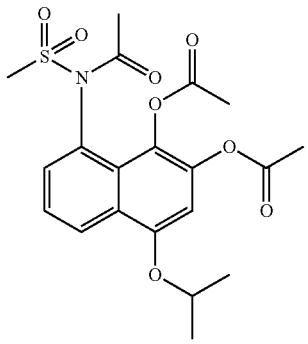 [SMILES: CC(=O)Oc1cc(OC(C)C)c2cccc(N(C(C)=O)S(C)(=O)=O)c2c1OC(C)=O]

To a dry flask were added starting material N-(5-isopropoxy-7,8-dioxo-7,8-dihydronaphthalen-1-yl)methanesulfonamide (309 mg, 1.0 mmol, 1.0 eq.), NaOAc (16.4 mg, 0.20 mmol, 0.2 eq.), zinc powder (327 mg, 5.0 mmol, 10 eq) and acetic anhydride (3 mL). The resulting reaction mixture was stirred at room temperature for 18 hrs. No starting material left, which was monitored by TLC. The reaction mixture was filtered through a pad of Celite®, washed with ethyl acetate (3×5 mL). The combined filtrate was concentrated under high vacuum pump. The crude was purified by silica gel flash chromatography (10%-20% i-Propanol/hexanes) to afford 417 mg of desired product with 95% yield. The structure of desired product was confirmed by $^1$H NMR, $^{13}$C NMR and LC-MS. $^1$H NMR (400 MHz, chloroform-d) δ 8.49 (dd, J=8.5, 1.3 Hz, 1H), 7.48 (dd, J=8.5, 7.3 Hz, 1H), 7.39 (dd, J=7.3, 1.3 Hz, 1H), 6.81 (s, 1H), 4.71 (hept, J=6.1 Hz, 1H), 3.49 (s, 3H), 2.40 (s, 3H), 2.31 (s, 3H), 1.92 (s, 3H), 1.47 (dd, J=7.6, 6.0 Hz, 6H). $^{13}$C NMR (101 MHz, chloroform-d) δ 172.17, 168.05, 152.27, 141.79, 131.40, 130.12, 129.00, 126.99, 126.24, 126.09, 124.67, 103.61, 71.50, 41.73, 25.12, 22.05, 21.96, 21.04, 21.00. LC-MS (M+Na$^+$)=460.3

Compound 64. 4-isopropoxy-8-(methylsulfonamido)naphthalene-1,2-diyl diacetate

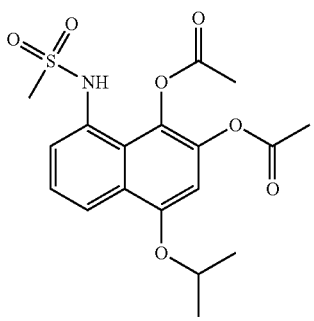 [SMILES: CC(=O)Oc1cc(OC(C)C)c2cccc(NS(C)(=O)=O)c2c1OC(C)=O]

To a dry flask were added starting material N-(5-isopropoxy-7,8-dioxo-7,8-dihydronaphthalen-1-yl)methanesulfonamide (200 mg, 0.646 mmol, 1.0 eq.), NaOAc (53 mg, 0.646 mmol, 1.0 eq.), zinc powder (422 mg, 6.46 mmol, 10 eq.), ethyl acetate (10 mL) and acetic anhydride (134 µL, 1.42 mmol, 2.2 eq.). The resulting reaction mixture was heated to reflux for 3 hrs. No starting material left, which was monitored by TLC. The reaction mixture was filtered through a pad of Celite®, washed with ethyl acetate (3×5 mL). The combined filtrate was concentrated. The crude was purified by silica gel flash chromatography (10%-15% i-Propanol/hexanes) to afford 92 mg of desired product with 36% yield. The structure of desired product was confirmed by $^1$H NMR, $^{13}$C NMR and LC-MS. $^1$H NMR (400 MHz, chloroform-d) δ 8.16 (dd, J=8.6, 1.2 Hz, 1H), 7.93 (s, 1H), 7.73 (dd, J=7.7, 1.2 Hz, 1H), 7.42 (dd, J=8.6, 7.6 Hz, 1H), 6.70 (s, 1H), 4.69 (hept, J=6.0 Hz, 1H), 2.92 (s, 3H), 2.50 (s, 3H), 2.33 (s, 3H), 1.46 (d, J=6.0 Hz, 6H). $^{13}$C NMR (101 MHz, chloroform-d) δ 168.37, 168.30, 152.59, 140.71, 131.67, 129.12, 126.99, 125.54, 120.63, 120.39, 120.36, 102.90, 71.48, 39.03, 22.02, 20.98, 20.89. LC-MS (M+Na$^+$)=418.5

Compound 65. 7-chloro-4-isopropoxynaphthalene-1,2-diyl diacetate

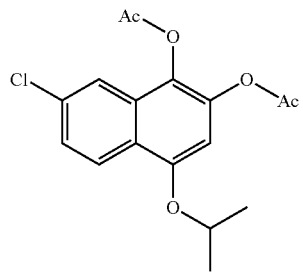 [SMILES: CC(=O)Oc1cc(OC(C)C)c2ccc(Cl)cc2c1OC(C)=O]

The mixture of N-(5-isopropoxy-7,8-dioxo-7,8-dihydronaphthalen-1-yl)acetamide (5.9 mg, 1 equivalent), zinc powder (7.7 mg, 5 equivalents), and NaOAc (1.9 mg, 1 equivalent) in Ac$_2$O (0.5 mL) was stirred at 50° C. for 2 hours. After cooled down to room temperature, the mixture was filtered through a pad of Celite®, and washed with EtOAc. After removal of solvents in vacuo, the residue was dissolved in DCM and washed with brine. After dried over MgSO$_4$ and concentrated in sequence, the residue was purified through a silica gel TLC plate to give a white solid. $^1$H NMR (400 MHz, chloroform-d) δ 8.19 (dd, J=9.1, 0.6 Hz, 1H), 7.70 (dd, J=2.2, 0.6 Hz, 1H), 7.38 (dd, J=9.0, 2.1 Hz, 1H), 6.63 (d, J=0.7 Hz, 1H), 4.67 (p, J=6.0 Hz, 1H), 2.44 (s, 3H), 2.33 (s, 3H), 1.44 (d, J=6.0 Hz, 6H). $^{13}$C NMR (101 MHz, CDCl$_3$) δ 168.5163, 168.3194, 152.1763, 140.1529, 133.9282, 129.0595, 128.8687, 126.0864, 124.7933, 123.2651, 119.9015, 102.2090, 71.1562, 21.8863, 20.8233, 20.4426.

Compound 66. 6-acetamido-4-isopropoxynaphthalene-1,2-diyl diacetate

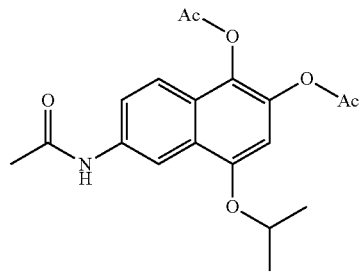 [SMILES: CC(=O)Nc1ccc2c(OC(C)=O)c(OC(C)=O)cc(OC(C)C)c2c1]

The procedure is similar as described in Example 65. $^1$H NMR (400 MHz, chloroform-d) δ 8.08 (q, J=2.1 Hz, 1H), 7.74 (ddt, J=6.7, 4.6, 2.2 Hz, 1H), 7.60 (dt, J=9.2, 3.2 Hz, 1H), 6.57 (d, J=2.1 Hz, 1H), 4.75-4.52 (m, 1H), 2.42 (s, 3H), 2.32 (s, 3H), 2.14 (dd, J=4.0, 2.0 Hz, 3H), 1.53-1.35 (m, 6H). $^{13}$C NMR (101 MHz, CDCl$_3$) δ 168.9008, 168.6341, 168.5567, 151.6363, 138.1247, 135.5324, 129.8439, 125.3663, 124.8394, 121.6458, 121.5494, 111.6646, 102.2844, 70.9915, 24.5015, 21.9156, 20.8180, 20.4628.

Compound 67. 6-((tert-butoxycarbonyl)amino)-4-isopropoxynaphthalene-1,2-diyl diacetate

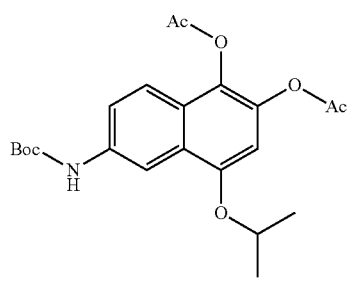 [SMILES: CC(=O)Oc1cc(OC(C)C)c2cc(NC(=O)OC(C)(C)C)ccc2c1OC(C)=O]

The procedure is similar as described in Example 65. $^1$H NMR (400 MHz, chloroform-d) δ 8.19-7.90 (m, 1H), 7.73 (s, 1H), 7.66 (d, J=8.9 Hz, 1H), 6.71 (s, 1H), 6.60 (s, 1H), 4.65 (hept, J=6.1 Hz, 1H), 2.41 (s, 3H), 2.32 (s, 3H), 1.54 (s, 9H), 1.43 (d, J=6.0 Hz, 6H). $^{13}$C NMR (101 MHz, CDCl$_3$) δ 168.6294, 168.6138, 152.7009, 151.3466, 137.7538, 135.9894, 129.8983, 125.6153, 124.3297, 121.9348, 120.6550, 110.0186, 102.3633, 70.8757, 28.3608, 21.9459, 20.8222, 20.4529.

Example 2—Biological Activity

A. Activity of Compounds Relative to β-lapachone

In vitro anti-cancer activity of the compound were performed using ATP Assay Kit (Abcam, ab83355) to initially screen, and further performed using 7-day DNA assay.

Cell culture: endogenous NQO1 overexpressing human MIA PaCa-2 pancreactic and A549 NSCLC cancer cells were obtained (Bey, et al., 2007; Li, et al., 2011). Cancer cells were grown in DMEM with 5% FBS and *Mycoplasma* free, and cultured at 37° C. in a 5% CO$_2$ 95% air humidified atmosphere.

ATP assay: Cells were seeded into each well of a 96-well plate (15000 cells/well) 18 hours ahead of experiment. After aspiration of the media from each well, 100 μl drug-contained media was added instead, and further incubated for 2 hours. After incubation, 100 μl ATP assay kit mixture was added into every well. Following further shaking for 10 minutes with light proof, the data were collected by reading luminescence integrate 1 second per well.

DNA assay: Cells were seeded into each well of a 48-well plate (10000 cells/well) 24 hours ahead of experiment. After aspiration of the media from each well, 500 μl drug-contained media was added instead, and further incubated for 2 hours. Drugs were then removed, control growth medium was added, and cells were allowed to grow for an additional 7 days. Drugs were added to medium at a 1:1000 dilution immediately before administration to cells. DNA content (a measure of cell growth) was determined by fluoresence of the DNA dye Hoescht 33258 (Sigma), and read in a Cytofluor fluoresence plate reader. Data were expressed as relative growth with 6 repetitions.

TABLE 1

Relative activity compare with β-lapachone in ATP depletion of Mia PaCa-2 cells

| Compound | $IC_{50}/IC_{50}$ (β-lapachone/Compound) |
|---|---|
| Compound 1 | <0.3 |
| Compound 2 | <0.3 |
| Compound 3 | <0.3 |
| Compound 4 | 1~2 |
| Compound 5 | <0.3 |
| Compound 6 | <0.3 |
| Compound 7 | 0.3~1 |
| Compound 8 | <0.3 |
| Compound 9 | <0.3 |
| Compound 10 | <0.3 |
| Compound 11 | <0.3 |
| Compound 12 | <0.3 |
| Compound 13 | <0.3 |
| Compound 14 | 0.3~1 |
| Compound 16 | 0.3~1 |
| Compound 17 | <0.3 |
| Compound 19 | <0.3 |
| Compound 20 | <0.3 |
| Compound 21 | >3 |
| Compound 22 | <0.3 |
| Compound 23 | <0.3 |
| Compound 24 | >3 |
| Compound 25 | <0.3 |
| Compound 26 | <0.3 |
| Compound 27 | <0.3 |
| Compound 28 | 1~2 |
| Compound 29 | <0.3 |
| Compound 31 | <0.3 |
| Compound 32 | <0.3 |
| Compound 33 | <0.3 |
| Compound 34 | 1~2 |
| Compound 35 | 0.3~1 |
| Compound 36 | <0.3 |
| Compound 37 | 1~2 |
| Compound 38 | 1~2 |
| Compound 39 | 0.3~1 |
| Compound 40 | <0.3 |
| Compound 42 | <0.3 |
| Compound 43 | 0.3~1 |
| Compound 44 | 0.3~1 |
| Compound 45 | 1~2 |
| Compound 46 | 1~3 |
| Compound 47 | <0.3 |
| Compound 48 | >3 |
| Compound 49 | 0.3~1 |
| Compound 50 | 1~2 |
| Compound 51 | <0.3 |
| Compound 52 | <0.3 |
| Compound 53 | <0.3 |
| Compound 54 | <0.3 |
| Compound 55 | 1~2 |
| Compound 56 | <0.3 |

TABLE 2

Cell viability in A549 cells

| Compound | $IC_{50}/IC_{50}$ (β-lapachone/Compound) |
|---|---|
| Compound 4 | 1~2 |
| Compound 21 | >3 |
| Compound 24 | >3 |
| Compound 28 | 1~2 |
| Compound 34 | 0.3~1 |
| Compound 37 | 0.3~1 |
| Compound 38 | 1~2 |

TABLE 2-continued

Cell viability in A549 cells

| Compound | $IC_{50}/IC_{50}$ (β-lapachone/Compoud) |
|---|---|
| Compound 48 | >3 |
| Compound 49 | 0.3~1 |

Figure 2A:
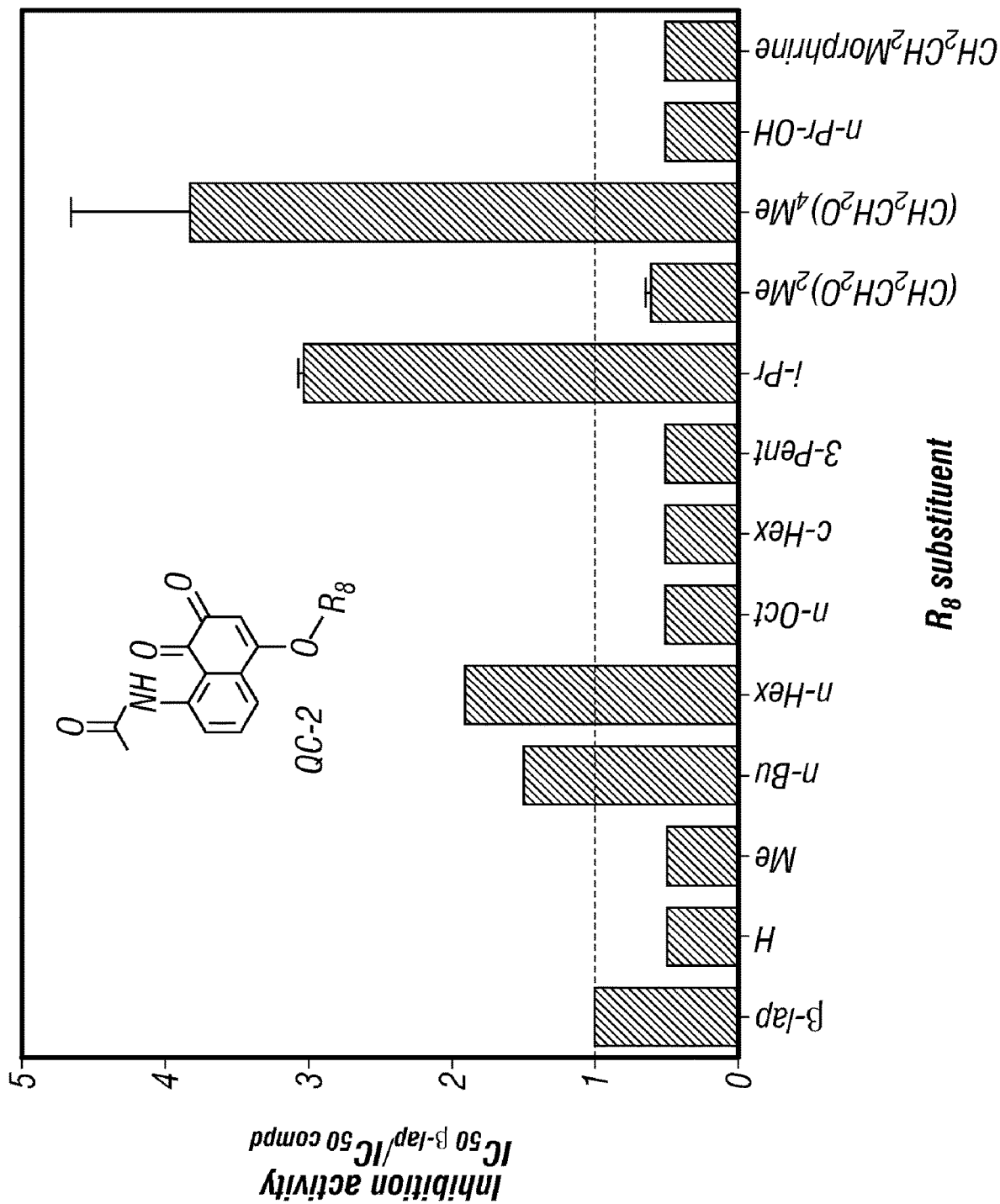
FIGS. 2A & 2B show the activity in MiaPaca2 and A549 cell lines along with NQO1 selectivity of the compounds with an acetylamide group adjacent to the carbonyl with various different groups on the ether group of the adjacent ring. Additionally, the ATP inhibition of the compounds in the MiaPaca-2 cell line is shown in FIG. 2A, and the efficacy and toxicity of the compounds in the A549 cell line is shown in FIG. 2B.
Figure 2B:
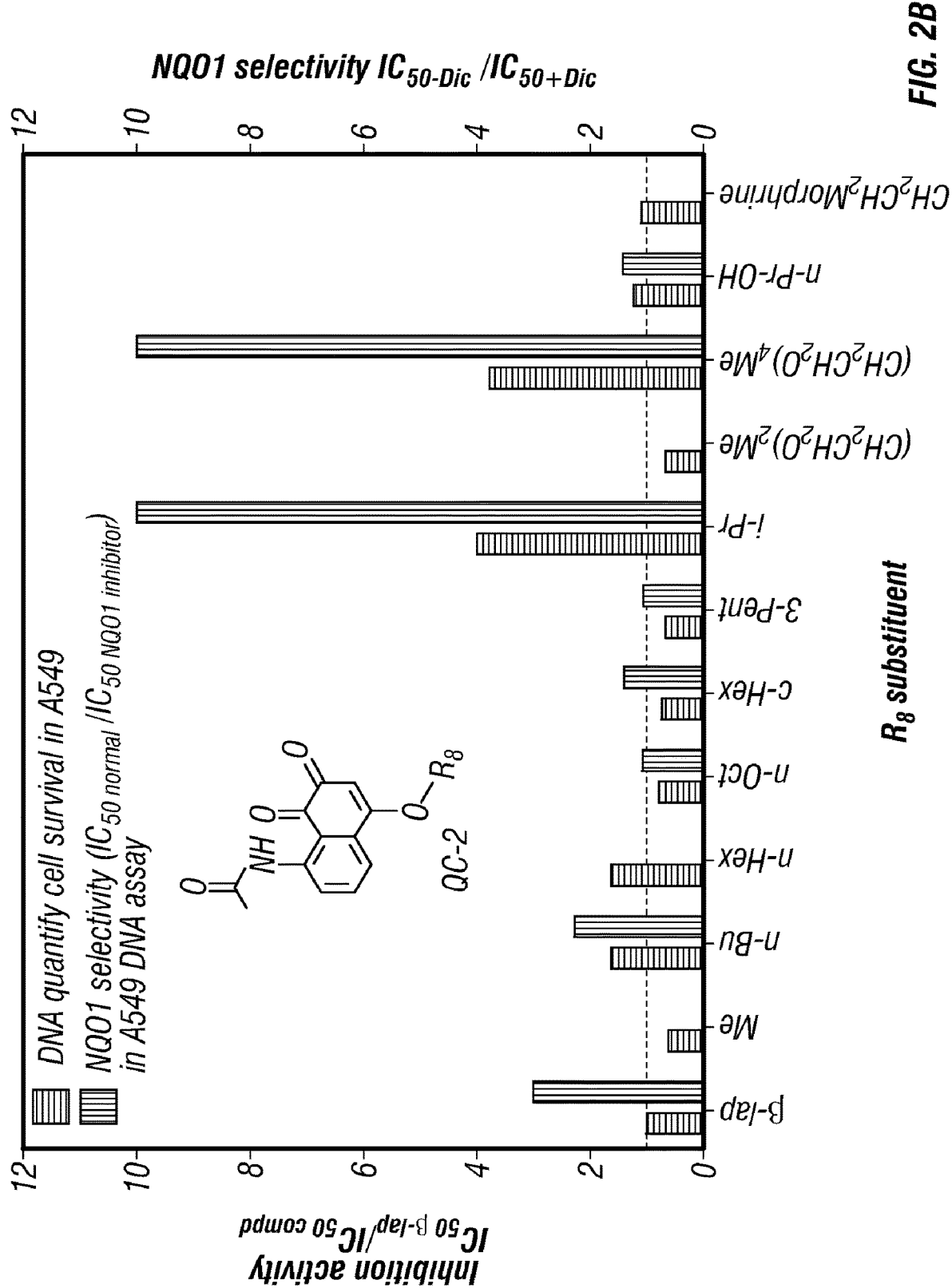
Figure 3A:
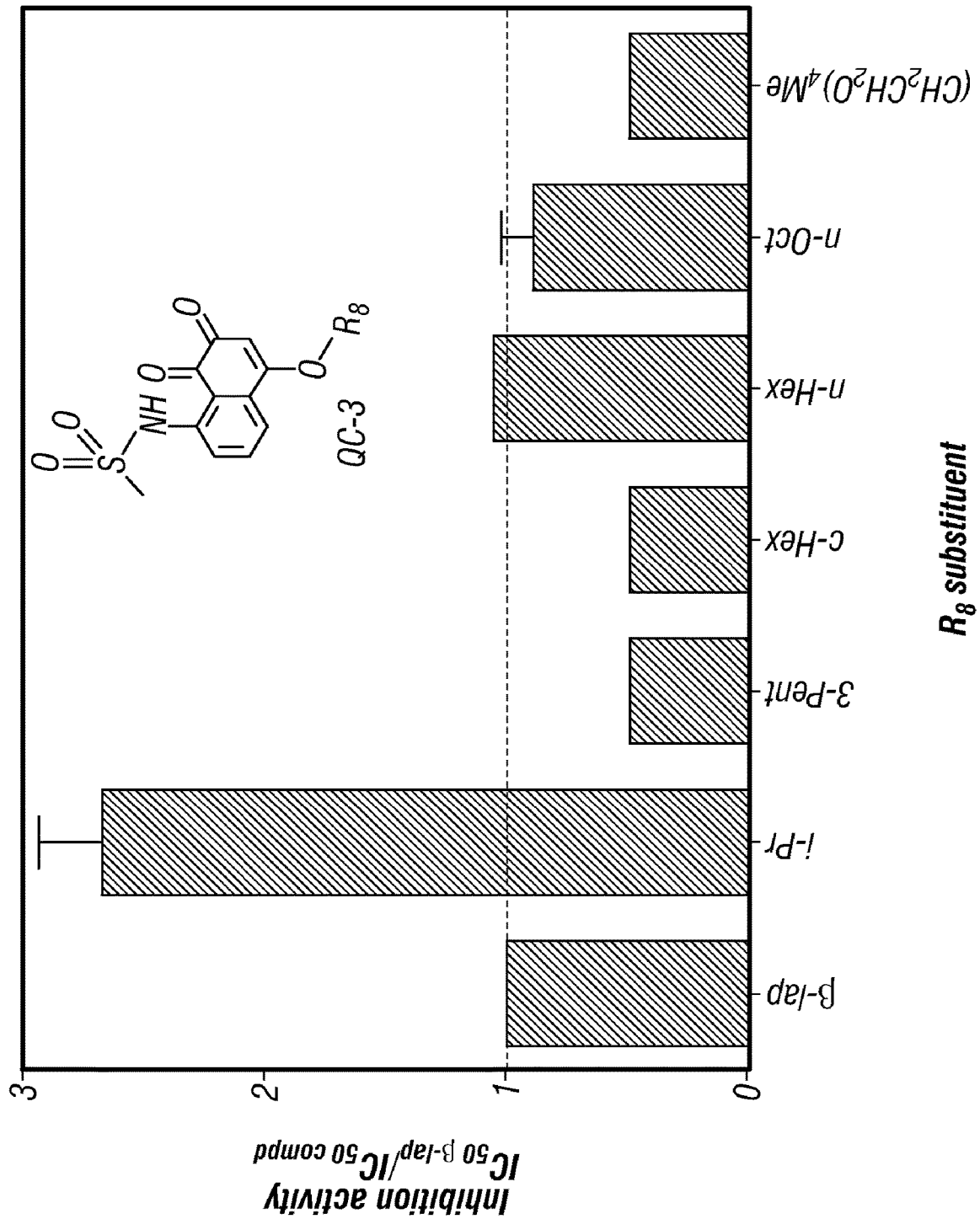
FIGS. 3A & 3B show the activity in MiaPaca2 and A549 cell lines along with NQO1 selectivity of the compounds with a sulfamide group adjacent to the carbonyl with various different groups on the ether group of the adjacent ring. Additionally, the ATP inhibition of the compounds in the MiaPaca-2 cell line is shown in FIG. 3A, and the efficacy and toxicity of the compounds in the A549 cell line is shown in FIG. 3B.
Figure 3B:
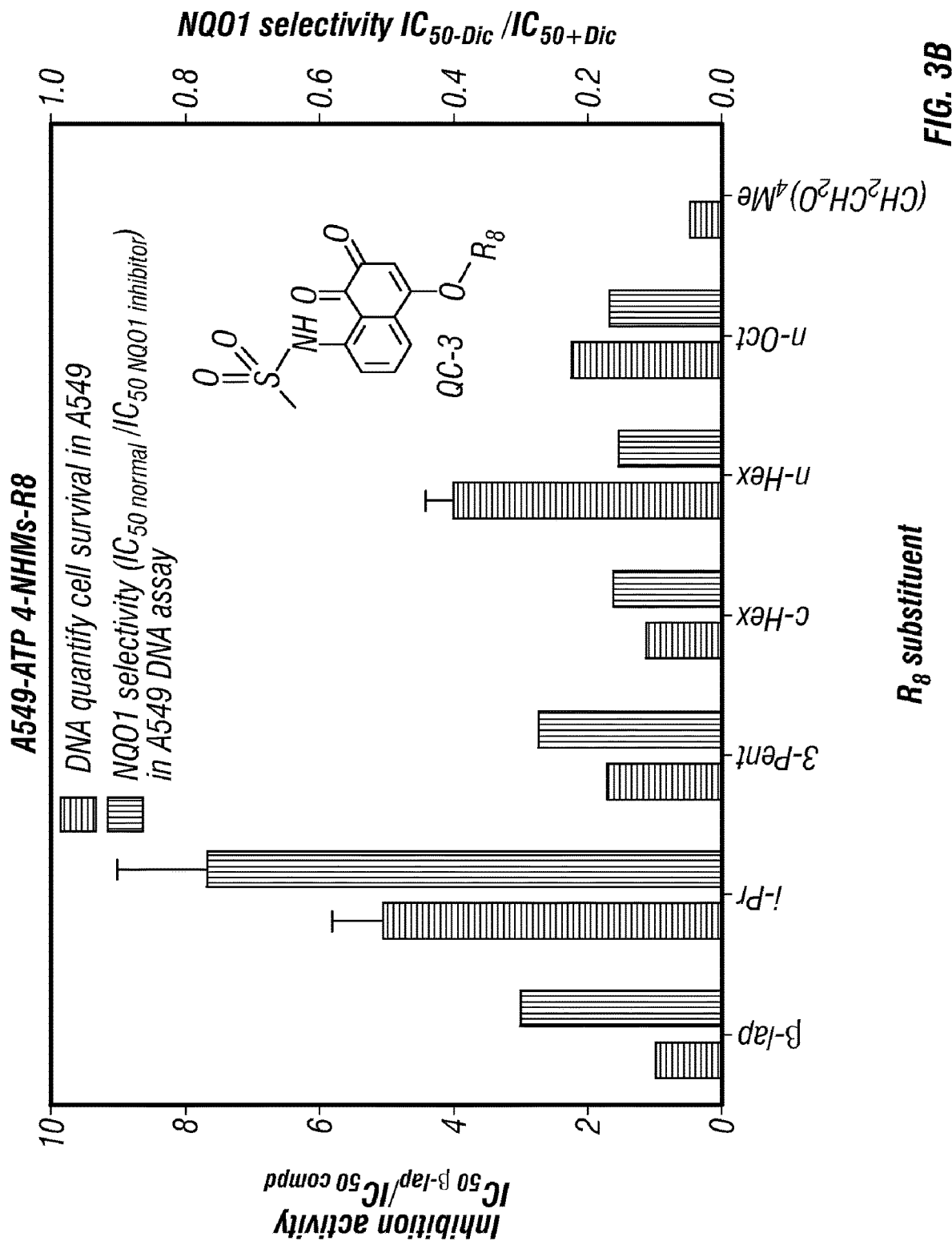
Figure 4A:
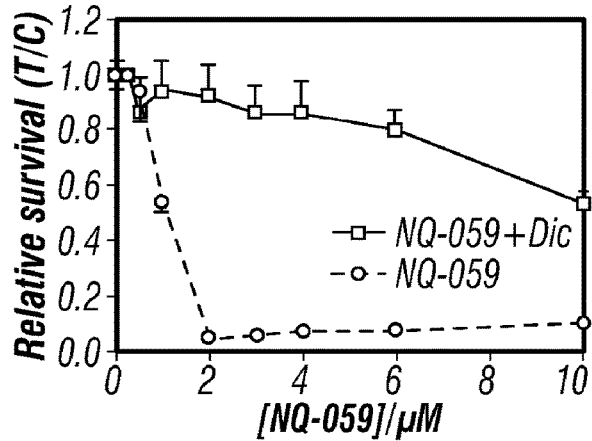
FIGS. 4A-4J shows the cell survival in the absence and presence of the NQO1 inhibitor, DIC, for compound NQ-059 in a MiaPaca-2 cell line (FIG. 4A), compound NQ-081 in a MiaPaca-2 cell line (FIG. 4B), β-lapachone in a MiaPaca-2 cell line (FIG. 4C), compound NQ-059 in a MCF-7 cell line (FIG. 4D), compound NQ-081 in a MCF-7 cell line (FIG. 4E), β-lapachone in a MCF-7 cell line (FIG. 4F), compound NQ-059 in an A549 cell line (FIG. 4G), compound NQ-081 in a A549 cell line (FIG. 4H), or β-lapachone in an A549 cell line (FIG. 4I), or compounds NQ-059 and β-lapachone in an NQO1 negative H596 cell line (FIG. 4J).
Figure 4B:
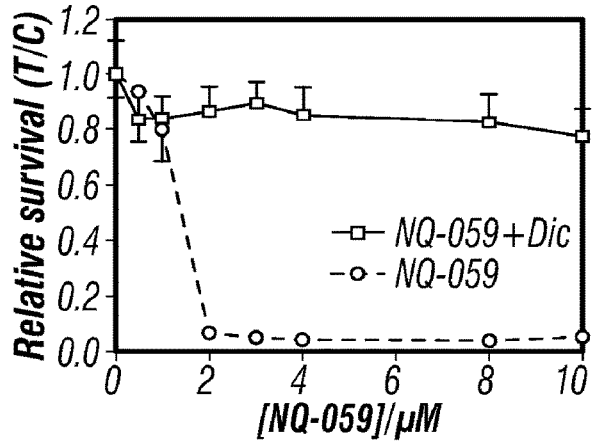
Figure 4C:
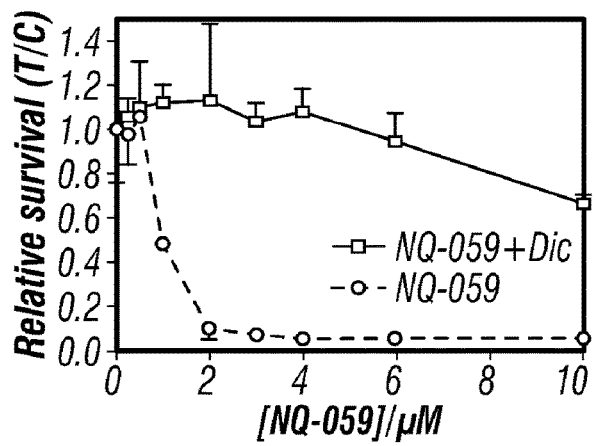
Figure 4D:
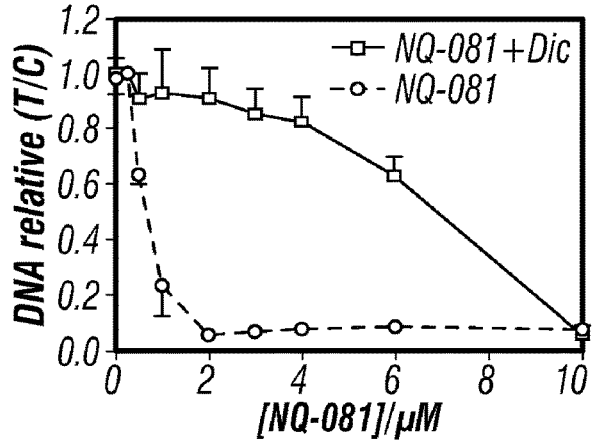
Figure 4E:
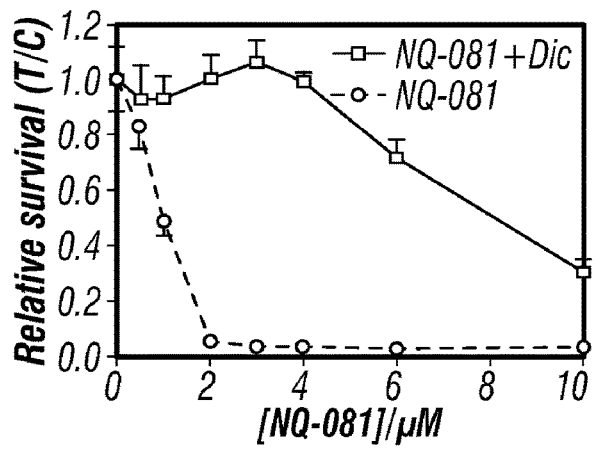
Figure 4F:
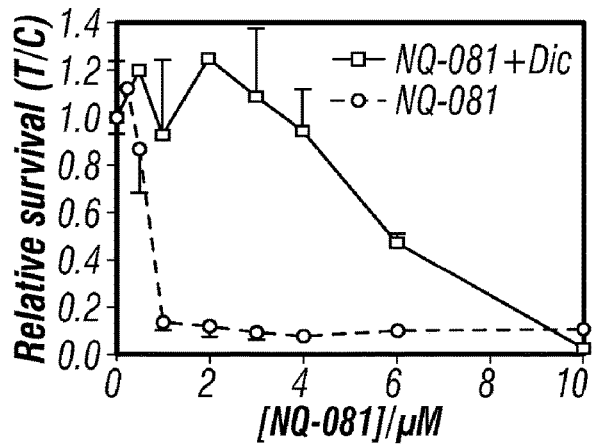
Figure 4G:
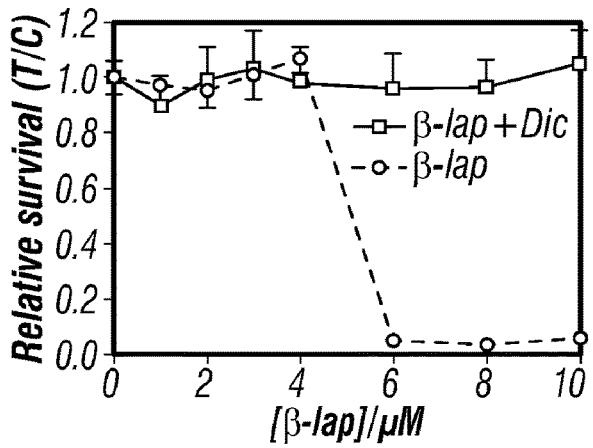
Figure 4H:
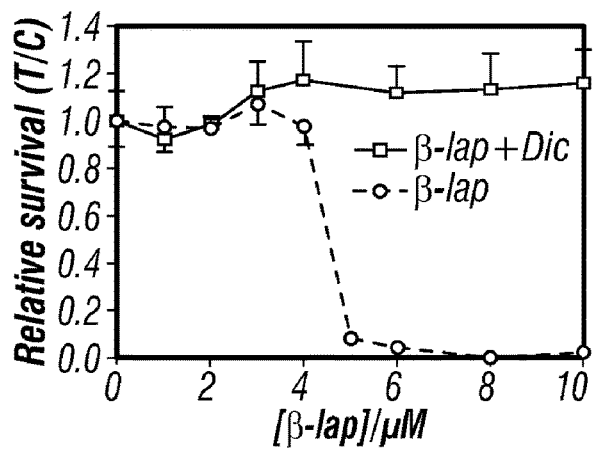
Figure 4I:
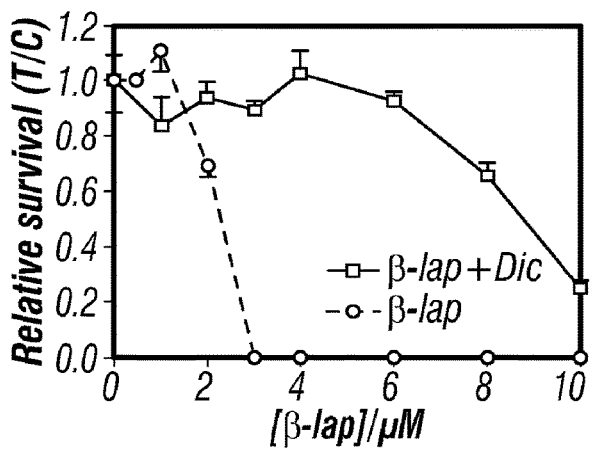
Figure 4J:
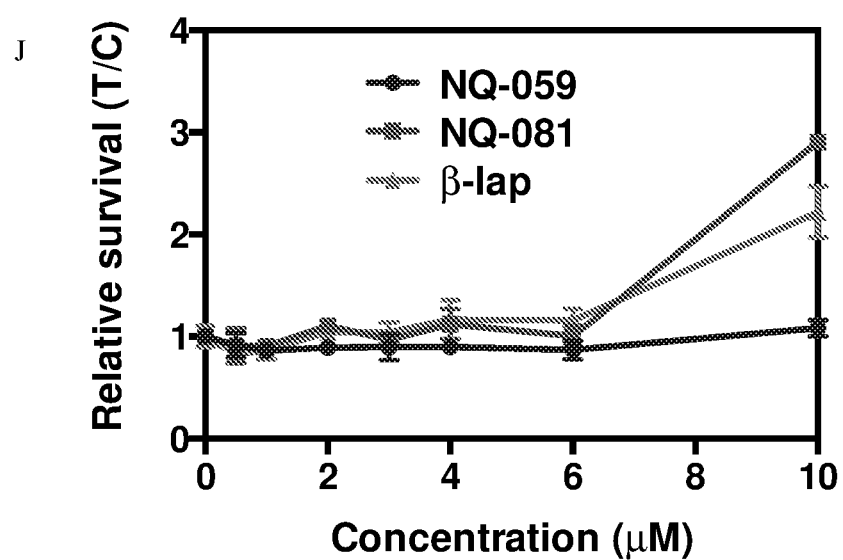

FIG. 1 shows the relative activity of the compounds based upon core structure Formula (I). The presence of an amide or a sulfonamide adjacent to carbonyl group showed increased activity relative to amine or oxygen containing groups. In FIGS. 2A & 2B, the activity was screened with different $R_3$ groups for compound with an amide group in the position adjacent to one of the ketones of the α,β-dicarbonyl group. Similar analysis is shown for the compounds with a sulfonamide group adjacent in FIGS. 3A & 3B.

B. Analysis of Compound 24 (NQ-059) and Compound 21 (NQ-081)

NQO1 Enzyme Assays. Naphthaquinones were monitored as NQO1 substrates using an NADH (Sigma, 400 μmol/L) recycling assay and human recombinant NQO1 (ab59663, Abcam), in which NADH oxidation to $NAD^+$ was monitored by absorbance ($A_{340\ nm}$) and data recorded at 1 second intervals for 20 seconds.

Cell Lines and Culture. Endogenous NQO1 overexpressing human MiaPaca-2 (pancreatic carcinoma), A549 (Nonesmall cell lung carcinoma), and MCF-7 (breast adenocarcinoma) were obtained (Bey, et al., 2007; Li, et al., 2011). All cell lines were grown in DMEM (Life Technologies) containing 5%-10% FBS (Fisher Scientific) in a 5% $CO_2$ and 95% air incubator at 37° C.

Relative Survival Assays. Relative survival was assessed by DNA content and colony forming assays as described (Dong, et al., 2010). Briefly, for DNA content, cells were seeded at $1\times10^4$ per well in 48-well plates and allowed to attach overnight. Cells were then mock treated or treated with various doses of naphthaquinones (for 2 hours) in the presence or absence of dicoumarol as indicated. Drug-free medium was then added and cells were allowed to grow for 5 to 7 days until control cells reached ~100% confluence. DNA content was then determined by Hoechst 33258 staining and fluorescence detection using a plate reader (Perkin-Elmer).

Formulation. β-lap-HPβCD formulation was prepared according to our previous report.[14] NQ-059 and HPβCD (1:45, w/w) were dissolved in EtOH, and then concentrated in vacuo to form a thin film or a sponge-like film. PBS was added, and a clear solution was formed with shaking. Immediately filtration through a Ø 0.45 m filter (Whatman), a stable solution was afforded, whose concentration was quantified by UV-vis at 256 nm.

Survival and Antitumor Efficacies. 6- to 8-week-old NOD-SCID female mice were tail-vein administrated with luciferase gene-transfected A549 cells (1.0×106), and randomized into groups (n=7-13/group), monitored for tumor formation in the lungs using bioluminescence (BLI) following treatment with vehicle, β-lap-HPβCD, or NQ-059-HPβCD. An average of $1.0\times10^7$ total photons was used before any therapies were given as described (Huang, et al., 2012). Animals were treated with vehicle, β-lap-HPβCD (20 mg/kg), or NQ-059-HPβCD (15 and 12 mg/kg) via tail vein and repeated five times every 3 days. Tumor-bearing mice were imaged using BLI to estimate relative tumor volumes as described (Ma, et al., 2015) using D-luciferin (Promega, 2.5 mg, subcutaneously injected). Relative tumor volume estimates were derived from BLI images of mice captured using a Xenogen Vivovision IVIS Lumina Imager (60 s exposure time). Animals were monitored daily for survival and morbidity. Mortality was recorded over times as a result of cancer-related deaths or drug-related toxicities (≥20% body weight loss relative to the start of therapy). Athymic Nu/Nu nude female mice (18-20 grams) were commercially obtained (Harlan). Human xenografts were generated by injecting $2\times10^6$ MiaPaca-2 cells subcutaneously in PBS/Matrigel into 6-week-old mice. Tumors were measured at indicated times with digital calipers (Fisher Scientific), and tumor volumes calculated (length×width$^2$×0.5). Treatments were initiated when subcutaneous tumors reached an average size of >100 mm (Cao, et al., 2003).

Statistical Analysis. Student t tests were used to determine statistical significance from experiments repeated at least 3 independent times. P values were reported by asterisks as indicated.

Hemolysis assay. Hemolysis was quantified and modified according to method previously described (Blanco, et al., 2010). Briefly, after treatment with the blood, the plasma was separated and tested with UV-Vis at 576 nm, and hemolysis was quantified comparing treatment group and control group.

Methemoglobinemia assay. Collected red blood cells were suspended in 96 well plates or single wells, then were treated with drug for certain time at 37° C. Immediately after the treatment completed, the cells were sit in ice-bath and lysed with 5% Triton X-100. The clear solution afforded were tested with UV-vis at 630 nm, and then were treated with 10M K3FeCN6 for 1 min. The yellow solution afforded was tested again at 630 nm.

Two compounds showed hemolytic activity with hemolysis above the therapeutic window threshold. Additional toxicity information is shown in Table 3.

TABLE 3

Compare acute toxicity and efficacy of NQ-059 with β-lap after injection on NOD-SCID mice

| | β-lap/HPβCD | NQ-059/HPβCD | |
|---|---|---|---|
| Dose (mg/kg) | 20 | 15 | 12 |
| Efficacy | + | ++++ | +++ |
| Acute Toxicity | +++ | ++ | − |
| Breathing | Labored | Slow and deep | Fast |
| Limbs | Lack of strength | Lack of strength | Normal |
| Body | Lack of strength, with seizures | Some seizures | Normal |
| Respond to poking | No | Yes | Yes |
| Recovery time (min) | 30 | 30 | N.D. |

+, positive grade;
−, negative grade;
N.D. not determined

TABLE 4

Therapeutic Window of NQ-059 and β-lapachone

| | β-Lap/HPβCD | NQ-059/HPβCD | |
|---|---|---|---|
| Dose (mg/kg) | 20 | 15 | 12 |
| Efficacy | + | ++++ | +++ |
| Acute Toxicity | +++ | ++ | − |

Furthermore, the compounds NQ-059 and NQ-081 were analyzed for the their activity in survival assays by measuring the amount of DNA present in four different cell lines, MiaPaca 2, MCF-7, A549, and H596. With cell line, H596, NQ-059 shows the lowest amount of DNA at the lowest concentration. With the other cell lines, MiaPaca 2, MCF-7, and A549, show decreased DNA amounts at lower concentrations relative to β-lapachone. This data is shown in FIGS. 4A-4J. Additional data is shown in Table 5.

relative to the formulations when cyclodextran is used or relative to the vehicle. See, for example, FIG. 10. Additional components such as excipients or surfactants were added to the composition. Table 7 shows results on stability of the nanoparticle when different components were added to the

TABLE 5

IC$_{50}$ values based upon cell survival assays and the inhibition of cell viability.

| | Inhibition of cell survival of DNA assay IC$_{50}$ (uM) | | | | | | | Inhibition of cell viability of ATP assay IC$_{50}$ (uM) |
|---|---|---|---|---|---|---|---|---|
| | MiaPaca 2 | | A549 | | MCF-7 | | H596* | |
| Compd. | Vehicle | Dic§ | Vehicle | Dic§ | Vehicle | Dic§ | Vehicle | MiaPac-2 Vehicle |
| NQ-059 | 0.88 | >10 | 1.25 | >10 | 0.95 | >10 | >10 | 0.97 |
| β-lap | 4.33 | >10 | 4.94 | >10 | 2.10 | 9.02 | >10 | 2.79 |
| Fold (IC$_{50\ \beta\text{-}lap}$/IC$_{50\ NQ\text{-}059}$) | 4.9 | N.D.¶ | 3.9 | N.D.¶ | 2.2 | N.D.¶ | N.D.¶ | 2.9 |

Figures 5A, 5B:
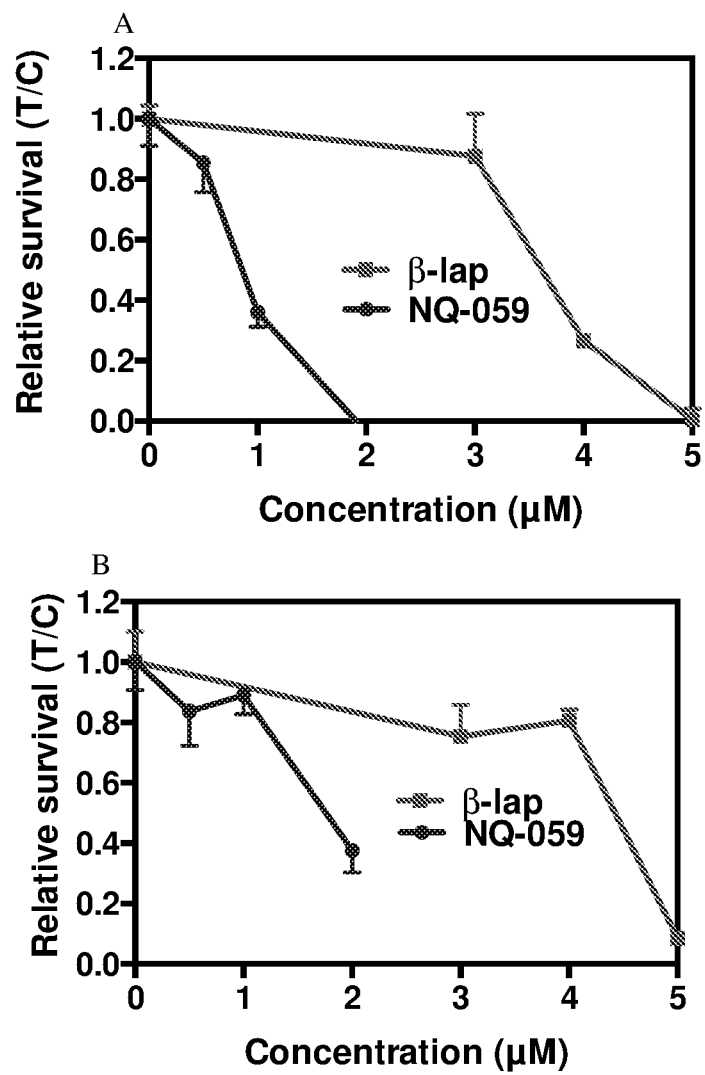
FIGS. 5A & 5B show the activity of NQ-059 relative to β-lapachone in MiaPaca-2 (FIG. 5A) and A549 (FIG. 5B) wherein the compounds are run on the same plate to remove plate to plate variability.
Figure 8:
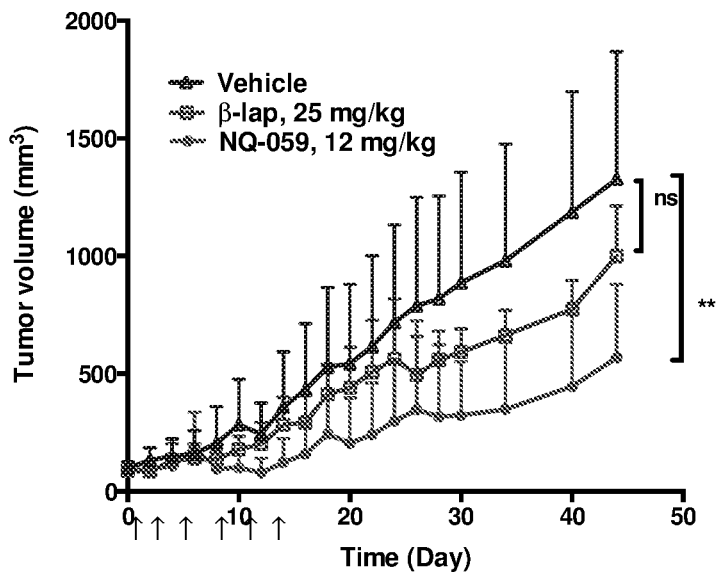
FIG. 8 shows the in vivo anti-tumor efficacy on nude mice bearing subcutaneous MiaPaca-2 model.

§Dic (dicoumarol), an inhibitor of NQO1;
*H596 is a cell line with a low NQO1 expression;
¶N.D., not determined To correct for potential plate to plate variability, NQ-059 and β-lapachone were analyzed on the same plate and NQ-059 showed increased activity in both the MiaPac2 and A549 cell lines and is shown in FIGS. 5A and 5B, respectively.

In FIGS. 6A and 6B the compounds were analyzed for activity in the NQO1 enzyme assay with several compounds showing improved activity relative to β-lapachone. Similarly, tumor growth was analyzed via bioluminescence imaging. After 74 days, β-lapachone showed some tumor growth with some minor tumor growth after day 44. Neither 12 mg/kg or 15 mg/kg NQ-059 showed any tumor growth after day 44 with 12 mg/kg showing some growth after 74 days. This analysis is quantified in FIGS. 7B and 7C wherein tumor volume and survival are significantly improved over the vehicle while β-lapachone only shows a small improvement over vehicle in terms of survival. Similar analysis was carried out with the subcutaneous MiaPaca-2 tumor model wherein NQ-059 showed a statistically significant improvement in tumor volume relative to the vehicle while β-lapachone did not.

Example 3—Formulation of Compound

A. Formulation with β-cyclodextran

Figure 9:
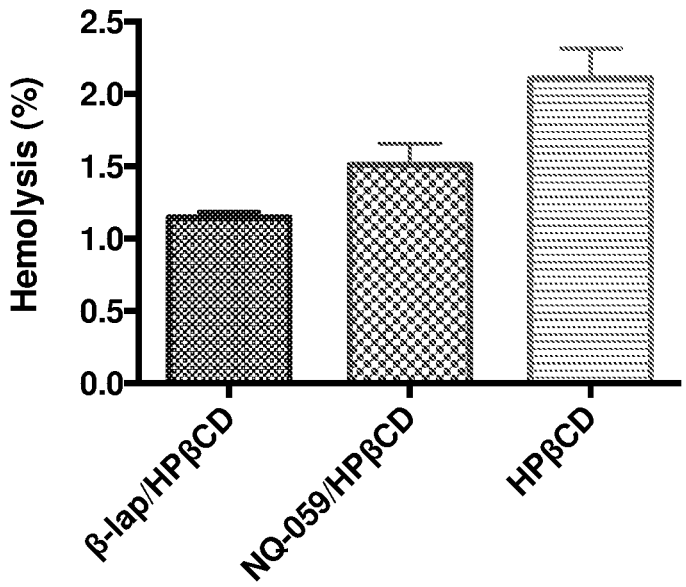
FIG. 9 shows a plot of the formulation protection from hemolysis for compound NQ-059 and β-lapachone formulated with a cyclodextran relative to the cyclodextran without the compound.
Figure 10:
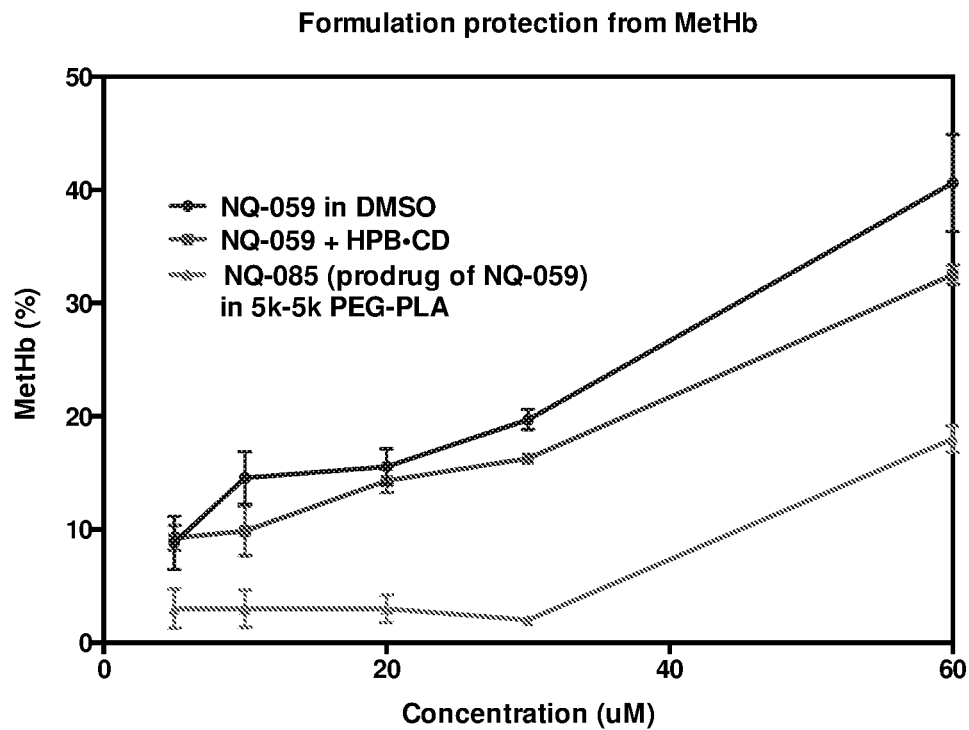
FIG. 10 shows a plot of the formulation protection from methemoglobinemia for the compound only, formulated in with a cyclodextran, or formulated as a nanoparticle.

The compounds, NQ-059, was formulated with a β-hydroxycyclodextran within a composition containing a mixture of the compound to the cyclodextran of 1:30 as noted in Table 6. As shown in FIGS. 9 and 10, the formulation of the compound with the show reduced toxicity such as hemolysis and methemoglobinemia relative to a blank cyclodextran or a DMSO vehicle.

TABLE 6

Composition of Compounds of the Present Disclosure and Cyclodextrans

| NQ-059/HPβCD | Concentration | stability at 4° C. |
|---|---|---|
| 1:30 | 2 mg/mL | <24 h |

B. Formulation with Nanoparticles

Additionally, the compounds can also be formulated as nanoparticles. These nanoparticles were prepared using PEG-PLA. This composition showed reduced hemolysis composition. The following excipients were used: oleic acid (OA), squalene (Sq), soybean oil (SO), cholesterol (Cho), tocopheryl acetate (VEAc), tocopherol (VE), medium chain monoglycerides (MCM), medium chain triglycerides (MCT).

TABLE 7

Loading Efficiency and Stability of Nanoparticles with Various Excipients

| Expt | 59/Expt/PEG-PLA2k2k | Loading efficiency % | Stability at 4° C. |
|---|---|---|---|
| VE | 10/0.5/89.9 | 89 | <16 hrs |
| | 10/1/89 | 89 | <16 hrs |
| | 10/2/88 | 87 | <16 hrs |
| | 10/4/86 | 87 | <16 hrs |
| | 15/0.75/84.25 | | <10 mins |
| | 15/1.5/83.5 | 86 | <16 hrs |
| | 15/3/82 | | <10 mins |
| VEAc | 10/0.5/89.9 | 79 | <16 hrs |
| | 10/1/89 | 69 | <16 hrs |
| | 10/2/88 | 62 | <4 hrs |
| OA | 10/0.5/89.9 | 85 | <16 hrs |
| | 10/1/89 | 96 | <16 hrs |
| | 10/2/88 | | <10 mins |
| SO | 10/0.5/89.9 | 56 | <30 mins |
| | 10/1/89 | 68 | <4 hrs |
| | 10/2/88 | 43 | <30 mins |
| MCM | 10/0.5/89.9 | 86 | <40 hrs |
| | 10/1/89 | 85 | <60 hrs |
| | 10/2/88 | 88 | <16 hrs |
| | 10/4/86 | 94 | <16 hrs |
| | 15/0.75/84.25 | 65 | <16 hrs |
| | 15/1.5/83.5 | 56 | <16 hrs |
| | 15/3/82 | 56 | <16 hrs |
| MCT | 10/0.5/89.9 | 87 | <16 hrs |
| | 10/1/89 | 88 | <16 hrs |
| | 10/2/88 | 85 | <16 hrs |
| Sq | 10/0.5/89.9 | 63 | <30 mins |
| | 10/1/89 | 66 | <30 mins |
| | 10/2/88 | 62 | <30 mins |
| Cho | 10/0.5/89.9 | 69 | <4 hrs |
| | 10/1/89 | 65 | <4 hrs |
| | 10/2/88 | 72 | <4 hrs |

Figure 11:
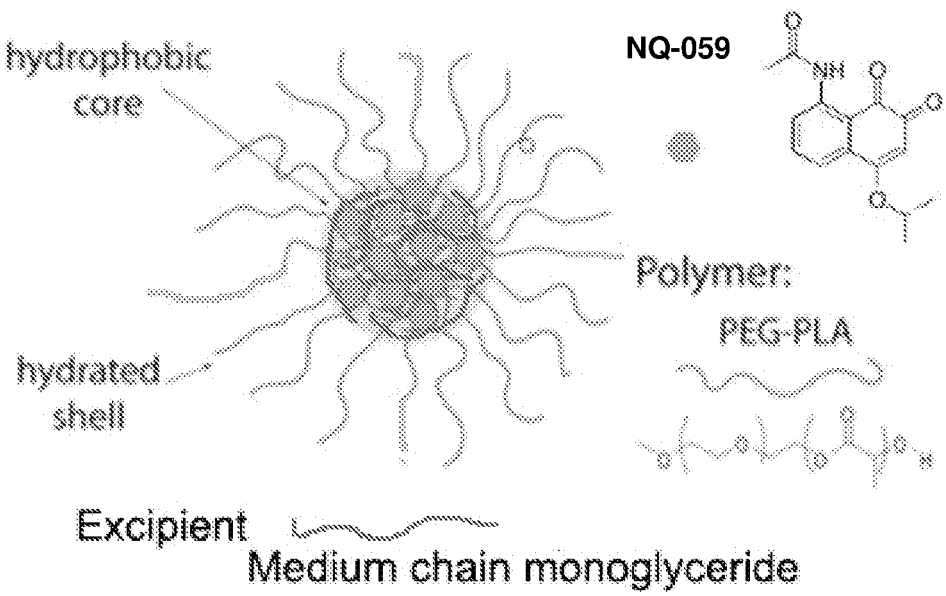
FIG. 11 shows a non-limiting example of a schematic of the nanoparticle composition with a diblock polymer, the compound, and one or more excipients.

The compositions with medium chain monoglycerides showed increased stability with a high loading efficiency. This particular composition was further analyzed which is shown in Table 8 and FIG. 11.

TABLE 8

Stability and Loading of Compositions Containing
PEG-PLA with Medium Chain Monoglycerides

| [NQ-059] (mg/mL) | Loading Efficiency | Loading Density | Stability at 4° C. | Diameter (nm) |
|---|---|---|---|---|
| 1.6 | 80% | 7% | >48 h | 19 ± 5 |

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Austin-Ward and Villaseca, *Rev. Med. Chil.*, 126(7):838-45, 1998.
Blanco et al., *Cancer Res.* 70(10):3896-3904, 2010.
Belinsky and Jaiswal, *Cancer Metast Rev.* 12(2):103-117, 1993.
Bey et al., *Proc. Nat. Acad. Sci.*, 104(28):11832-11837, 2007.
Bukowski et al., *Clin. Cancer Res.*, 4(10):2337-47, 1998.
Cao, et al., *Anticancer Research* 33(5):1785-1791, 2003.
Christodoulides et al., *Microbiology*, 144(Pt 11):3027-37, 1998.
Davidson et al., *J. Immunother.*, 21(5):389-98, 1998.
Dong et al., *Cancer Res.* 70(20):8088-8096, 2010.
Hanibuchi et al., *Int. J. Cancer,* 78(4):480-485, 1998.
Hellstrand et al., *Acta Oncol.*, 37(4):347-353, 1998.
Huang et al., *Cancer Res.* 72(12):3038-3047, 2012.
Hui and Hashimoto, *Infect. Immun.*, 66(11):5329-36, 1998.
Joseph et al., *Oncol Res.* 6(10-11):525-532, 1994.
Ju et al., *Gene Ther.*, 7(19):1672-1679, 2000.
Li et al., *Clinical Cancer Research.* 17(2):275-285, 2011.
Ma et al., *Journal of Controlled Release.* 200:201-211, 2015.
Malkinson et al., *Cancer Res.* 52(17):4752-4757, 1992.
Marfn et al., *BR. J. CANCER.* 76(7):923-929, 1997.
Mitchell et al., *Ann. NYAcad. Sci.*, 690:153-166, 1993.
Mitchell et al., *J. Clin. Oncol.*, 8(5):856-869, 1990.
Morton et al., *Arch. Surg.*, 127:392-399, 1992.
PCT Application Publication No. WO 1996/033988
PCT Application Publication No. WO 2004/045557
PCT Application Publication No. WO 2006/128120
PCT Application Publication No. WO 2008/066294
PCT Application Publication No. WO 2009/105166
Pietras et al., *Oncogene*, 17(17):2235-49, 1998.
Qin et al., *Proc. Natl. Acad. Sci. USA*, 95(24):14411-14416, 1998.
Ravindranath and Morton, *Intern. Rev. Immunol.*, 7: 303-329, 1991.
Rosenberg et al., *Ann. Surg.* 210(4):474-548, 1989.
Rosenberg et al., *N. Engl. J. Med.*, 319:1676, 1988.
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 6,262,095

What is claimed is:
1. A compound of the formula:

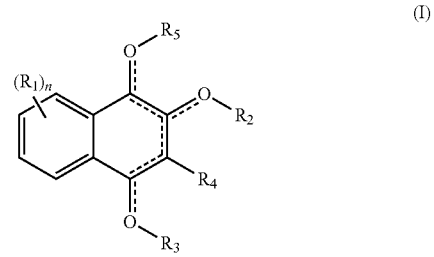

wherein:
$R_1$ is halo, nitro, substituted alkyl$_{(C \leq 8)}$, substituted alkoxy$_{(C \leq 8)}$, or —NR$_a$R$_b$, wherein:
$R_a$ or $R_b$ are each independently hydrogen or —C(O)-alkoxy$_{(C \leq 12)}$, alkyl$_{(C \leq 12)}$, acyl$_{(C \leq 12)}$, alkylsulfonyl$_{(C \leq 12)}$, arylsulfonyl$_{(C \leq 12)}$, or a substituted version of any of these groups; or
when n is more than 1, then both $R_1$ are taken together and are an alkoxydiyl$_{(C \leq 6)}$ or substituted alkoxydiyl$_{(C \leq 6)}$; or
—O-alkanediyl$_{(C \leq 6)}$-R$_c$, wherein:
$R_c$ is amino, alkylamino$_{(C \leq 8)}$, dialkylamino$_{(C \leq 8)}$, heterocycloalkyl$_{(C \leq 8)}$, or a substituted version of any of these groups;
$R_2$ is absent or alkyl$_{(C \leq 12)}$, cycloalkyl$_{(C \leq 12)}$, acyl$_{(C \leq 12)}$, -alkanediyl$_{(C \leq 6)}$-R$_c$, or a substituted version of any of these groups; wherein:
$R_c$ is amino, alkylamino$_{(C \leq 8)}$, dialkylamino$_{(C \leq 8)}$, heterocycloalkyl$_{(C \leq 8)}$, or a substituted version of any of these groups;
provided that $R_2$ is absent when the atom to which $R_2$ is bound is a part of a double bond, and when the atom to which $R_2$ is bound is part of a double bond, then $R_2$ is absent;
$R_3$ is absent or alkyl$_{(C \leq 12)}$, cycloalkyl$_{(C \leq 12)}$, acyl$_{(C \leq 12)}$, -alkanediyl$_{(C \leq 6)}$-R$_c$, —(CH$_2$CH$_2$O)$_m$R$_d$, or a substituted version of any of these groups; wherein:
$R_c$ is amino, alkylamino$_{(C \leq 8)}$, dialkylamino$_{(C \leq 8)}$, heterocycloalkyl$_{(C \leq 8)}$, or a substituted version of any of these groups;
$R_d$ is hydrogen, alkyl$_{(C \leq 6)}$, or substituted alkyl$_{(C \leq 6)}$; and
m is 1, 2, 3, 4, or 5;
provided that $R_3$ is absent when the atom to which $R_3$ is bound is a part of a double bond, and when the atom to which $R_3$ is bound is part of a double bond, then $R_3$ is absent;
$R_4$ is hydrogen, halo, alkyl$_{(C \leq 6)}$, or substituted alkyl$_{(C \leq 6)}$;
$R_5$ is absent or alkyl$_{(C \leq 12)}$, acyl$_{(C \leq 12)}$, or a substituted version of either of these groups;

provided that $R_5$ is absent when the atom to which $R_5$ is bound is a part of a double bond, and when the atom to which $R_5$ is bound is part of a double bond, then $R_5$ is absent; and n is 1, 2, 3, or 4;

provided that when $R_2$ and $R_5$ are $acyl_{(C \leq 12)}$ or substituted $acyl_{(C \leq 12)}$, then $R_3$ is $alkyl_{(C \leq 12)}$ or substituted $alkyl_{(C \leq 12)}$;

or a pharmaceutically acceptable salt thereof.

2. The compound of claim 1 further defined as:

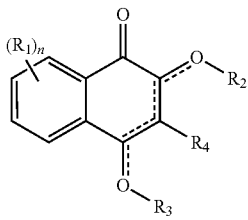

(II)

wherein:

$R_1$ is halo, nitro, substituted $alkyl_{(C \leq 8)}$, substituted $alkoxy_{(C \leq 8)}$, or $-NR_aR_b$, wherein:

$R_a$ or $R_b$ are each independently hydrogen or $-C(O)$-$alkoxy_{(C \leq 12)}$, $alkyl_{(C \leq 12)}$, $acyl_{(C \leq 12)}$, $alkylsulfonyl_{(C \leq 12)}$, $arylsulfonyl_{(C \leq 12)}$, or a substituted version of any of these groups; or when n is more than 1, then both $R_1$ are taken together and are an $alkoxydiyl_{(C \leq 6)}$ or substituted $alkoxydiyl_{(C \leq 6)}$; or $-O$-$alkanediyl_{(C \leq 6)}$-$R_c$, wherein:

$R_c$ is amino, $alkylamino_{(C \leq 8)}$, $dialkylamino_{(C \leq 8)}$, $heterocycloalkyl_{(C \leq 8)}$, or a substituted version of any of these groups;

$R_2$ is absent or $alkyl_{(C \leq 12)}$, $acyl_{(C \leq 12)}$, -$alkanediyl_{(C \leq 6)}$-$R_c$, or a substituted version of any of these groups; wherein:

$R_c$ is amino, $alkylamino_{(C \leq 8)}$, $dialkylamino_{(C \leq 8)}$, $heterocycloalkyl_{(C \leq 8)}$, or a substituted version of any of these groups;

provided that $R_2$ is absent when the atom to which $R_2$ is bound is a part of a double bond, and when the atom to which $R_2$ is bound is part of a double bond, then $R_2$ is absent;

$R_3$ is absent or $alkyl_{(C \leq 12)}$, $acyl_{(C \leq 12)}$, -$alkanediyl_{(C \leq 6)}$-$R_c$, $-(CH_2CH_2O)_mR_d$, or a substituted version of any of these groups; wherein:

$R_c$ is amino, $alkylamino_{(C \leq 8)}$, $dialkylamino_{(C \leq 8)}$, $heterocycloalkyl_{(C \leq 8)}$, or a substituted version of any of these groups;

$R_d$ is hydrogen, $alkyl_{(C \leq 6)}$, or substituted $alkyl_{(C \leq 6)}$; and m is 1, 2, 3, 4, or 5;

provided that $R_3$ is absent when the atom to which $R_3$ is bound is a part of a double bond, and when the atom to which $R_3$ is bound is part of a double bond, then $R_3$ is absent;

$R_4$ is hydrogen, halo, $alkyl_{(C \leq 6)}$, or substituted $alkyl_{(C \leq 6)}$; and n is 1, 2, 3, or 4;

or a pharmaceutically acceptable salt thereof.

3. The compound of claim 1, further defined as:

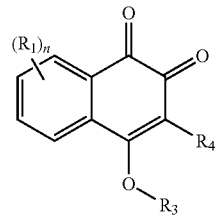

(III)

wherein:

$R_1$ is halo, nitro, substituted $alkyl_{(C \leq 8)}$, substituted $alkoxy_{(C \leq 8)}$, or $-NR_aR_b$, wherein:

$R_a$ or $R_b$ are each independently hydrogen or $-C(O)$-$alkoxy_{(C \leq 12)}$, $alkyl_{(C \leq 12)}$, $acyl_{(C \leq 12)}$, $alkylsulfonyl_{(C \leq 12)}$, $arylsulfonyl_{(C \leq 12)}$, or a substituted version of any of these groups; or when n is more than 1, then both $R_1$ are taken together and are an $alkoxydiyl_{(C \leq 6)}$ or substituted $alkoxydiyl_{(C \leq 6)}$; or $-O$-$alkanediyl_{(C \leq 6)}$-$R_c$, wherein:

$R_c$ is amino, $alkylamino_{(C \leq 8)}$, $dialkylamino_{(C \leq 8)}$, $heterocycloalkyl_{(C \leq 8)}$, or a substituted version of any of these groups;

$R_3$ is $alkyl_{(C \leq 12)}$, $acyl_{(C \leq 12)}$, -$alkanediyl_{(C \leq 6)}$-$R_c$, $-(CH_2CH_2O)_mR_d$, or a substituted version of any of these groups; wherein:

$R_c$ is amino, $alkylamino_{(C \leq 8)}$, $dialkylamino_{(C \leq 8)}$, $heterocycloalkyl_{(C \leq 8)}$, or a substituted version of any of these groups;

$R_d$ is hydrogen, $alkyl_{(C \leq 6)}$, or substituted $alkyl_{(C \leq 6)}$; and m is 1, 2, 3, 4, or 5;

$R_4$ is hydrogen, halo, $alkyl_{(C \leq 6)}$, or substituted $alkyl_{(C \leq 6)}$; and n is 1, 2, 3, or 4;

or a pharmaceutically acceptable salt thereof.

4. The compound of claim 1 further defined as:

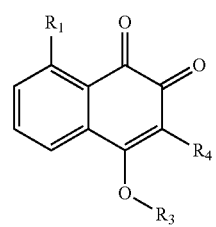

(IV)

wherein:

$R_1$ is halo, nitro, substituted $alkyl_{(C \leq 8)}$, substituted $alkoxy_{(C \leq 8)}$, or $-NR_aR_b$, wherein:

$R_a$ or $R_b$ are each independently hydrogen or $-C(O)$-$alkoxy_{(C \leq 12)}$, $alkyl_{(C \leq 12)}$, $acyl_{(C \leq 12)}$, $alkylsulfonyl_{(C \leq 12)}$, $arylsulfonyl_{(C \leq 12)}$, or a substituted version of any of these groups;

$R_3$ is $alkyl_{(C \leq 12)}$, $acyl_{(C \leq 12)}$, -$alkanediyl_{(C \leq 6)}$-$R_c$, $-(CH_2CH_2O)_mR_d$, or a substituted version of any of these groups; wherein:

$R_c$ is amino, alkylamino$_{(C \leq 8)}$, dialkylamino$_{(C \leq 8)}$, heterocycloalkyl$_{(C \leq 8)}$, or a substituted version of any of these groups;

$R_d$ is hydrogen, alkyl$_{(C \leq 6)}$, or substituted alkyl$_{(C \leq 6)}$; and m is 1, 2, 3, 4, or 5; and $R_4$ is hydrogen, halo, alkyl$_{(C \leq 6)}$, or substituted alkyl$_{(C \leq 6)}$;

or a pharmaceutically acceptable salt thereof.

5. The compound of claim 1 further defined as:

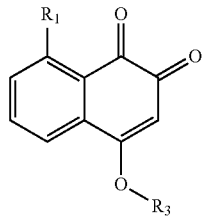

(V)

wherein:

$R_1$ is halo, nitro, substituted alkyl$_{(C \leq 8)}$, substituted alkoxy$_{(C \leq 8)}$, or —NR$_a$R$_b$, wherein:

$R_a$ or $R_b$ are each independently hydrogen or —C(O)-alkoxy$_{(C \leq 12)}$, alkyl$_{(C \leq 12)}$, acyl$_{(C \leq 12)}$, alkylsulfonyl$_{(C \leq 12)}$, arylsulfonyl$_{(C \leq 12)}$, or a substituted version of any of these groups; and $R_3$ is alkyl$_{(C \leq 12)}$, acyl$_{(C \leq 12)}$, -alkanediyl$_{(C \leq 6)}$-R$_c$, —(CH$_2$CH$_2$O)$_m$R$_d$, or a substituted version of any of these groups; wherein:

$R_c$ is amino, alkylamino$_{(C \leq 8)}$, dialkylamino$_{(C \leq 8)}$, heterocycloalkyl$_{(C \leq 8)}$, or a substituted version of any of these groups;

$R_d$ is hydrogen, alkyl$_{(C \leq 6)}$, or substituted alkyl$_{(C \leq 6)}$; and m is 1, 2, 3, 4, or 5;

or a pharmaceutically acceptable salt thereof.

6. The compound of claim 1, wherein $R_1$ is —NR$_a$R$_b$, wherein:

$R_a$ or $R_b$ are each independently hydrogen or —C(O)-alkoxy$_{(C \leq 12)}$, alkyl$_{(C \leq 12)}$, acyl$_{(C \leq 12)}$, alkylsulfonyl$_{(C \leq 12)}$, arylsulfonyl$_{(C \leq 12)}$, or a substituted version of any of these groups.

7. The compound of claim 6, wherein $R_a$ is acyl$_{(C \leq 8)}$ or substituted acyl$_{(C \leq 8)}$.

8. The compound of claim 6, wherein $R_a$ is alkylsulfonyl$_{(C \leq 8)}$ or substituted alkylsulfonyl$_{(C \leq 8)}$.

9. The compound of claim 6, wherein $R_b$ is hydrogen.

10. The compound of claim 1, wherein $R_2$ is absent.

11. The compound of claim 1, wherein $R_3$ is alkyl$_{(C \leq 8)}$ or substituted alkyl$_{(C \leq 8)}$.

12. The compound of claim 1, wherein $R_3$ is —(CH$_2$CH$_2$O)$_m$R$_d$, wherein:

$R_d$ is hydrogen, alkyl$_{(C \leq 6)}$, or substituted alkyl$_{(C \leq 6)}$; and m is 1, 2, 3, 4, or 5.

13. The compound of claim 1, wherein $R_4$ is hydrogen or halo.

14. The compound of claim 1, wherein $R_5$ is absent.

15. The compound of claim 1, wherein n is 1, 2, or 3.

16. The compound of claim 1, wherein the compound is further defined as:

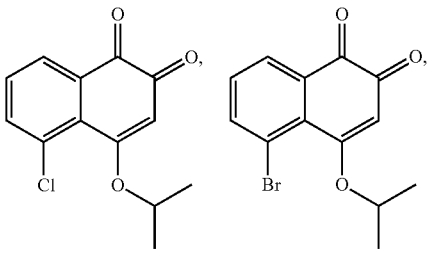

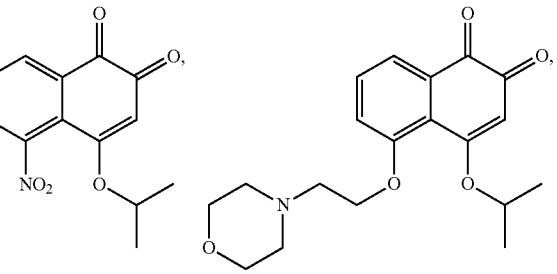

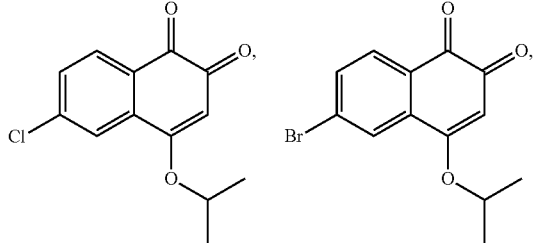

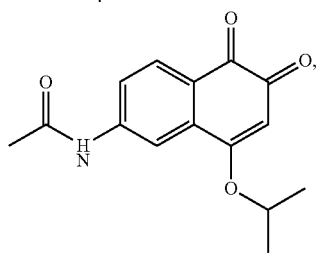

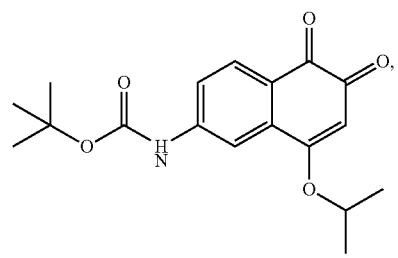

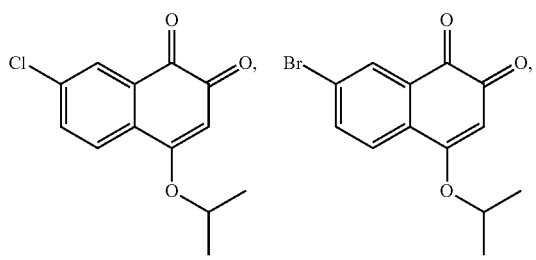

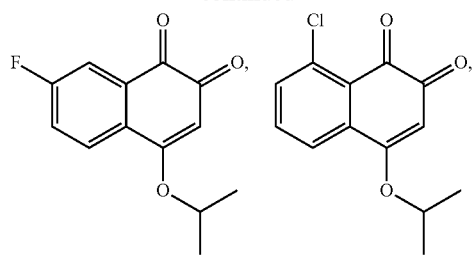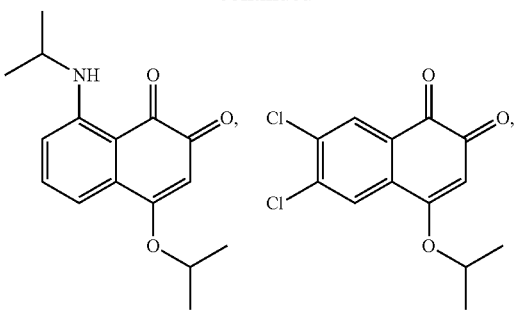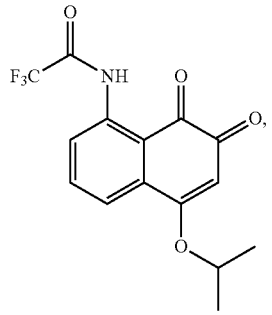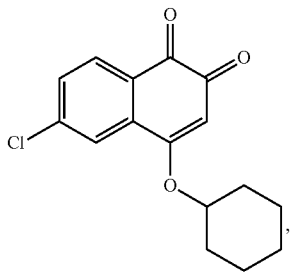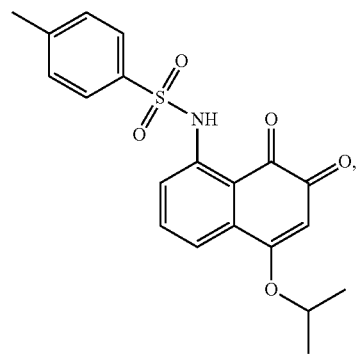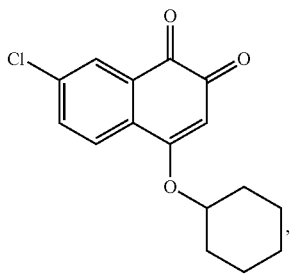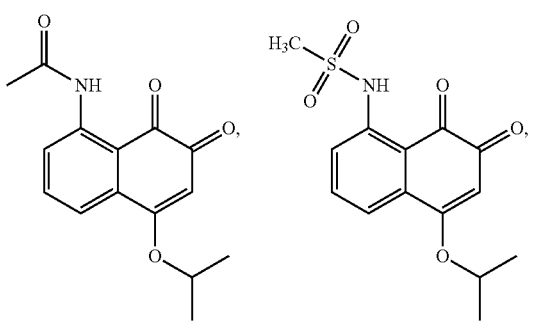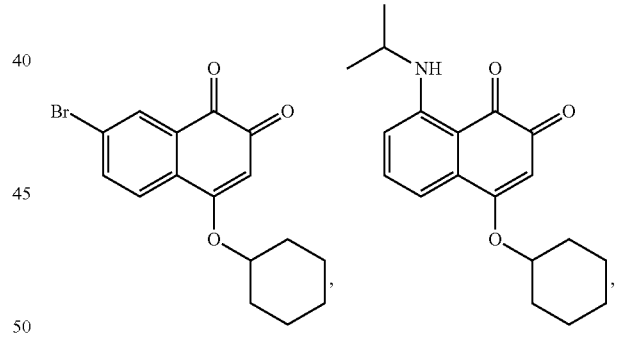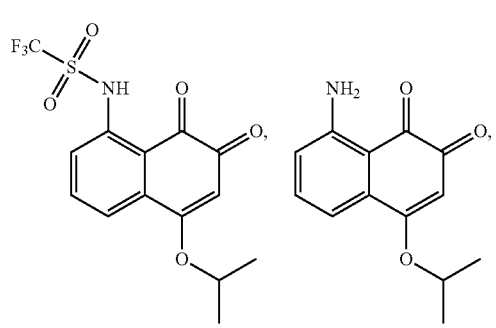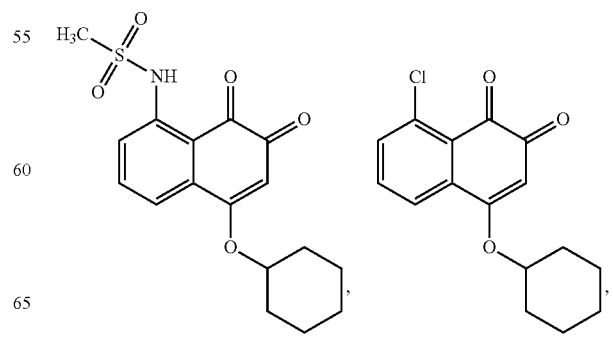

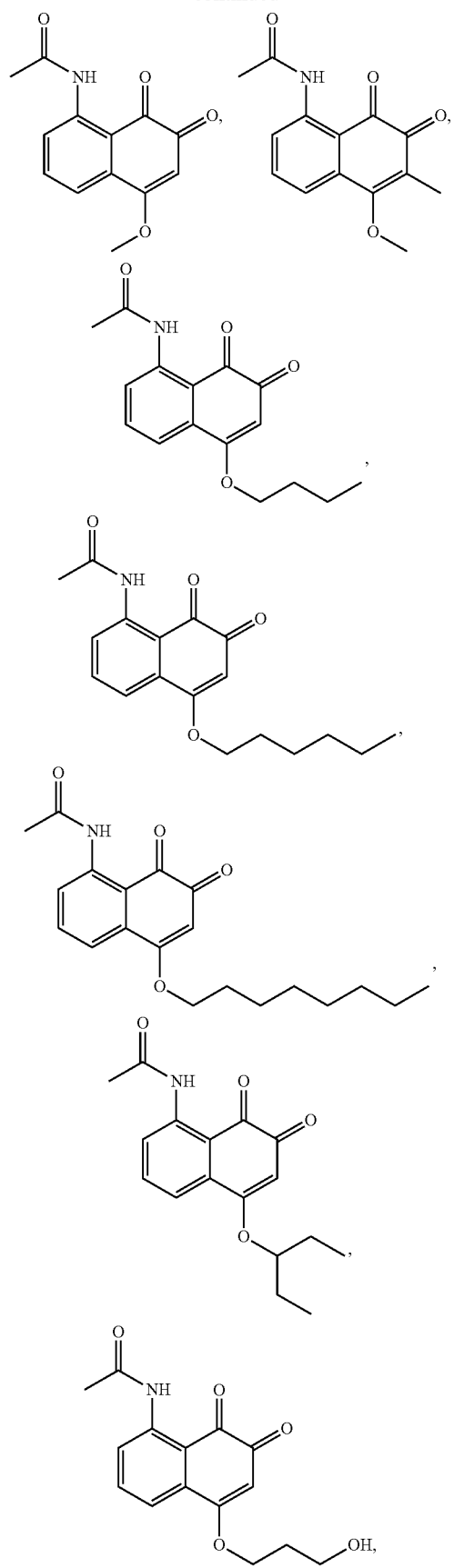
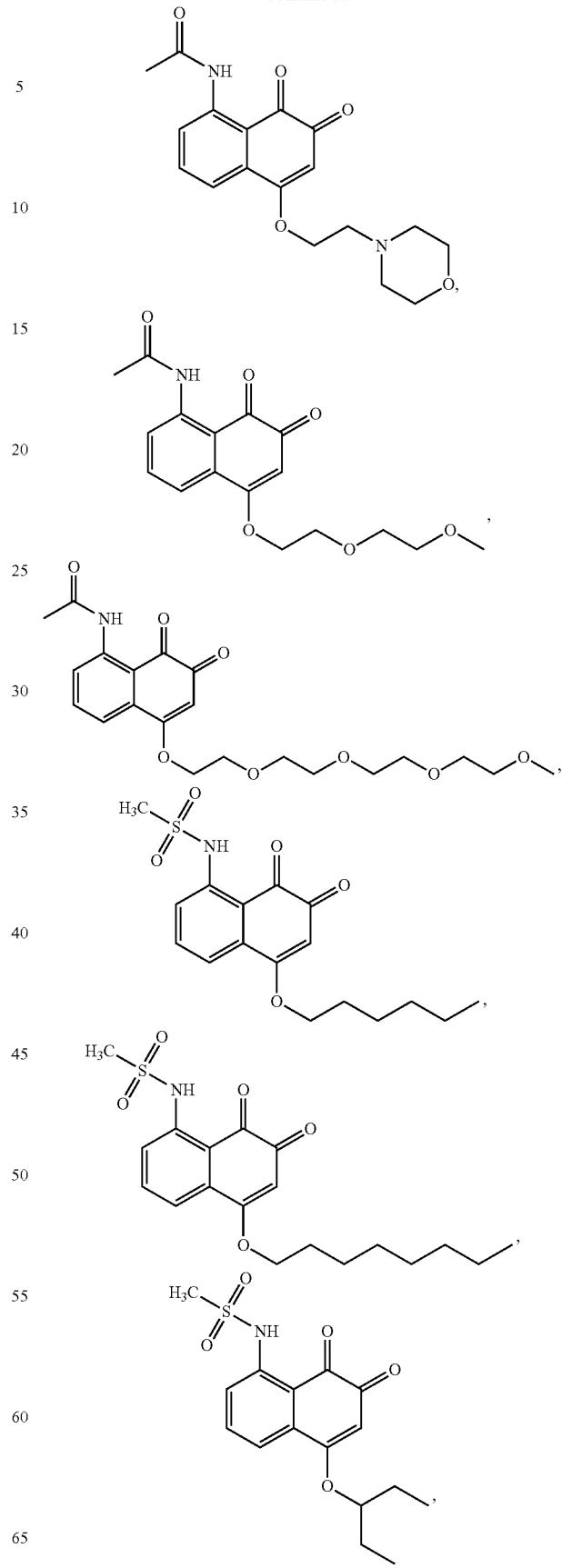

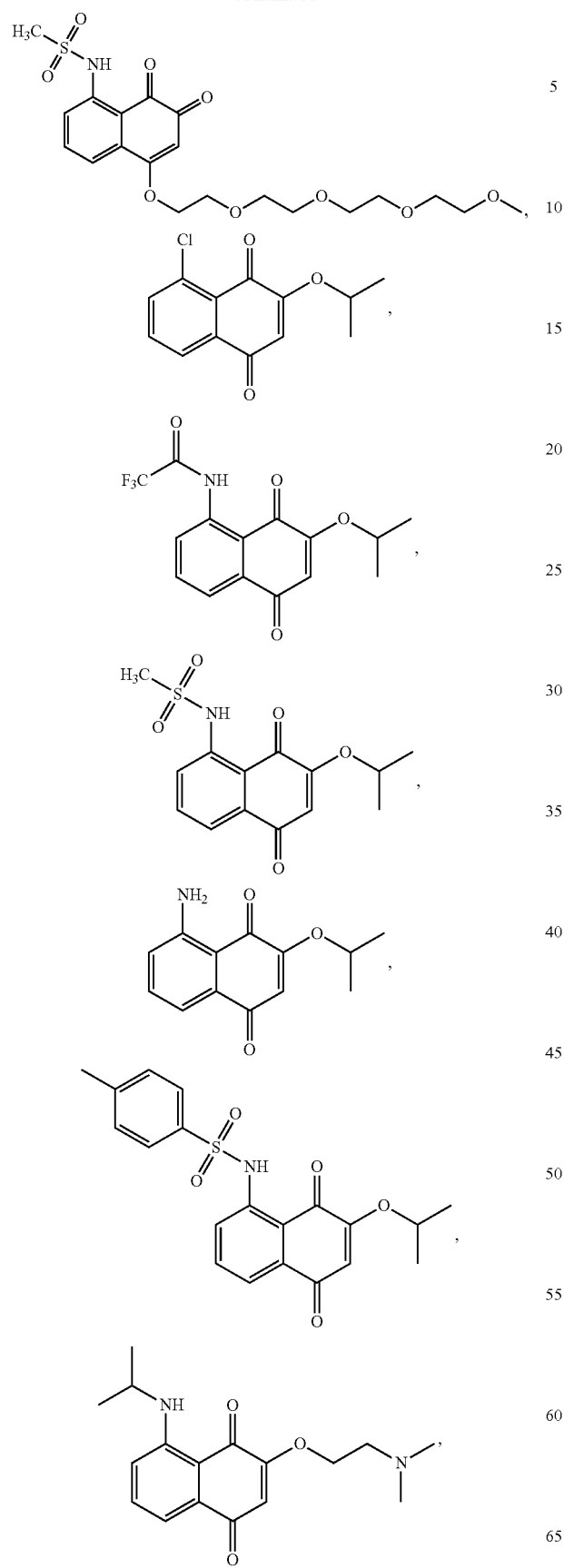
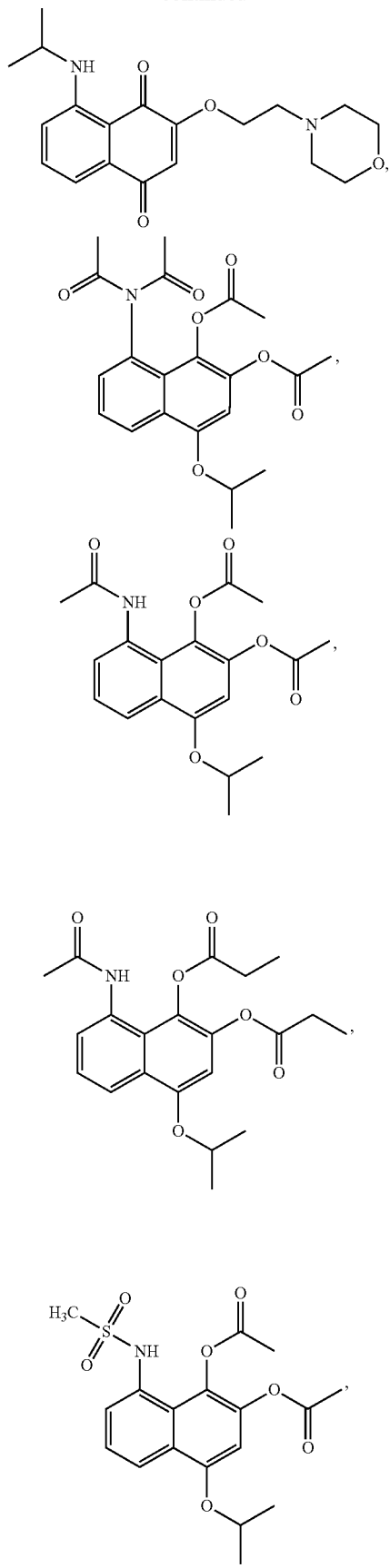

115
-continued
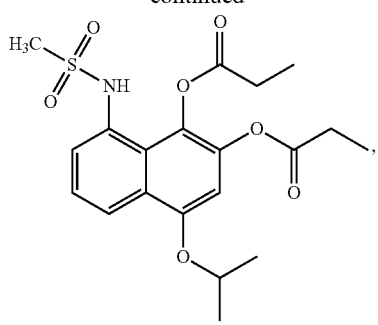
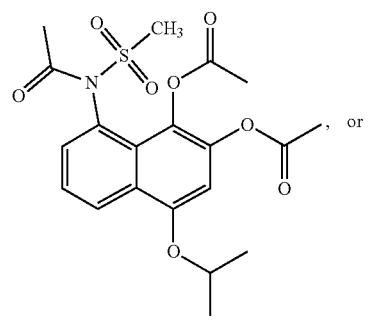
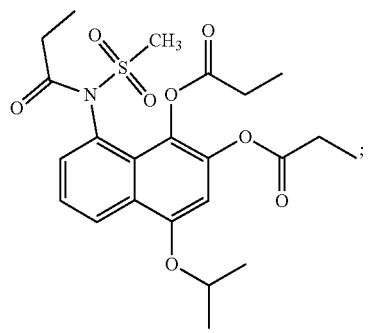
or a pharmaceutically acceptable salt.
17. The compound of claim 16, wherein the compound is further defined as:
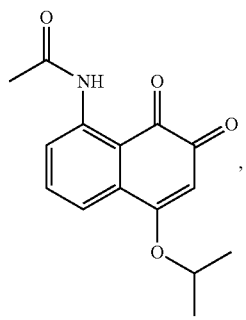
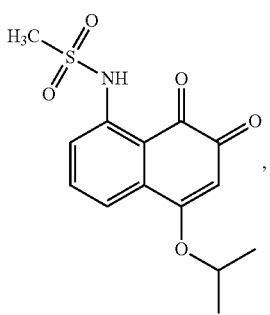
116
-continued
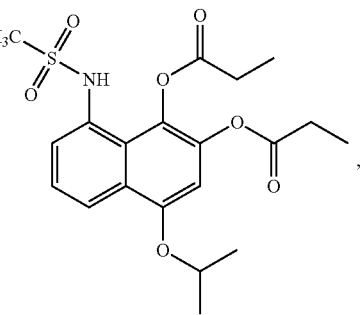

-continued
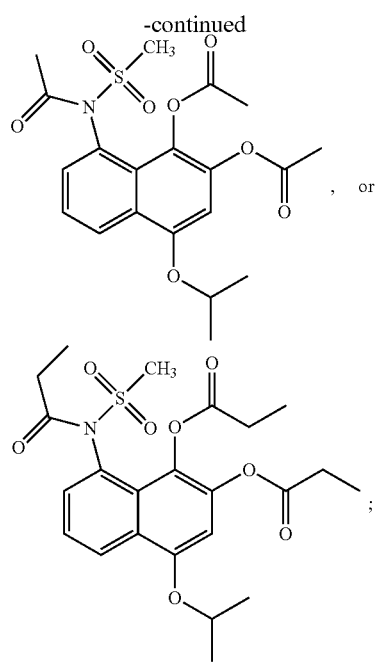
or a pharmaceutically acceptable salt.
18. A pharmaceutical composition comprising:
(a) a compound of claim 1; and
(b) a pharmaceutically acceptable carrier.
* * * * *

UNITED STATES PATENT AND TRADEMARK OFFICE
CERTIFICATE OF CORRECTION

Page 1 of 2

PATENT NO. : 10,829,427 B2
APPLICATION NO. : 16/063347
DATED : November 10, 2020
INVENTOR(S) : Jinming Gao et al.

It is certified that error appears in the above-identified patent and that said Letters Patent is hereby corrected as shown below:

In the Claims

In Claim 16, Column 110, Lines 36-50, delete " 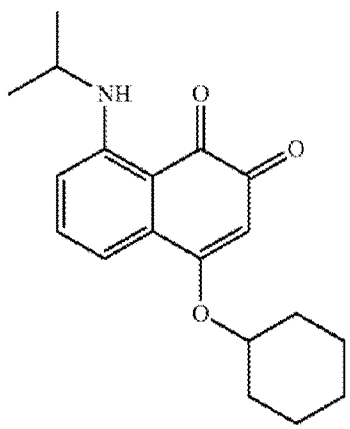 " and insert -- 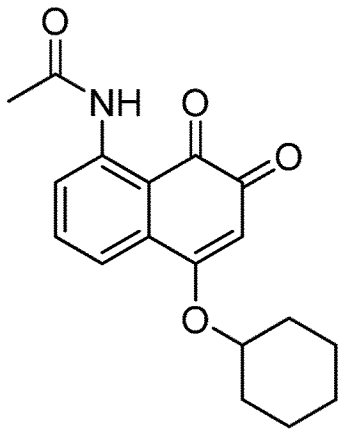 -- therefor.

In Claim 16, Column 113, Lines 57-66, delete " 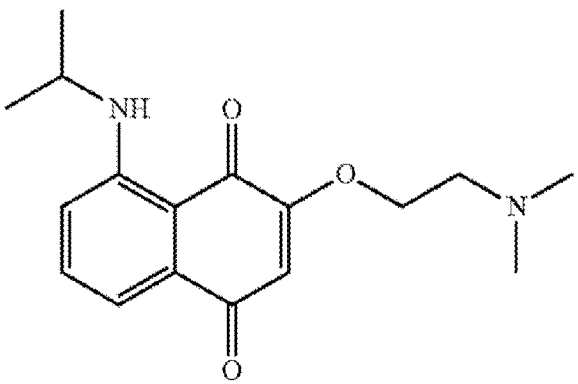 " and insert

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,829,427 B2

-- 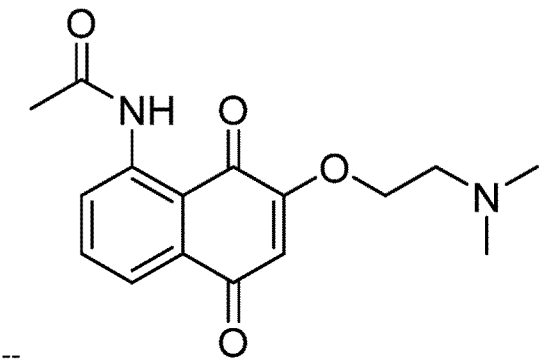 -- therefor.

In Claim 16, Column 114, Lines 1-12, delete

" 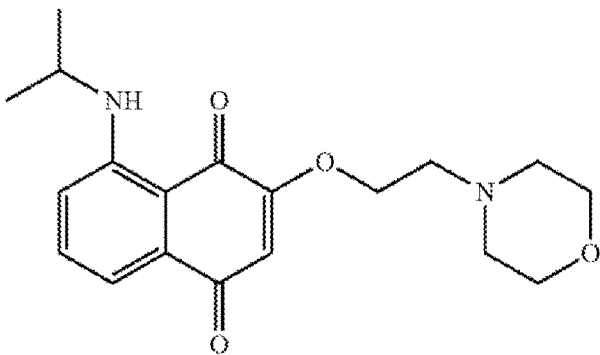 " and insert

-- 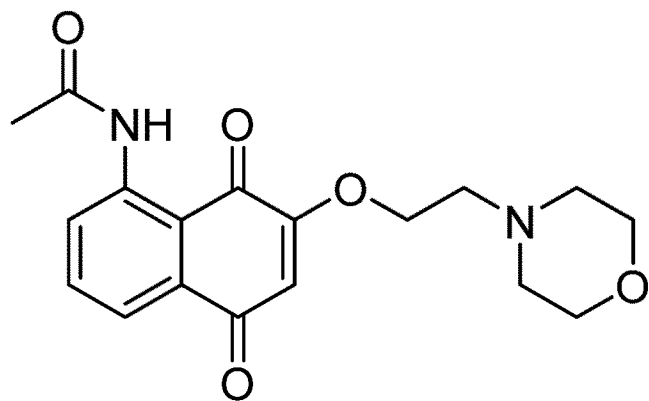 -- therefor.